United States Patent
Kyostio-Moore et al.

(10) Patent No.: US 10,815,497 B2
(45) Date of Patent: Oct. 27, 2020

(54) PRODUCTION OF OVERSIZED ADENO-ASSOCIATED VECTORS

(71) Applicant: Genzyme Corporation, Cambridge, MA (US)

(72) Inventors: Sirkka Kyostio-Moore, Ashland, MA (US); David Souza, Waltham, MA (US); Karen Vincent, Carlisle, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 15/565,020

(22) PCT Filed: Apr. 7, 2016

(86) PCT No.: PCT/US2016/026486
§ 371 (c)(1),
(2) Date: Oct. 6, 2017

(87) PCT Pub. No.: WO2016/164609
PCT Pub. Date: Oct. 13, 2016

(65) Prior Publication Data
US 2019/0048362 A1    Feb. 14, 2019

Related U.S. Application Data

(60) Provisional application No. 62/220,067, filed on Sep. 17, 2015, provisional application No. 62/144,862, filed on Apr. 8, 2015.

(51) Int. Cl.
| | |
|---|---|
| C12N 15/86 | (2006.01) |
| A61K 38/17 | (2006.01) |
| A61P 11/00 | (2006.01) |
| A61P 21/00 | (2006.01) |
| C12N 7/00 | (2006.01) |
| C07K 14/755 | (2006.01) |

(52) U.S. Cl.
CPC .......... *C12N 15/86* (2013.01); *A61K 38/1709* (2013.01); *A61P 11/00* (2018.01); *A61P 21/00* (2018.01); *C07K 14/755* (2013.01); *C12N 7/00* (2013.01); *C12N 2710/10041* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | |
|---|---|---|
| 6,566,118 B1 | 5/2003 | Atkinson et al. |
| 6,596,535 B1 | 7/2003 | Carter |
| 6,723,551 B2 | 4/2004 | Kotin et al. |
| 6,989,264 B2 | 1/2006 | Atkinson et al. |
| 7,125,717 B2 | 10/2006 | Carter |
| 7,465,583 B2 | 12/2008 | Samulski et al. |
| 7,785,888 B2 | 8/2010 | Carter |
| 7,790,154 B2 | 9/2010 | Samulski et al. |
| 7,846,729 B2 | 12/2010 | Carter |
| 8,093,054 B2 | 1/2012 | Carter |
| 8,137,948 B2 | 3/2012 | Qu et al. |
| 8,283,151 B2 | 10/2012 | Schmidt et al. |
| 8,361,457 B2 | 1/2013 | Samulski et al. |
| 2004/0092008 A1 | 5/2004 | Snyder et al. |
| 2004/0224411 A1 | 11/2004 | Clark et al. |
| 2007/0042462 A1 | 2/2007 | Hildinger |
| 2012/0066783 A1 | 3/2012 | Kay et al. |
| 2012/0164106 A1 | 6/2012 | Schaffer et al. |
| 2013/0323226 A1 | 12/2013 | Wilson et al. |

FOREIGN PATENT DOCUMENTS

| | | |
|---|---|---|
| WO | WO-2001/027303 A1 | 4/2001 |
| WO | WO-2003/042397 A2 | 5/2003 |
| WO | WO 2010/148143 A1 | 12/2010 |
| WO | WO-2014/064277 A1 | 5/2014 |
| WO | WO-2015/038625 A1 | 3/2015 |
| WO | WO-2015/168666 A2 | 11/2015 |
| WO | WO-2016/130591 A2 | 8/2016 |

OTHER PUBLICATIONS

Allocca, et al. (2008) "Serotype-dependent packaging of large genes in adeno-associated viral vectors results in effective gene delivery in mice", The Journal of Clinical Investigation, 118(5): 1955-64. (Year: 2008).*

Clark (2002) "Recent advances in recombinant adeno-associated virus vector production", Kidney International, 61(symposium 1): pp. S9-S15. (Year: 2002).*

Han, et al. (2012) DNA nanoparticle-mediated ABCA4 delivery resuces Stargardt dystrophy in mice, 122(9): 3221-26. (Year: 2012).*

U.S. Appl. No. 62/105,714, filed Jan. 20, 2015, O'riordan et al.

Berkowitz, S.A. et al. (2007). "Monitoring the Homogeneity of Adenovirus Preparations (A Gene Therapy Delivery System) Using Analytical Ultracentrifugation," *Anal. Biochem.* 362:16-37.

Boshart, M. et al. (Jun. 1985). "A Very Strong Enhancer is Located Upstream of an Immediate Early Gene of Human Cytomegalovius," *Cell* 41:521-530.

Bossis, I. et al. (Jun. 2003). "Cloning of an Avian Adeno-Associated Virus (AAAV) and Generation of Recombinant AAAV Particles," *J. Virol.* 77(12):6799-810.

Clark, K.R. et al. (Apr. 10, 1999). "Highly Purified Recombinant Adeno-Associated Virus Vectors are Biologically Active and Free of Detectable Helper and Wild-Type Viruses," *Hum. Gene Ther.* 10:1031-1039.

(Continued)

*Primary Examiner* — Robert M Kelly
(74) *Attorney, Agent, or Firm* — Morrison & Foerster LLP

(57) ABSTRACT

Provided herein are methods for producing an adeno-associated virus (AAV) particle containing an oversized recombinant AAV genome (e.g., greater than 4.7 kb). In some aspects, the invention provides AAV particles and AAV vectors comprising oversized rAAV genomes. Producer cell lines to produce AAV particles comprising oversized genomes are also provided.

22 Claims, 20 Drawing Sheets
Specification includes a Sequence Listing.

(56) References Cited

OTHER PUBLICATIONS

Cole, J.L. et al. (1999) "Analytical Ultracentrifugation as a Contemporary Biomolecular Research Tool," *J. Biomol. Tech.* 10:163-176.
Cole, J.L. et al. (2008) "Analytical Ultracentrifugation: Sedimentation Velocity and Sedimentation Equilibrium," *Methods Cell Biol.* 84:143-179.
Conway, J.E. et al. (Nov. 1997) "Recombinant Adeno-Associated Virus Type 2 Replication and Packaging Is Entirely Supported by a Herpes Simplex Virus Type 1 Amplicon Expressing Rep and Cap" *J. Virology* 71(11):8780-8789.
Costa, R.H. et al. (Dec. 1986). "Transcriptional Control of the Mouse Prealbumin (Transthyretin) Gene: Both Promoter Sequences and a Distinct Enhancer are Cell Specific," *Mol Cell Biol* 6(12):4697-4708.
Davidson, B.L. et al. (Mar. 28, 2000). "Recombinant Adeno-Associated Virus Type 2, 4, and 5 Vectors: Transduction of Variant Cell Types and Regions in the Mammalian Central Nervous System," *PNAS* 97(7):3428-3432.
Dong, J-Y et al. (Nov. 10, 1996). "Quantitative Analysis of the Packaging Capacity of Recombinant Adeno-Associated Virus," *Human Gene Therapy* 7:2101-2112.
Fisher, K.J. et al. (Jan. 1996). "Transduction with Recombinant Adeno-Associated Virus for Gene Therapy is Limited by Leading-Strand Synthesis," *J. Virol.* 70(1):520-532.
Furst, A. (May 1997). "The XL-I Analytical Ultracentrifuge with Rayleigh Interference Optics" *Eur. Biophys. J.* 35:307-310.
Gao, G. et al. (Jun. 2004). "Clades of Adeno-Associated Viruses are Widely Disseminated in Human Tissues," *J. Virol.* 78(12):6381-6388.
Gao, G. et al. (May 13, 2003). "Adeno-associated viruses undergo substantial evolution in primates during natural infections," *PNAS* 100(10):6081-6086.
Gao, G-P. et al. (Sep. 3, 2002). "Novel Adeno-Associated Viruses from Rhesus Monkeys as Vectors for Human Gene Therapy," *PNAS* 99(18):11854-11859.
Goodwin, E.C. et al. (Aug. 15, 1992). "The 3'-Flanking Sequence of the Bovine Growth Hormone Gene Contains Novel Elements Required for Efficient and Accurate Polyadenylation," *J. Biol. Chem.* 267(23):16330-16334.
Gossen, M. et al. (1992). "Tight Control of Gene Expression in Mammalian Cells by Tetracycline-Responsive Promoters," *Proc. Natl. Acad. Sci. USA* 89:5547-5551.
Gossen, M. et al. (Jun. 23, 1995). "Transcriptional Activation by Tetracyclines in Mammalian Cells," *Science* 268:1766-1769.
Grose, W.E. et al. (Jun. 15, 2012). "Homologous Recombination Mediates Functional Recovery of Dysferlin Deficiency following AAV5 Gene Transfer," *PLOS ONE* 7(6):e39233, 12 pages.
Groth, A.C. et al. (May 23, 2000). "A Phage Integrase Directs Efficient Site-Specific Integration in Human Cells," *Proc. Natl. Acad. Sci.* 97(11):5995-6000.
Guo, Z.S. et al. (1996). "Evaluation of Promoter Strength for Hepatic Gene Expression in Vivo Following Adenovirus-Mediated Gene Transfer," *Gene Ther.* 3(9):802-810.
Harvey, D.M. et al. (1998). "Inducible Control of Gene Expression: Prospects for Gene Therapy," *Curr. Opin. Chem. Biol.* 2:512-518.
Hirsch, M.L. et al. (Dec. 2013, e-pub. Sep. 17, 2013). "Oversized AAV Transduction is Mediated via a DNA-PKcs-Independent, Rad51C-Depentent Repair Pathway," *Molecular Therapy* 21(12):2205-2216.
International Search Report dated Nov. 7, 2016, for PCT Application No. PCT/US2016/026486, filed on Apr. 7, 2016, 8 pages.
Jiang, H. et al. (Jul. 1, 2006; e-pub. Mar. 7, 2006). "Multiyear therapeutic benefit of AAV serotypes 2, 6, and 8 delivering factor VIII to hemophilia A mice and dogs," *Blood* 108:107-115.
Kim, D.W. et al. (1990). "Use of the Human Elongation Factor 1α Promoter as a Versatile and Efficient Expression System," *Gene* 91(2):217-223.
Kim, T.K. et al. (Aug. 2010). "Mammalian Cell Transfection: The Present and the Future," *Anal. Bioanal. Chem.* 397(8):3173-3178.
King, J.A. et al. (Jun. 15, 2001). "DNA Helicase-Mediated Packaging of Adeno-Associated Virus Type 2 Genomes into Preformed Capsids" *EMBO J.* 20(12):3282-3291.
Kotin, R.M. (Jul. 1994). "Prospects for the Use of Adeno-Associated Virus as a Vector for Human Gene Therapy," *Hum. Gene Ther.* 5(7):793-801.
Krysan, P.J. et al. (1989). "Isolation of Human Sequences That Replicate Autonomously in Human Cells," *Mol. Cell Biol.* 9(3):1026-1033.
Kyostio-Moore, S. et al. (2016, e-pub. Feb. 24, 2016). "The Impact of Minimally Oversized Adeno-Associated Viral Vectors Encoding Human Factor VIII on Vector Potency in vivo", *Molecular Therapy—Methods & Clinical Development* 3:16006, 12 pages.
Liu, X.L. et al. (1999). "Production of recombinant adeno-associated virus vectors using a packaging cell line and a hybrid recombinant adenovirus," *Gene Ther.* 6:293-299.
Lu, H. et al. (Jun. 2008). "Complete Correction of Hemophilia A with Adeno-Associated Viral Vectors Containing a Full-Size Expression Cassette," *Human Gene Therapy* 19(6):648-654.
Magari, S.R. et al. (1997). "Pharmacologic Control of a Humanized Gene Therapy System Implanted into Nude Mice," *J. Clin. Invest.* 100:2865-2872.
Martin, J. et al. (Aug. 2013). "Generation and Characterization of Adeno-Associated Virus Producer Cell Lines for Research and Preclinical Vector Production," *Human Gene Therapy Methods* 24(4):253-269.
McLaughlin, S.K. et al. (Jun. 1988). "Adeno-Associated Virus General Transduction Vectors: Analysis of Proviral Structures," *J. Virol.* 62(6):1963-1973.
Nambiar, B. et al. (May 2016). "Evaluation of Producer Cell Line Platform for Production of Oversized AAV-FVIII Vectors," *Molecular Therapy* 24(Suppl.1):S40, 1page.
No, D. et al. (Apr. 1996). "Ecdysone-lnducible Gene Expression in Mammalian Cells and Transgenic Mice," *Proc. Natl. Acad. Sci. USA* 93:3346-3351.
O'Gorman, S. et al. (Mar. 15, 1991). "Recombinase-Mediated Gene Activation and Site-Specific Integration in Mammalian Cells," *Science* 251(4999):1351-1355.
Passini, M.A. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," *J. Virol.* 77(12):7034-7040.
Pechan, P. et al. (2009). "Novel Anti-VEGF Chimeric Molecules Delivered by AAV Vectors for Inhibition of Retinal Neovascularization," *Gene Ther.* 16:10-16.
Sarkar, R. (Feb. 15, 2004). "Total Correction of Hemophilia A Mice with Canine FVIII Using an AAV 8 Serotype," *Blood* 103(4):1253-1260.
Sauer, B. et al. (Jul. 1988). "Site-specific DNA recombination in mammalian cells by the Cre recombinase of bacteriophage P1," *Proc. Natl. Acad. Sci.* 85:5166-5170.
Schuck, P. et al. (Mar. 2000). "Size-Distribution Analysis of Macromolecules by Sedimentation Velocity Ultracentrifugation and Lamm Equation Modeling," *Biophys. J.* 78(3):1606-1619.
Sommer, J.M. et al. (Jan. 2003). "Quantification of Adeno-Associated Virus Particles and Empty Capsids by Optical Density Measurement," *Mol Ther.* 7(1):122-128.
Veldwijk, M.R. et al. (Aug. 2002). "Development and Optimization of a Real-Time Quantitative PCR-Based Method for the Titration of AAV-2 Vector Stocks" *Mol. Ther.* 6(2):272-278.
Wang, Y. et al. (1997). "Positive and Negative Regulation of Gene Expression in Eukaryotic Cells with an Inducible Transcriptional Regulator," *Gene Ther.* 4:432-441.
Wang, Y. et al. (Mar. 1997). "Ligand-Inducible and Liver-Specific Target Gene Expression in Transgenic Mice," *Nat. Biotech,* 15(3):239-243.
Wang, Z. et al. (2003). "Rapid and Highly Efficient Transduction by Double-Stranded Adeno-Associated Virus Vectors In Vitro and In Vivo," *Gene Ther* 10:2105-2111.
Wu, Z. et al. (Jan. 1, 2010). "Effect of Genome Size on AAV Vector Packaging," Molecular Therapy 18(1):80-86.

(56) References Cited

OTHER PUBLICATIONS

Xiao, X. et al. (1997). "Gene Transfer by Adeno-Associated Virus Vectors into the Central Nervous System," *Exp. Neurobiol.* 144:113-124.

Xiao, X. et al. (Mar. 1998). "Production of High-Titer Recombinant Adeno-Associated Virus Vectors in the Absence of Helper Adenovirus," *Journal of Virology* 72(3):2224-2232.

Yan, Z. et al. (Jun. 2015). "Optimization of Recombinant Adeno-Associated Virus-Mediated Expression for Large Transgenes, Using a Synthetic Promoter and Tandem Array Enhancers," *Human Gene Therapy* 26(6):334-346.

Yuan, Z. et al. (May 1, 2011) "A Versatile Adeno-Associated Virus Vector Producer Cell Line Method for Scalable Vector Production of Different Serotypes," *Human Gene Therapy* 22(5):613-624.

Zhong L. et al. (Jun. 3, 2008). "Next Generation of Adeno-Associated Virus 2 Vectors: Point Mutations in Tyrosines Lead to High-Efficiency Transduction at Lower Doses," *Proc Natl Acad Sci USA* 105(22):7827-7832.

GenBank Accession No. AAA53189, located at <https://www.ncbi.nlm.nih.gov/protein/AAA53189>, last visited on Nov. 20, 2017, 7 pages.

GenBank Accession No. NP_000483, located at < https://www.ncbi.nlm.nih.gov/protein/NP_000483>, last visited on Nov. 20, 2017, 7 pages.

GenBank Entrez Gene ID 1080, located at < https://www.ncbi.nlm.nih.gov/gene/?term=1080>, last visited on Nov. 20, 2017, 8 pages.

Niwa, H. et al. (1991). "Efficient Selection for High-Expression with a Novel Eukaryotic Vector," *Gene* 108:193-200.

Dong, B. et al. (Jan. 2010). "Characterization of Genome Integrity for Oversized Recombinant AAV Vector," Molecular Therapy 18(1):87-92.

Lai, Y. (Jan. 2010). "Evidence for the Failure of Adeno-Associated Virus Serotype 5 to Package a Viral Genome≥ 8.2 kb," Molecular Therapy 18(1):75-79.

Figure 1B:
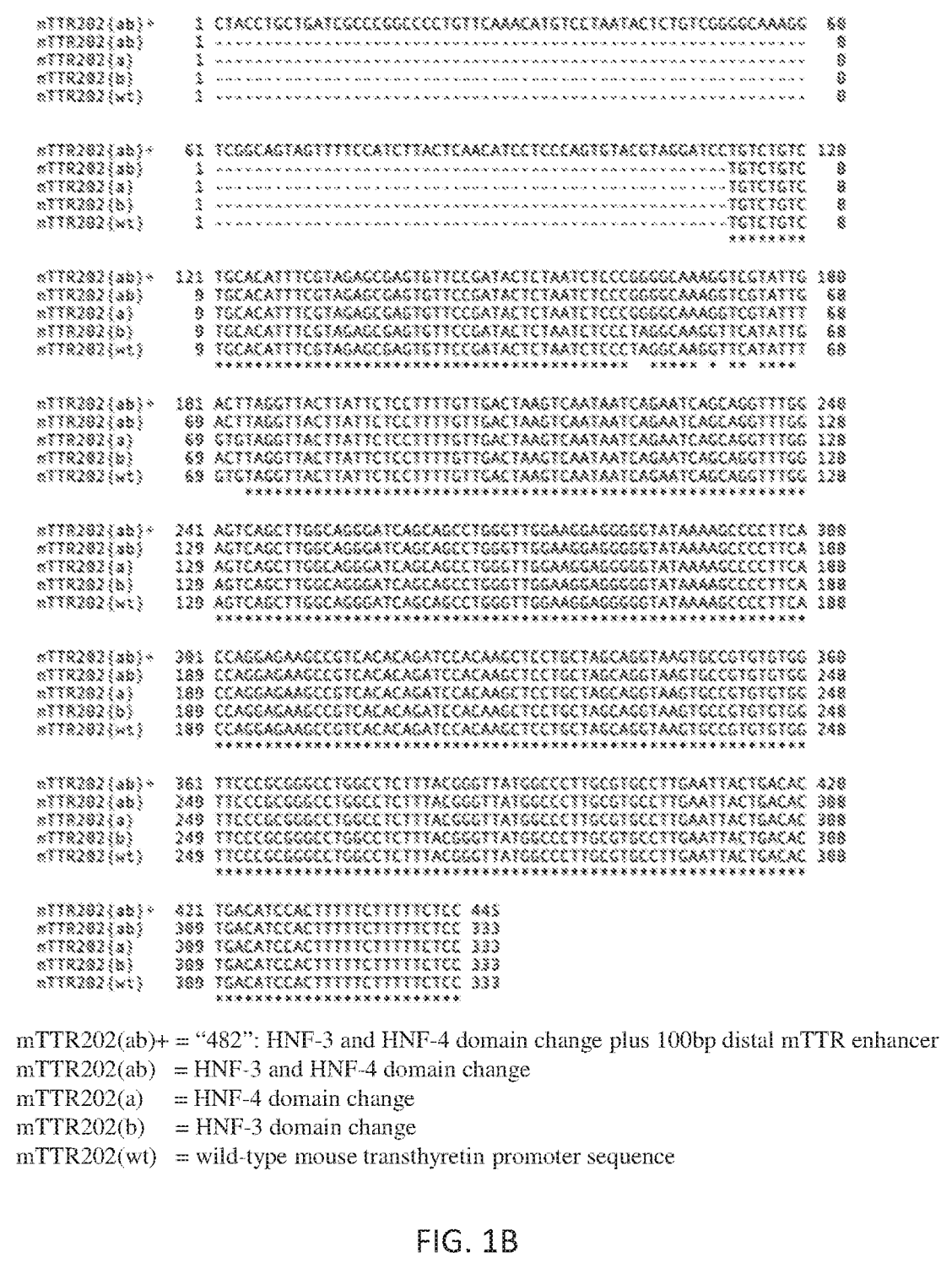

\* cited by examiner mTTR202(ab)+ = "482": HNF-3 and HNF-4 domain change plus 100bp distal mTTR enhancer
mTTR202(ab) = HNF-3 and HNF-4 domain change
mTTR202(a) = HNF-4 domain change
mTTR202(b) = HNF-3 domain change
mTTR202(wt) = wild-type mouse transthyretin promoter sequence

FIG. 1B 5.1 kb VG analysis

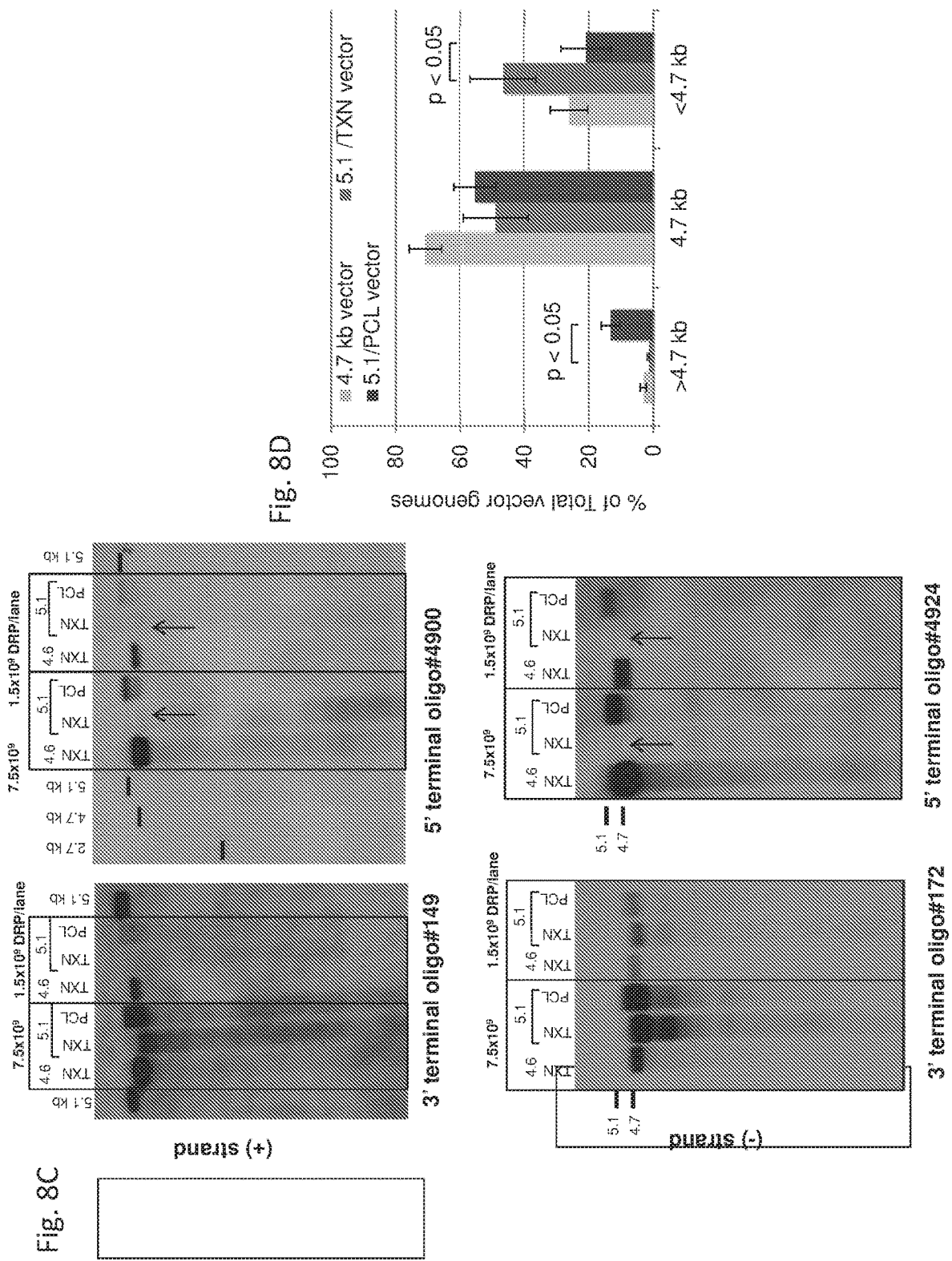

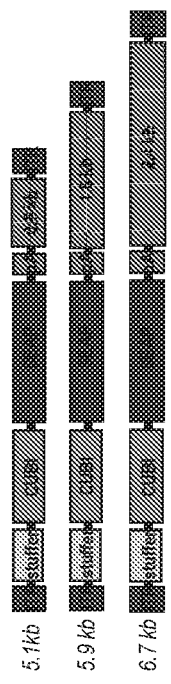
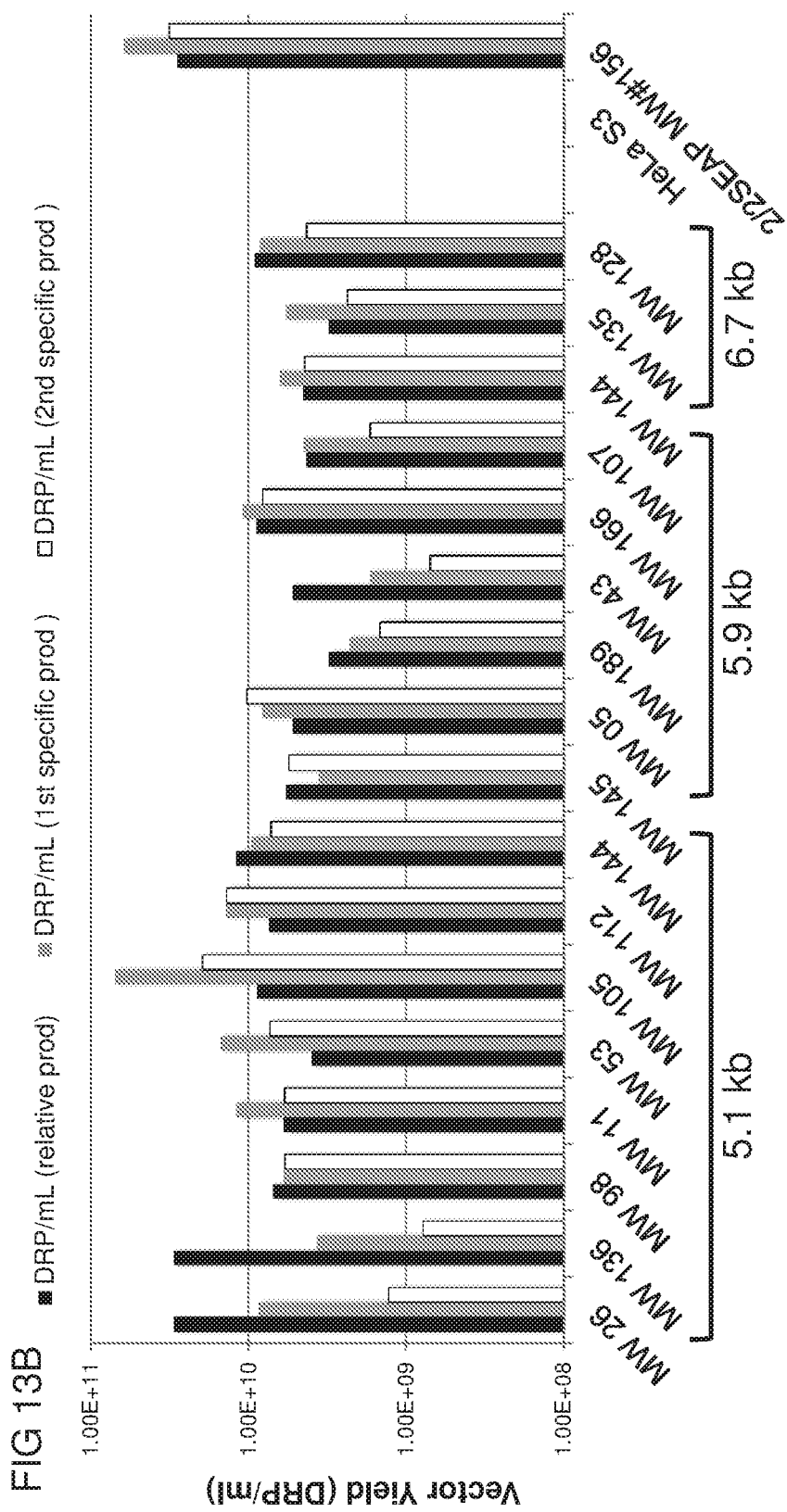
FIG. 13A
FIG 13B

SEQUENCE LISTING

<160> NUMBER OF SEQ ID NOS: 33

<210> SEQ ID NO 1
<211> LENGTH: 5097
<212> TYPE: DNA
<213> ORGANISM: Artificial Sequence
<220> FEATURE:
<223> OTHER INFORMATION: Synthetic Construct

<400> SEQUENCE: 1

```
gagctcttgg ccactccctc tctgcgcgct cgctcgctca ctgaggccgg gcgaccaaag    60
gtcgcccgac gcccgggctt tgcccgggcg gcctcagtga gcgagcgagc gcgcagagag   120
ggagtggcca actccatcac tagggggttcc tacgcgtgtc tgtctgcaca tttcgtagag   180
cgagtgttcc gatactctaa tctccctagg caaggttcat atttgtgtag gttacttatt   240 ctcctttgt tgactaagtc aataatcaga atcagcaggt ttggagtcag cttggcaggg    300
atcagcagcc tgggttggaa ggaggggggta taaaagcccc ttcaccagga gaagccgtca   360
cacagatcca caagctcctg ctagcaggta agtgccgtgt gtggttcccg cgggcctggc   420
ctctttacgg gttatggccc ttgcgtgcct tgaattactg acactgacat ccactttttc   480
tttttctcca caggtatcga ttctctagag ccaccatgca gatcgagctg tctacctgct   540
tcttcctgtg cctgctgcgg ttctgcttca gcgccaccag acgtactat ctgggcgccg    600 tggaactgag ctgggactac atgcagagcg acctgggcga gctgcccgtg gatgccagat   660
tccctccaag agtgcccaag agcttcccct caacacctc cgtggtgtac aagaaaccc     720 tgttcgtgga attcaccgac cacctgttca atatcgccaa gcccagaccc ccctggatgg   780
gcctgctggg acctacaatt caggccgagg tgtacgacac cgtcgtgatc accctgaaga   840
acatggccag ccaccccgtg tctctgcatg ccgtgggagt gtcctactgg aaggcctctg   900
agggcgccga gtacgacgat cagaccagcc agcgcgagaa agaggacgac aaggtgttcc   960
ctggcggcag ccacacctac gtgtggcagg tgctgaaaga aaacggcccc atggcctccg  1020
accctctgtg cctgacatac agctacctga gccacgtgga cctcgtgaag gacctgaaca  1080
gcggcctgat cggagccctg ctcgtgtgta gagagggcag cctggccaaa gagaaaaccc  1140
agaccctgca caagttcatc ctgctgttcg ccgtgttcga cgagggcaag agctggcaca  1200
gcgagacaaa gaacagcctg atgcaggacc gggacgccgc ctctgctaga gcctggccca  1260
aaatgcacac cgtgaacggc tacgtgaaca agagcctgcc cggactgatc ggctgccacc  1320
ggaagtctgt gtactggcac gtgatcggca tgggcaccac ccctgaggtg cacagcatct  1380
ttctggaagg acacacccttt ctcgtgcgga accaccggca ggccagcctg gaaatcagcc  1440
ctatcacctt cctgaccgcc cagacactgc tgatggacct gggccagttt ctgctgttct  1500
gccacatcag ctcccaccag cacgacggca tggaagccta cgtgaaggtg gacagctgcc  1560
ccgaggaacc ccagctgcgg atgaagaaca acgaggaagc cgaggactac gacgacgacc  1620
tgaccgacag cgagatggac gtggtgcgct tcgacgacga taacagcccc agcttcatcc  1680
agatcagaag cgtggccaag aagcacccca gacctgggt gcactatatc gccgccgagg  1740
aagaggactg ggattacgcc cctctggtgc tggcccccga cgacagaagc tacaagagcc  1800
agtacctgaa caatggcccc cagcggatcg gccggaagta taagaaagtg cggttcatgg  1860
cctacaccga cgagacattc aagaccagag aggccatcca gcacgagagc ggcatcctgg  1920
gccctctgct gtatgcgaa gtgggcgaca ccctgctgat catcttcaag aaccaggcca  1980 gcagaccta caacatctac cctcacggca tcaccgacgt gcggcccctg tactccagaa  2040
```

```
ggctgcccaa gggcgtgaaa cacctgaagg acttccccat cctgcccggc gagatcttca    2100
agtacaagtg gaccgtgacc gtggaagatg ccccaccaa gagcgacccc agatgcctga    2160
cacggtacta cagcagcttc gtgaacatgg aacgggacct ggcctccggc ctgattggcc    2220
cactgctgat ctgctacaaa gaaagcgtgg accagcgggg caaccagatc atgagcgaca    2280
agcggaacgt gatcctgttt agcgtgttcg atgagaaccg gtcctggtat ctgaccgaga    2340
atatccagcg gttcctgccc aaccctgccg gcgtgcagct ggaagatcct gagttccagg    2400
cctccaacat catgcactcc atcaatggct atgtgttcga cagcctgcag ctgagcgtgt    2460
gcctgcacga ggtggcctac tggtacatcc tgagcatcgg ggcccagacc gacttcctgt    2520
ccgtgttctt ctccggctac accttcaagc acaagatggt gtacgaggat accctgaccc    2580
tgttcccctt tagcggcgaa accgtgttca tgagcatgga aaaccccggc ctgtggatcc    2640
tgggctgcca caacagcgac ttccggaaca gaggcatgac cgccctgctg aaggtgtcca    2700
gctgcgacaa gaacaccggc gactactacg aggacagcta tgaggacatc agcgcctacc    2760
tgctgagcaa gaacaatgcc atcgagccca aagcttcag ccagaacccc ccgtgctga    2820
agcggcacca gagagagatc acccggacca ccctgcagtc cgaccaggaa gagatcgatt    2880
acgacgacac catcagcgtg gaaatgaaga agaagatt cgacatctac gacgaggacg    2940
agaaccagag ccccggtcc tttcagaaaa agacccggca ctacttcatt gccgctgtgg    3000
aacggctgtg ggactacggc atgagcagca gccctcacgt gctgagaaac agggcccaga    3060
gcggcagcgt gccccagttc aagaaagtgg tgttccagga attcacagac ggcagcttca    3120
cccagcctct gtaccgcggc gagctgaatg agcacctggg actgctgggc ccctatatca    3180
gagccgaagt ggaagataat atcatggtca ccttccggaa tcaggcctcc cggccctaca    3240
gcttctacag ctccctgatc agctacgaag aggaccagag acagggcgct gagccccgga    3300
agaacttcgt gaagcccaac gagactaaga cctacttttg gaaggtgcag caccacatgg    3360
cccctacaaa ggacgagttc gactgcaagg cctgggccta cttctccgat gtggacctgg    3420
aaaaggacgt gcactctggg ctgatcggcc ccctgctcgt gtgccacacc aacaccctga    3480
atcccgccca cggcagacaa gtgacagtgc aggaattcgc cctgttcttc accatcttcg    3540
acgaaacaaa gagctggtac ttcaccgaaa acatggaaag aaactgccgg gctccctgca    3600
acatccagat ggaagatccc accttcaaag agaactaccg gttccacgcc atcaacggct    3660
acatcatgga cacactgccc ggcctcgtga tggctcagga tcagcggatc cggtggtatc    3720
tgctgtccat gggctccaac gagaacatcc acagcatcca cttcagcggc cacgtgttca    3780
ccgtgcggaa aaaagaagag tacaaaatgg ccctgtacaa cctgtaccct ggggtgttcg    3840
agacagtgga aatgctgccc agcaaggcgc gcatctggcg ggtggaatgt ctgatcggcg    3900
agcatctgca cgctgggatg agcacactgt ttctggtgta cagcaacaag tgccagacac    3960
ctctgggcat ggcctctggc acatccggg actttcagat cacagccagc ggccagtatg    4020
gccagtgggc cccaaaactg ccagactgc actacagcgg cagcatcaac gcctggtcca    4080
ccaaagagcc cttcagctgg atcaaggtgg acctgctggc tcccatgatc atccacggaa    4140
tcaagaccca gggcgccaga cagaagttca gcagcctgta catcagccag ttcatcatca    4200
tgtacagcct ggacggcaag aagtggcaga cctaccgggg caatagcacc ggcaccctga    4260
tggtgttctt cggcaacgtg gactccagcg gcattaagca acatcttc aacccccca    4320
tcattgcccg gtacatccgg ctgcacccca cccactacag catccggtcc accctgagaa    4380
```

```
tggaactgat gggctgcgac ctgaactcct gcagcatgcc cctggggatg gaaagcaagg    4440
ccatctccga cgcccagatc accgcctcca gctacttcac caacatgttc gccacctggt    4500
ccccatccaa ggcccggctg catctgcagg gcagaagcaa tgcttggagg ccccaagtga    4560
acaaccccaa agaatggctg caggtggact tccagaaaac catgaaagtg accggcgtga    4620
ccacccaggg cgtgaagtct ctgctgacct ctatgtacgt gaaagagttc ctgatctcca    4680
gcagccagga cggccaccag tggaccctgt ttttccagaa cggcaaagtg aaagtgtttc    4740
aggggaacca ggactccttc acccccgtcg tgaatagcct ggaccctcca ctgctgacca    4800
gatacctgcg gatccaccct cagagttggg tgcaccagat tgctctgcgg atggaagtgc    4860
tgggatgcga ggcccaggac ctgtactgac actagtaata aaagatcaga gctgtagaga    4920
tctgtgtgtt ggttttttgt gtgcggccgg taccaggaac ccctagtgat ggagttggcc    4980
actccctctc tgcgcgctcg ctcgctcact gaggccgggc gaccaaaggt cgcccgacgc    5040
ccgggctttg cccgggcggc ctcagtgagc gagcgagcgc gcagagaggg agtggcc      5097

<210> SEQ ID NO 2
<211> LENGTH: 229
<212> TYPE: DNA
<213> ORGANISM: Artificial Sequence
<220> FEATURE:
<223> OTHER INFORMATION: Synthetic Construct

<400> SEQUENCE: 2
tgtctgtctg cacatttcgt agagcgagtg ttccgatact ctaatctccc ggggcaaagg      60
tcgtattgac ttaggttact tattctcctt ttgttgacta agtcaataat cagaatcagc     120
aggtttggag tcagcttggc agggatcagc agcctgggtt ggaaggaggg ggtataaaag     180
ccccttcacc aggagaagcc gtcacacaga tccacaagct cctgctagc                229

<210> SEQ ID NO 3
<211> LENGTH: 341
<212> TYPE: DNA
<213> ORGANISM: Artificial Sequence
<220> FEATURE:
<223> OTHER INFORMATION: Synthetic Construct

<400> SEQUENCE: 3
ctacctgctg atcgcccggc ccctgttcaa acatgtccta atactctgtc ggggcaaagg      60
tcggcagtag ttttccatct tactcaacat cctcccagtg tacgtaggat cctgtctgtc     120
tgcacatttc gtagagcgag tgttccgata ctctaatctc cggggcaaa ggtcgtattg     180 acttaggtta cttattctcc ttttgttgac taagtcaata atcagaatca gcaggtttgg     240
agtcagcttg gcagggatca gcagcctggg ttggaaggag ggggtataaa agccccttca     300
ccaggagaag ccgtcacaca gatccacaag ctcctgctag c                         341

<210> SEQ ID NO 4
<211> LENGTH: 13524
<212> TYPE: DNA
<213> ORGANISM: Artificial Sequence
<220> FEATURE:
<223> OTHER INFORMATION: Synthetic Construct

<400> SEQUENCE: 4
gaatgcaatt gttgttgtta acttgtttat tgcagcttat aatggttaca ataaagcaa       60 tagcatcaca aatttcacaa ataaagcatt ttttcactg cattctagtt gtggtttgtc      120
caaactcatc aatgtatctt atcatgtctg gatccgctag aactaggaat tcgctagcgg     180
```

```
taccgatatc ctagtggatc ccccgtacac aggaagtgac aattttcgcg cggttttagg    240
cggatgttgt agtaaatttg ggcgtaaccg agtaagattt gggtggtcac gctgggtatt    300
taagcccgag tgagcacgca gggtctccat tttgaagcgg gaggtttgaa cgcgcagccg    360
ccatgccggg gttttacgag attgtgatta aggtccccag cgaccttgac gagcatctgc    420
ccggcatttc tgacagcttt gtgaactggg tggccgagaa ggaatgggag ttgccgccag    480
attctgacat ggatctgaat ctgattgagc aggcacccct gaccgtggcc gagaagctgc    540
agcgcgactt tctgacggaa tggcgccgtg tgagtaaggc cccggaggcc cttttctttg    600
tgcaatttga gaagggagag agctacttcc acatgcacgt gctcgtggaa accaccgggg    660
tgaaatccat ggttttggga cgtttcctga gtcagattcg cgaaaaactg attcagagaa    720
tttaccgcgg gatcgagccg actttgccaa actggttcgc ggtcacaaag accagaaatg    780
gcgccggagg cgggaacaag gtggtggatg agtgctacat ccccaattac ttgctcccca    840
aaacccagcc tgagctccag tgggcgtgga ctaatatgga acagtattta agcgcctgtt    900
tgaatctcac ggagcgtaaa cggttggtgg cgcagcatct gacgcacgtg tcgcagacgc    960
aggagcagaa caaagagaat cagaatccca attctgatgc gccggtgatc agatcaaaaa   1020
cttcagccag gtacatggag ctggtcgggt ggctcgtgga caagggggatt acctcggaga   1080 agcagtggat ccaggaggac caggcctcat acatctcctt caatgcggcc tccaactcgc   1140
ggtcccaaat caaggctgcc ttggacaatg cgggaaagat tatgagcctg actaaaaccg   1200
cccccgacta cctggtgggc cagcagcccg tggaggacat ttccagcaat cggatttata   1260
aaattttgga actaaacggg tacgatcccc aatatgcggc ttccgtcttt ctgggatggg   1320
ccacgaaaaa gttcggcaag aggaacacca tctggctgtt tgggcctgca actaccggga   1380
agaccaacat cgcggaggcc atagcccaca ctgtgcccct tacgggtgc gtaaactgga   1440 ccaatgagaa ctttcccttc aacgactgtg tcgacaagat ggtgatctgg tgggaggagg   1500
ggaagatgac cgccaaggtc gtggagtcgg ccaaagccat tctcggagga agcaaggtgc   1560
gcgtggacca gaaatgcaag tcctcggccc agatagaccc gactcccgtg atcgtcacct   1620
ccaacaccaa catgtgcgcc gtgattgacg ggaactcaac gaccttcgaa caccagcagc   1680
cgttgcaaga ccggatgttc aaatttgaac tcacccgccg tctggatcat gactttggga   1740
aggtcaccaa gcaggaagtc aaagactttt tccggtgggc aaaggatcac gtggttgagg   1800
tggagcatga attctacgtc aaaaagggtg gagccaagaa aagacccgcc cccagtgacg   1860
cagatataag tgagcccaaa cgggtgcgcg agtcagttgc gcagccatcg acgtcagacg   1920
cggaagcttc gatcaactac gcagacaggt accaaaacaa atgttctcgt cacgtgggca   1980
tgaatctgat gctgtttccc tgcagacaat gcgagagaat gaatcagaat tcaaatatct   2040
gcttcactca cggacagaaa gactgtttag agtgctttcc cgtgtcagaa tctcaacccg   2100
tttctgtcgt caaaaaggcg tatcagaaac tgtgctacat tcatcatatc atgggaaagg   2160
tgccagacgc ttgcactgcc tgcgatctgg tcaatgtgga tttggatgac tgcatctttg   2220
aacaataaat gatttaaatc aggtatggct gccgatggtt atcttccaga ttggctcgag   2280
gacaacctct ctgagggcat tcgcgagtgg tgggacctga aacctggagc cccgaaaccc   2340
aaagccaacc agcaaaagca ggacgacggc cggggtctgg tgcttcctgg ctacaagtac   2400
ctcggaccct tcaacggact cgacaagggg gagcccgtca cgcgcggcga cgcagcggcc   2460
ctcgagcacg acaaggccta cgaccagcag ctcaaagcgg gtgacaatcc gtacctgcgg   2520
```

```
tataaccacg ccgacgccga gtttcaggag cgtctgcaag aagatacgtc tttgggggc     2580
aacctcgggc gagcagtctt ccaggccaag aagcgggttc tcgaacctct cggtctggtt     2640
gaggaaggcg ctaagacggc tcctggaaag aagagaccgg tagagcagtc accccaagaa     2700
ccagactcat cctcgggcat cggcaaatca ggccagcagc ccgctaaaaa gagactcaat     2760
tttggtcaga ctggcgactc agagtcagtc cccgacccac aacctctcgg agaacctcca     2820
gaagcccct caggtctggg acctaataca atggcttcag gcggtggcgc tccaatggca      2880
gacaataacg aaggcgccga cggagtgggt aattcctcgg gaaattggca ttgcgattcc     2940
acatggctgg gggacagagt catcaccacc agcacccgaa cctgggcatt gcccacctac     3000
aacaaccacc tctacaagca aatctccaat ggaacatcgg gaggaagcac caacgacaac     3060
acctactttg gctacagcac cccctggggg tattttgact tcaacagatt ccactgccac     3120
ttctcaccac gtgactggca gcgactcatc aacaacaact ggggattccg gccaaagaga     3180
ctcaacttca gctgttcaa catccaggtc aaggaggtta cgacgaacga aggcaccaag     3240
accatcgcca ataaccttac cagcaccgtc caggtcttta cggactcgga gtaccagcta     3300
ccgtacgtcc taggctctgc ccaccaagga tgcctgccac cgtttcctgc agacgtcttc     3360
atggttcctc agtacggcta cctgacgctc aacaatggaa gtcaagcgtt aggacgttct     3420
tcttctact gtctggaata cttcccttct cagatgctga gaaccggcaa caactttcag     3480
ttcagctaca ctttcgagga cgtgcctttc cacagcagct acgcacacag ccagagtcta     3540
gatcgactga tgaacccct catcgaccag tacctatact acctggtcag aacacagaca     3600
actgaaactg ggggaactca aactttggca ttcagccaag caggccctag ctcaatggcc     3660
aatcaggcta gaaactgggt acccgggcct tgctaccgtc agcagcgcgt ctccacaacc     3720
accaaccaaa ataacaacag caactttgcg tggacgggga ctgctaaatt caagctgaac     3780
gggagagact cgctaatgaa tcctggcgtg gctatggcat cgcacaaaga cgacgaggac     3840
cgcttctttc catcaagtgg cgttctcata tttggcaagc aaggagccgg gaacgatgga     3900
gtcgactaca gccaggtgct gattacagat gaggaagaaa ttaaagccac caaccctgta     3960
gccacagagg aatacggagc agtggccatc aacaaccagg ccgctaacac gcaggcgcaa     4020
actggacttg tgcataacca gggagttatt cctggtatgg tctggcagaa ccggacgtg     4080
tacctgcagg gccctatttg ggctaaaata cctcacacag atggcaactt tcacccgtct     4140
cctctgatgg gtggatttgg actgaaacac ccacctccac agattctaat taaaaataca     4200
ccagtgccgg cagatcctcc tcttaccttc aatcaagcca agctgaactc tttcatcacg     4260
cagtacagca cgggacaagt cagcgtggaa atcgagtggg agctgcagaa agaaaacagc     4320
aagcgctgga atccagagat ccagtatact tcaaactact acaaatctac aaatgtggac     4380
tttgctgtca ataccgaagg tgtttactct gagcctcgcc ccattggtac tcgttacctc     4440
acccgtaatt tgtaattgcc tgttaatcaa taaaccggtt aattcgtttc agttgaactt     4500
tggtctctgc gggccggcct taattaacat gtgagcaaaa ggccagcaaa aggccaggaa     4560
ccgtaaaaag gccgcgttgc tggcgttttt ccataggctc cgcccccctg acgagcatca     4620
caaaaatcga cgctcaagtc agaggtggcg aaacccgaca ggactataaa gataccaggc     4680
gtttccccct ggaagctccc tcgtgcgctc tcctgttccg accctgccgc ttaccggata     4740
cctgtccgcc tttctccctt cgggaagcgt ggcgctttct catagctcac gctgtaggta     4800
tctcagttcg gtgtaggtcg ttcgctccaa gctgggctgt gtgcacgaac cccccgttca     4860
gcccgaccgc tgcgccttat ccggtaacta tcgtcttgag tccaacccgg taagcacga     4920
```

```
cttatcgcca ctggcagtag ccactggtaa caggattagc agagcgaggt atgtaggcgg   4980
tgctacagag ttcttgaagt ggtggcctaa ctacggctac actagaagaa cagtatttgg   5040
tatctgcgct ctgctgaagc cagttacctt cggaaaaaga gttggtagct cttgatccgg   5100
caaacaaacc accgctggta gcggtggttt ttttgtttgc aagcagcaga ttacgcgcag   5160
aaaaaaagga tctcaagaag atcctttgat cttttctacg gggtctgacg ctcagtggaa   5220
cgaaaactca cgttaaggga ttttggtcat gagattatca aaaaggatct tcacctagat   5280
ccttttcacg tagaaagcca gtccgcagaa acggtgctga ccccggatga atgtcagcta   5340
ctgggctatc tggacaaggg aaaacgcaag cgcaaagaga agcaggtag cttgcagtgg   5400 gcttacatgg cgatagctag actgggcggt tttatggaca gcaagcgaac cggaattgcc   5460
agctggggcg ccctctggta aggttgggaa gccctgcaaa gtaaactgga tgctttctt   5520 gccgccaagg atctgatggc gcaggggatc aagatccgat caagagacag gatgaggatc   5580
gtttcgcatg attgaacaag atggattgca cgcaggttct ccggccgctt gggtggagag   5640
gctattcggc tatgactggg cacaacagac aatcggctgc tctgatgccg ccgtgttccg   5700
gctgtcagcg caggggcgcc tggttctttt tgtcaagacc gacctgtccg gtgccctgaa   5760
tgaactgcaa gacgaggcag cgcggctatc gtggctggcc acgacgggcg ttccttgcgc   5820
agctgtgctc gacgttgtca ctgaagcggg aagggactgg ctgctattgg gcgaagtgcc   5880
ggggcaggat ctcctgtcat ctcaccttgc tcctgccgag aaagtatcca tcatggctga   5940
tgcaatgcgg cggctgcata cgcttgatcc ggctacctgc ccattcgacc accaagcgaa   6000
acatcgcatc gagcgagcac gtactcggat ggaagccggt cttgtcgatc aggatgatct   6060
ggacgaagag catcagggc tcgcgccagc cgaactgttc gccaggctca aggcgagcat   6120
gcccgacggc gaggatctcg tcgtgaccca tggcgatgcc tgcttgccga atatcatggt   6180
ggaaaatggc cgcttttctg gattcatcga ctgtggccgg ctgggtgtgg cggaccgcta   6240
tcaggacata gcgttggcta cccgtgatat tgctgaagag cttggcggcg aatgggctga   6300
ccgcttcctc gtgctttacg gtatcgccgc tcccgattcg cagcgcatcg ccttctatcg   6360
ccttcttgac gagttcttct gaattaatta gcggccgct catgagcgga tacatatttg   6420
aatgtattta gaaaaataaa caaataggg ttccgcgcac atttccccga aaagtgccac   6480
ctgacgtcag atccggtgcg ggcctcttcg ctattacgcc agctggcgaa aggggatgt   6540 gctgcaaggc gattaagttg ggtaacgcca gggttttccc agtcacgacg ttgtaaaacg   6600
acggccagtg aattcgcgag ctcttggcca ctccctctct gcgcgctcgc tcgctcactg   6660
aggccgggcg accaaaggtc gcccgacgcc cgggctttgc ccgggcggcc tcagtgagcg   6720
agcgagcgcg cagagaggga gtggccaact ccatcactag ggttcctac gcgtgtctgt   6780 ctgcacattt cgtagagcga gtgttccgat actctaatct ccctaggcaa ggttcatatt   6840
tgtgtaggtt acttattctc ctttttgttga ctaagtcaat aatcagaatc agcaggtttg   6900
gagtcagctt ggcagggatc agcagcctgg gttggaagga gggggtataa aagccccttc   6960
accaggagaa gccgtcacac agatccacaa gctcctgcta gcaggtaagt gccgtgtgtg   7020
gttcccgcgg gcctggcctc tttacgggtt atggcccttg cgtgccttga attactgaca   7080
ctgacatcca cttttctttt tctccacag gtatcgattc tctagagcca ccatgcagat   7140
cgagctgtct acctgcttct tcctgtgcct gctgcggttc tgcttcagcg ccaccagacg   7200
gtactatctg ggcgccgtgg aactgagctg ggactacatg cagagcgacc tgggcgagct   7260
```

```
gcccgtggat gccagattcc ctccaagagt gcccaagagc ttccccttca acacctccgt   7320
ggtgtacaag aaaaccctgt tcgtggaatt caccgaccac ctgttcaata tcgccaagcc   7380 cagaccccc  tggatgggcc tgctgggacc tacaattcag gccgaggtgt acgacaccgt   7440
cgtgatcacc ctgaagaaca tggccagcca ccccgtgtct ctgcatgccg tgggagtgtc   7500
ctactggaag gcctctgagg gcgccgagta cgacgatcag accagccagc gcgagaaaga   7560
ggacgacaag gtgttccctg gcggcagcca cacctacgtg tggcaggtgc tgaaagaaaa   7620
cggccccatg gcctccgacc ctctgtgcct gacatacagc tacctgagcc acgtggacct   7680
cgtgaaggac ctgaacagcg gcctgatcgg agccctgctc gtgtgtagag agggcagcct   7740
ggccaaagag aaaacccaga ccctgcacaa gttcatcctg ctgttcgccg tgttcgacga   7800
gggcaagagc tggcacagcg agacaaagaa cagcctgatg caggaccggg acgccgcctc   7860
tgctagagcc tggcccaaaa tgcacaccgt gaacggctac gtgaacagaa gcctgcccgg   7920
actgatcggc tgccaccgga agtctgtgta ctggcacgtg atcggcatgg gcaccacccc   7980
tgaggtgcac agcatctttc tggaaggaca cctttctc gtgcggaacc accggcaggc    8040
cagcctggaa atcagcccta tcaccttcct gaccgcccag acactgctga tggacctggg   8100
ccagtttctg ctgttctgcc acatcagctc ccaccagcac gacggcatgg aagcctacgt   8160
gaaggtggac agctgccccg aggaacccca gctgcggatg aagaacaacg aggaagccga   8220
ggactacgac gacgacctga ccgacagcga gatggacgtg gtgcgcttcg acgacgataa   8280
cagccccagc ttcatccaga tcagaagcgt ggccaagaag caccccaaga cctgggtgca   8340
ctatatcgcc gccgaggaag aggactggga ttacgcccct ctggtgctgg cccccgacga   8400
cagaagctac aagagccagt acctgaacaa tggcccccag cggatcggcc ggaagtataa   8460
gaaagtgcgc ttcatggcct acaccgacga gacattcaag accagagagg ccatccagca   8520
cgagagcggc atcctgggcc ctctgctgta tggcgaagtg ggcgacaccc tgctgatcat   8580
cttcaagaac caggccagca gaccctacaa catctaccct cacggcatca ccgacgtgcg   8640
gcccctgtac tccagaaggc tgcccaaggg cgtgaaacac ctgaaggact tccccatcct   8700
gcccggcgag atcttcaagt acaagtggac cgtgaccgtg aagatggcc ccaccaagag    8760 cgaccccaga tgcctgacac ggtactacag cagcttcgtg aacatggaac gggacctggc   8820
ctccggcctg attggcccac tgctgatctg ctacaaagaa agcgtggacc agcggggcaa   8880
ccagatcatg agcgacaagc ggaacgtgat cctgtttagc gtgttcgatg agaaccggtc   8940
ctggtatctg accgagaata tccagcggtt cctgcccaac cctgccggcg tgcagctgga   9000
agatcctgag ttccaggcct ccaacatcat gcactccatc aatggctatg tgttcgacag   9060
cctgcagctg agcgtgtgcc tgcacgaggt ggcctactgg tacatcctga gcatcggggc   9120
ccagaccgac ttcctgtccg tgttcttctc cggctacacc ttcaagcaca agatggtgta   9180
cgaggatacc ctgaccctgt tccccttag cggcgaaacc gtgttcatga gcatggaaaa   9240
ccccggcctg tggatcctgg ctgccacaa cagcgacttc cggaacagag gcatgaccgc   9300
cctgctgaag gtgtccagct gcgacaagaa caccggcgac tactacgagg acagctatga   9360
ggacatcagc gcctacctgc tgagcaagaa caatgccatc gagcccagaa gcttcagcca   9420
gaaccccccc gtgctgaagc ggcaccagag agagatcacc cggaccaccc tgcagtccga   9480
ccaggaagag atcgattacg acgacaccat cagcgtggaa atgaagaaag aagatttcga   9540
catctacgac gaggacgaga accagagccc ccggtccttt cagaaaaaga cccggcacta   9600
cttcattgcc gctgtggaac ggctgtggga ctacggcatg agcagcagcc ctcacgtgct   9660
```

```
gagaaacagg gcccagagcg gcagcgtgcc ccagttcaag aaagtggtgt tccaggaatt    9720
cacagacggc agcttcaccc agcctctgta ccgcggcgag ctgaatgagc acctgggact    9780
gctgggcccc tatatcagag ccgaagtgga agataatatc atggtcacct tccggaatca    9840
ggcctcccgg ccctacagct tctacagctc cctgatcagc tacgaagagg accagagaca    9900
gggcgctgag ccccggaaga acttcgtgaa gcccaacgag actaagacct acttttggaa    9960
ggtgcagcac cacatggccc ctacaaagga cgagttcgac tgcaaggcct gggcctactt   10020
ctccgatgtg gacctggaaa aggacgtgca ctctgggctg atcggccccc tgctcgtgtg   10080
ccacaccaac accctgaatc ccgcccacgg cagacaagtg acagtgcagg aattcgccct   10140
gttcttcacc atcttcgacg aaacaaagag ctggtacttc accgaaaaca tggaaagaaa   10200
ctgccgggct ccctgcaaca tccagatgga agatcccacc ttcaaagaga actaccggtt   10260
ccacgccatc aacggctaca tcatggacac actgcccggc ctcgtgatgg ctcaggatca   10320
gcggatccgg tggtatctgc tgtccatggg ctccaacgag aacatccaca gcatccactt   10380
cagcggccac gtgttcaccg tgcggaaaaa agaagagtac aaaatggccc tgtacaacct   10440
gtaccctggg gtgttcgaga cagtggaaat gctgcccagc aaggccggca tctggcgggt   10500
ggaatgtctg atcggcgagc atctgcacgc tgggatgagc acactgtttc tggtgtacag   10560
caacaagtgc cagacacctc tgggcatggc ctctggccac atccgggact ttcagatcac   10620
agccagcggc cagtatggcc agtgggcccc aaaactggcc agactgcact acagcggcag   10680
catcaacgcc tggtccacca agagcccctt cagctggatc aaggtggacc tgctggctcc   10740
catgatcatc cacggaatca agacccaggg cgccagacag aagttcagca gcctgtacat   10800
cagccagttc atcatcatgt acagcctgga cggcaagaag tggcagacct accggggcaa   10860
tagcaccggc accctgatgg tgttcttcgg caacgtggac tccagcggca ttaagcacaa   10920
catcttcaac ccccccatca ttgcccggta catccggctg cacccccacc actacagcat   10980
ccggtccacc ctgagaatgg aactgatggg ctgcgacctg aactcctgca gcatgcccct   11040
ggggatggaa agcaaggcca tctccgacgc ccagatcacc gcctcagct acttcaccaa   11100 catgttcgcc acctggtccc catccaaggc ccggctgcat ctgcagggca gaagcaatgc   11160
ttggaggccc caagtgaaca cccccaaaga atggctgcag gtggacttcc agaaaaccat   11220
gaaagtgacc ggcgtgacca cccagggcgt gaagtctctg ctgacctcta tgtacgtgaa   11280
agagttcctg atctccagca gccaggacgg ccaccagtgg accctgtttt tccagaacgg   11340
caaagtgaaa gtgtttcagg ggaaccagga ctccttcacc cccgtcgtga atagcctgga   11400
ccctccactg ctgaccagat acctgcggat ccaccctcag agttgggtgc accagattgc   11460
tctgcggatg gaagtgctgg gatgcgaggc ccaggacctg tactgacaac tagtaataaa   11520
agatcagagc tgtagagatc tgtgtgttgg ttttttgtgt gcggccggta cccaggaacc   11580
cctagtgatg gagttggcca ctccctctct gcgcgctcgc tcgctcactg aggccgggcg   11640
accaaaggtc gcccgacgcc cgggctttgg tcggcggcc tcagtgagcg agcgagcgcg   11700
cagagaggga gtggcggaa gcttggcgta atcatggtca tagctgtttc ctgtgtgaaa   11760
ttgttatccg ctcacaattc cacacaacat acgagccgga agcataaagt gtaaagcctg   11820
gggtgcctaa tgagtgagct aactcacatt aattgcgttg cgctcactgc ccgctttcca   11880
gtcgggaaac ctgtcgtgcc agctgcatta atgaatcggc caacgcgcgg ggagaggcgg   11940
tttgcgtatt gggcgctctt ccgctgatct catactagcg aacgccagca agacgtagcc   12000
```

| | |
|---|---|
| cagcgcgtcg gccccgagat gcgccgcgtg cggctgctgg agatggcgga cgcgatggat | 12060 |
| atgttctgcc aagggttggt ttgcgcattc acagttctcc gcaagaattg attggctcca | 12120 |
| attcttggag tggtgaatcc gttagcgagg tgccgccctg cttcatcccc gtggcccgtt | 12180 |
| gctcgcgttt gctggcggtg tccccggaag aaatatattt gcatgtcttt agttctatga | 12240 |
| tgacacaaac cccgcccagc gtcttgtcat tggcgaattc cggctgtgga atgtgtgtca | 12300 |
| gttagggtgt ggaaagtccc caggctcccc agcaggcaga agtatgcaaa gcatgcatct | 12360 |
| caattagtca gcaaccaggt gtggaaagtc cccaggctcc ccagcaggca gaagtatgca | 12420 |
| aagcatgcat ctcaattagt cagcaaccat agtcccgccc ctaactccgc ccatcccgcc | 12480 |
| cctaactccg cccagttccg cccattctcc gccccatggc tgactaattt tttttattta | 12540 |
| tgcagaggcc gaggccgcct cggcctctga gctattccag aagtagtgag gaggcttttt | 12600 |
| tggaggccta ggcttttgca aaaagcttgc atgcctgcag gtcggccgcc acgaccggtg | 12660 |
| ccgccaccat cccctgaccc acgccccctga ccccctcacaa ggagacgacc ttccatgacc | 12720 |
| gagtacaagc ccacggtgcg cctcgccacc cgcgacgacg tcccccgggc cgtacgcacc | 12780 |
| ctcgccgccg cgttcgccga ctaccccgcc acgcgccaca ccgtcgaccc ggaccgccac | 12840 |
| atcgagcggg tcaccgagct gcaagaactc ttcctcacgc gcgtcgggct cgacatcggc | 12900 |
| aaggtgtggg tcgcggacga cggcgccgcg gtggcggtct ggaccacgcc ggagagcgtc | 12960 |
| gaagcggggg cggtgttcgc cgagatcggc ccgcgcatgg ccgagttgag cggttcccgg | 13020 |
| ctggccgcgc agcaacagat ggaaggcctc ctggcgccgc accggcccaa ggagcccgcg | 13080 |
| tggttcctgg ccaccgtcgg cgtctcgccc gaccaccagg gcaagggtct gggcagcgcc | 13140 |
| gtcgtgctcc ccggagtgga ggcggccgag cgcgccgggg tgcccgcctt cctggagacc | 13200 |
| tccgcgcccc gcaacctccc cttctacgag cggctcggct tcaccgtcac cgccgacgtc | 13260 |
| gaggtgcccg aaggaccgcg cacctggtgc atgacccgca agcccggtgc ctgacgcccg | 13320 |
| ccccacgacc cgcagcgccc gaccgaaagg agcgcacgac cccatggctc cgaccgaagc | 13380 |
| cacccggggc ggccccgccg accccgcacc cgccccgag gccaccgac tctagaggat | 13440 |
| cataatcagc cataccacat ttgtagaggt tttacttgct ttaaaaaacc tcccacacct | 13500 |
| ccccctgaac ctgaaacata aaat | 13524 |

```
<210> SEQ ID NO 5
<211> LENGTH: 17
<212> TYPE: DNA
<213> ORGANISM: Artificial Sequence
<220> FEATURE:
<223> OTHER INFORMATION: Synthetic Construct

<400> SEQUENCE: 5
gacgtggtgc gcttcga                                                  17

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
gggcgtaatc ccagtcctct                                               20

<210> SEQ ID NO 7
<211> LENGTH: 22
```

```
<212> TYPE: DNA
<213> ORGANISM: Artificial Sequence
<220> FEATURE:
<223> OTHER INFORMATION: Synthetic Construct

<400> SEQUENCE: 7
aagcgtggcc aagaagcacc cc                                              22

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
gttgccattg ctacaggcat c                                               21

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct

<400> SEQUENCE: 9
actcgccttg atcgttggg                                                  19

<210> SEQ ID NO 10
<211> LENGTH: 28
<212> TYPE: DNA
<213> ORGANISM: Artificial Sequence
<220> FEATURE:
<223> OTHER INFORMATION: Synthetic Construct

<400> SEQUENCE: 10
acgctcgtcg tttggtatgg cttcattc                                        28

<210> SEQ ID NO 11
<211> LENGTH: 17
<212> TYPE: DNA
<213> ORGANISM: Artificial Sequence
<220> FEATURE:
<223> OTHER INFORMATION: Synthetic Construct

<400> SEQUENCE: 11
ggaccgccac atcgagc                                                    17

<210> SEQ ID NO 12
<211> LENGTH: 15
<212> TYPE: DNA
<213> ORGANISM: Artificial Sequence
<220> FEATURE:
<223> OTHER INFORMATION: Synthetic Construct

<400> SEQUENCE: 12
ccccgcttcg acgct                                                      15

<210> SEQ ID NO 13
<211> LENGTH: 28
<212> TYPE: DNA
<213> ORGANISM: Artificial Sequence
<220> FEATURE:
<223> OTHER INFORMATION: Synthetic Construct

<400> SEQUENCE: 13
```

```
tcaccgagct gcaagaactc ttcctcac                                        28

<210> SEQ ID NO 14
<211> LENGTH: 23
<212> TYPE: DNA
<213> ORGANISM: Artificial Sequence
<220> FEATURE:
<223> OTHER INFORMATION: Synthetic Construct

<400> SEQUENCE: 14
gaccaggcct catacatctc ctt                                             23

<210> SEQ ID NO 15
<211> LENGTH: 18
<212> TYPE: DNA
<213> ORGANISM: Artificial Sequence
<220> FEATURE:
<223> OTHER INFORMATION: Synthetic Construct

<400> SEQUENCE: 15
ggcagccttg atttggga                                                   18

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
aatgcggcct ccaactcgcg                                                 20

<210> SEQ ID NO 17
<211> LENGTH: 19
<212> TYPE: DNA
<213> ORGANISM: Artificial Sequence
<220> FEATURE:
<223> OTHER INFORMATION: Synthetic Construct

<400> SEQUENCE: 17
caacacggcg accctacaa                                                  19

<210> SEQ ID NO 18
<211> LENGTH: 28
<212> TYPE: DNA
<213> ORGANISM: Artificial Sequence
<220> FEATURE:
<223> OTHER INFORMATION: Synthetic Construct

<400> SEQUENCE: 18
tccaatactg tcttgcaata tacacagg                                        28

<210> SEQ ID NO 19
<211> LENGTH: 28
<212> TYPE: DNA
<213> ORGANISM: Artificial Sequence
<220> FEATURE:
<223> OTHER INFORMATION: Synthetic Construct

<400> SEQUENCE: 19
tgcacggaac tgaacacttc actgcaag                                        28

<210> SEQ ID NO 20
<211> LENGTH: 24
<212> TYPE: DNA
<213> ORGANISM: Artificial Sequence
```

```
<220> FEATURE:
<223> OTHER INFORMATION: Synthetic Construct

<400> SEQUENCE: 20
ccgtcgtgaa tagcctggac cctc                                                  24

<210> SEQ ID NO 21
<211> LENGTH: 28
<212> TYPE: DNA
<213> ORGANISM: Artificial Sequence
<220> FEATURE:
<223> OTHER INFORMATION: Synthetic Construct

<400> SEQUENCE: 21
atctgtgtgt tggtttttg tgtgcggc                                               28

<210> SEQ ID NO 22
<211> LENGTH: 29
<212> TYPE: DNA
<213> ORGANISM: Artificial Sequence
<220> FEATURE:
<223> OTHER INFORMATION: Synthetic Construct

<400> SEQUENCE: 22
aatcccagtc ctcttcctcg gcggcgata                                             29

<210> SEQ ID NO 23
<211> LENGTH: 29
<212> TYPE: DNA
<213> ORGANISM: Artificial Sequence
<220> FEATURE:
<223> OTHER INFORMATION: Synthetic Construct

<400> SEQUENCE: 23
agtatcggaa cactcgctct acgaaatgt                                             29

<210> SEQ ID NO 24
<211> LENGTH: 78
<212> TYPE: DNA
<213> ORGANISM: Artificial Sequence
<220> FEATURE:
<223> OTHER INFORMATION: Synthetic Construct

<400> SEQUENCE: 24
cactccctct ctgcgcgctc gctcgctcac tgaggccggg cgaccaaagg tcgcccacgc           60
ccgggctttg cccgggcg                                                         78

<210> SEQ ID NO 25
<211> LENGTH: 13
<212> TYPE: DNA
<213> ORGANISM: Artificial Sequence
<220> FEATURE:
<223> OTHER INFORMATION: Synthetic Construct

<400> SEQUENCE: 25
ctaggcaagg tca                                                              13

<210> SEQ ID NO 26
<211> LENGTH: 13
<212> TYPE: DNA
<213> ORGANISM: Artificial Sequence
<220> FEATURE:
<223> OTHER INFORMATION: Synthetic Construct

<400> SEQUENCE: 26
```

```
cggggcaaag tcg                                                            13
```

<210> SEQ ID NO 27
<211> LENGTH: 11
<212> TYPE: DNA
<213> ORGANISM: Artificial Sequence
<220> FEATURE:
<223> OTHER INFORMATION: Synthetic Construct

<400> SEQUENCE: 27

```
tatttgtgta g                                                              11
```

<210> SEQ ID NO 28
<211> LENGTH: 11
<212> TYPE: DNA
<213> ORGANISM: Artificial Sequence
<220> FEATURE:
<223> OTHER INFORMATION: Synthetic Construct

<400> SEQUENCE: 28

```
tattgactta g                                                              11
```

<210> SEQ ID NO 29
<211> LENGTH: 445
<212> TYPE: DNA
<213> ORGANISM: Artificial Sequence
<220> FEATURE:
<223> OTHER INFORMATION: Synthetic Construct

<400> SEQUENCE: 29

```
ctacctgctg atcgcccggc ccctgttcaa acatgtccta atactctgtc ggggcaaagg         60
tcggcagtag ttttccatct tactcaacat cctcccagtg tacgtaggat cctgtctgtc        120
tgcacatttc gtagagcgag tgttccgata ctctaatctc ccggggcaaa ggtcgtattg        180
acttaggtta cttattctcc ttttgttgac taagtcaata atcagaatca gcaggtttgg        240
agtcagcttg cagggatca gcagcctggg ttggaaggag ggggtataaa agcccccttca        300 ccaggagaag ccgtcacaca gatccacaag ctcctgctag caggtaagtg ccgtgtgtgg        360
ttcccgcggg cctggcctct ttacgggtta tggcccttgc gtgccttgaa ttactgacac        420
tgacatccac ttttttcttt tctcc                                              445
```

<210> SEQ ID NO 30
<211> LENGTH: 333
<212> TYPE: DNA
<213> ORGANISM: Artificial Sequence
<220> FEATURE:
<223> OTHER INFORMATION: Synthetic Construct

<400> SEQUENCE: 30

```
tgtctgtctg cacatttcgt agagcgagtg ttccgatact ctaatctccc ggggcaaagg         60
tcgtattgac ttaggttact tattctcctt ttgttgacta agtcaataat cagaatcagc        120
aggtttggag tcagcttggc agggatcagc agcctgggtt ggaaggaggg ggtataaaag        180
ccccttcacc aggagaagcc gtcacacaga tccacaagct cctgctagca ggtaagtgcc        240
gtgtgtggtt cccgcgggcc tggcctcttt acgggttatg gcccttgcgt gccttgaatt        300
actgacactg acatccactt tttgtttttc tcc                                     333
```

<210> SEQ ID NO 31
<211> LENGTH: 333
<212> TYPE: DNA
<213> ORGANISM: Artificial Sequence

```
<220> FEATURE:
<223> OTHER INFORMATION: Synthetic Construct

<400> SEQUENCE: 31
tgtctgtctg cacatttcgt agagcgagtg ttccgatact ctaatctccc ggggcaaagg      60
tcgtattggt gtaggttact tattctcctt ttgttgacta agtcaataat cagaatcagc     120
aggtttggag tcagcttggc agggatcagc agcctgggtt ggaaggaggg ggtataaaag     180
cccctthacc aggagaagcc gtcacacaga tccacaagct cctgctagca ggtaagtgcc     240
gtgtgtggtt cccgcgggcc tggcctcttt acgggttatg gcccttgcgt gccttgaatt     300
actgacactg acatccactt tttgtttttc tcc                                  333

<210> SEQ ID NO 32
<211> LENGTH: 333
<212> TYPE: DNA
<213> ORGANISM: Artificial Sequence
<220> FEATURE:
<223> OTHER INFORMATION: Synthetic Construct

<400> SEQUENCE: 32
tgtctgtctg cacatttcgt agagcgagtg ttccgatact ctaatctccc taggcaaggt      60
tcatattgac ttaggttact tattctcctt ttgttgacta agtcaataat cagaatcagc     120
aggtttggag tcagcttggc agggatcagc agcctgggtt ggaaggaggg ggtataaaag     180
cccctthacc aggagaagcc gtcacacaga tccacaagct cctgctagca ggtaagtgcc     240
gtgtgtggtt cccgcgggcc tggcctcttt acgggttatg gcccttgcgt gccttgaatt     300
actgacactg acatccactt tttgtttttc tcc                                  333

<210> SEQ ID NO 33
<211> LENGTH: 333
<212> TYPE: DNA
<213> ORGANISM: Artificial Sequence
<220> FEATURE:
<223> OTHER INFORMATION: Synthetic Construct

<400> SEQUENCE: 33
tgtctgtctg cacatttcgt agagcgagtg ttccgatact ctaatctccc taggcaaggt      60
tcatatttgt gtaggttact tattctcctt ttgttgacta agtcaataat cagaatcagc     120
aggtttggag tcagcttggc agggatcagc agcctgggtt ggaaggaggg ggtataaaag     180
cccctthacc aggagaagcc gtcacacaga tccacaagct cctgctagca ggtaagtgcc     240
gtgtgtggtt cccgcgggcc tggcctcttt acgggttatg gcccttgcgt gccttgaatt     300
actgacactg acatccactt tttgtttttc tcc                                  333
```

PRODUCTION OF OVERSIZED ADENO-ASSOCIATED VECTORS

CROSS-REFERENCE TO RELATED APPLICATIONS

This application is a National Phase application under 35 U.S.C. § 371 of International Application No. PCT/US2016/026486 filed Apr. 7, 2016, which claims priority to U.S. Provisional Application No. 62/144,862, filed Apr. 8, 2015, and U.S. Provisional Application No. 62/220,067, filed Sep. 17, 2015, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792013200SUBSEQLIST.txt, date recorded: Sep. 11, 2018, size: 31 KB).

FIELD OF THE INVENTION

The present invention relates to methods and cell lines for producing an adeno-associated virus (AAV) particle with an oversized recombinant AAV genome.

BACKGROUND OF THE INVENTION

Recombinant AAV (rAAV) vectors have become attractive delivery vehicles for gene transfer for genetic and chronic diseases. One of the limitations for use of rAAV vectors has been their small packaging capacity that has hindered gene therapy for a number of clinical applications requiring large cDNAs, e.g., Factor VIII (FVIII), dystrophin, dysferlin and cystic fibrosis transmembrane conductance regulator (CFTR). Early studies defined the packaging limit at 4.7 to 4.8 kb (Dong, J-Y et al. (1996) *Human Gene Therapy* 7:2101-2112). More recent studies have confirmed a limit of packaged vector genomes roughly at 5.0 to 5.2 kb size for AAV2, AAV5 or AAV8 capsids. In these studies, the oversized (or "fragmented") genomes of both polarities were typically deleted at the 5' end and most packaged genomes did not exceed ~5.2 kb (Lu, H. et al. (2008) *Human Gene Therapy* 19:648-654; Wu, Z. et al. (2010) *Molecular Therapy* 18:80-86; Grose, W. E. et al. (2012) *PLoS One* 7:e39233).

Accordingly, a need exists for better production platforms for oversized vectors that allow generation of robust yields with sufficient quality.

SUMMARY OF THE INVENTION

Described herein is a comprehensive analysis of production of oversized vectors by a producer cell line (PCL) platform. As described below, this PCL platform generates higher yield of better quality oversized recombinant adeno-associated virus (rAAV) vectors. The rAAV vectors generated contain higher amount of encapsidated larger genomes than observed in vector made by standard, triple transfection method. Additionally the cell lines are stable, and the vectors contain little contaminating, aberrant DNA. The vectors generate complete expression cassettes upon gene transfer in vivo and result in production of functional protein.

The invention provides a method for producing an adeno-associated virus (AAV) particle comprising an oversized recombinant AAV genome, the method comprising a) culturing an AAV producer cell line under conditions to generate rAAV particles, wherein the AAV producer cell line comprises i) nucleic acid encoding AAV rep and cap genes, and ii) a rAAV genome, wherein the rAAV genome is greater than about 4.7 kb; b) providing AAV helper functions; and c) collecting the rAAV particles comprising oversized rAAV genomes. In some embodiments, the nucleic acid encoding AAV rep and cap genes and/or the rAAV genome are stably maintained in the producer cell line. In some embodiments, the nucleic acid encoding AAV rep and cap genes and/or the rAAV genome are stably integrated into the genome of the producer cell line. In some embodiments, the rAAV genome comprises one or more AAV inverted terminal repeats (ITRs) and a heterologous transgene. In some embodiments, the rAAV genome comprises two AAV ITRs. In some embodiments, the rAAV genome is between about 4.7 kb and about 9.4 kb, optionally about 4.7 kb and 6.7 kb. In some embodiments, the AAV particles collected in step c) comprise rAAV genomes greater than about 4.7 kb. In some embodiments, the AAV particles collected in step c) comprise rAAV genomes between about 4.7 kb and about 9.4 kb, optionally about 4.7 kb and 6.7 kb. In some embodiments, the rAAV genome is between about 4.7 kb and about 5 kb, about 4.7 kb and about 6 kb, about 4.7 kb and about 7 kb, about 4.7 kb and about 8 kb, or about 4.7 kb and about 9 kb. In some embodiments, the rAAV genome is between about 4.7 kb and 6.7 kb or between about 5.2 kb and about 8.7 kb. In some embodiments, the rAAV genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 8.0 kb, or 9.0 kb in length or any value therebetween.

In some embodiments of the above methods, the heterologous transgene encodes a therapeutic transgene product. In some embodiments, the heterologous transgene is a human transgene. In some embodiments, the heterologous transgene encodes Factor VIII, dystrophin, dysferlin or cystic fibrosis transmembrane conductance regulator (CFTR). In some embodiments, the heterologous transgene is operably linked to a promoter. In further embodiments, the promoter is the mouse transthyretin (mTTR) promoter. In some embodiments, the rAAV genome comprises an intron. In further embodiments, the intron is a synthetic intron. In some embodiments, the rAAV genome comprises a polyadenylation signal. In further embodiments, the polyadenylation signal is a synthetic polyadenylation signal or a bovine growth hormone polyadenylation signal.

In some embodiments of the above methods, the rAAV particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the AAV serotype is AAV1, AAV2, AAV5, AAV6, AAV7, AAV8, AAVrh8, AAVrh8R, AAV9, AAV10, or AAVrh10. In some embodiments of the above methods, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the ITR and the capsid of the rAAV particle are derived from the same AAV serotype. In some embodiments, the ITR and the capsid are derived from AAV2. In other embodiments, the ITR and the capsid of the rAAV particles are derived from different AAV serotypes. In some embodiments, the AAV particles comprise AAV2 ITRs and AAVrh8R capsid. In some embodiments, the AAV particles comprise AAV2 ITRs and AAV8 capsid.

In some embodiments of the above methods, the producer cell line is derived from primate cells. In some embodiments, the producer cell line is derived from HeLa, 293, A549, or Perc.6 cells. In some embodiments, the producer cell line is adapted for growth in suspension. In some embodiments, the AAV helper functions are provided by adenovirus or HSV. In some embodiments, the rAAV particles are collected from between about 48 hours and about 96 hours after the provision of helper functions. In some embodiments, the methods further comprise purification of the rAAV particles. In some embodiments, the purification comprises one or more chromatography steps. In some aspects, the invention provides a rAAV particle comprising an oversized rAAV genome produced by the methods described herein.

In some aspects, the invention provides a composition comprising rAAV particles wherein at least about 15%, at least about 20%, at least about 25%, at least about 30%, at least about 35%, at least about 40%, at least about 45%, at least about 50%, at least about 55%, at least about 60% or at least about 70% of the rAAV particle encapsidate a rAAV genome greater than about 4.7 kb. In some embodiments, the rAAV genome comprises one or more AAV inverted terminal repeats (ITRs) and a heterologous transgene. In some embodiments, the rAAV genome comprises two AAV ITRs. In some embodiments, the rAAV genome is between about 4.7 kb and about 9.4 kb. In some embodiments, the rAAV genome is between about 4.7 kb and about 5 kb, about 4.7 kb and about 6 kb, about 4.7 kb and about 7 kb, about 4.7 kb and about 8 kb, or about 4.7 kb and about 9 kb. In some embodiments, the rAAV genome is between about 4.7 kb and 6.7 kb or between about 5.2 kb and about 8.7 kb. In some embodiments, the rAAV genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 8.0 kb or 9.0 kb in length or any value therebetween.

In some embodiments of the above compositions, the heterologous transgene encodes a therapeutic transgene product. In some embodiments, the heterologous transgene is a human transgene. In some embodiments, the heterologous transgene encodes Factor VIII, dystrophin, dysferlin or cystic fibrosis transmembrane conductance regulator (CFTR). In some embodiments, the heterologous transgene is operably linked to a promoter. In further embodiments, the promoter is the mouse transthyretin (mTTR) promoter. In some embodiments, the rAAV genome comprises an intron. In further embodiments, the intron is a synthetic intron. In some embodiments, the rAAV genome comprises a polyadenylation signal. In further embodiments, the polyadenylation signal is a synthetic polyadenylation signal or a bovine growth hormone polyadenylation signal.

In some embodiments of the above compositions, the rAAV particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the AAV serotype is AAV1, AAV2, AAV5, AAV6, AAV7, AAV8, AAVrh8, AAVrh8R, AAV9, AAV10, or AAVrh10. In some embodiments of the above methods, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the ITR and the capsid of the rAAV particle are derived from the same AAV serotype. In some embodiments, the ITR and the capsid are derived from AAV2. In other embodiments, the ITR and the capsid of the rAAV particles are derived from different AAV serotypes. In some embodiments, the AAV particles comprise AAV2 ITRs and AAVrh8R capsid. In some embodiments, the AAV particles comprise AAV2 ITRs and AAV8 capsid.

In some embodiments of the above compositions, the AAV particles comprising an oversized AAV genome are produced in a producer cell. In some embodiments, the producer cell line is derived from primate cells. In some embodiments, the producer cell line is derived from HeLa, 293, A549, or Perc.6 cells. In some embodiments, the producer cell line is adapted for growth in suspension. In some embodiments, the AAV helper functions are provided by adenovirus or HSV. In some embodiments, the rAAV particles are collected from between about 48 hours and about 96 hours after the provision of helper functions.

In some aspects, the invention provides a method for enhancing the expression of an oversized rAAV genome, the method comprising producing rAAV particles in a producer cell line by providing AAV helper functions to the cell line, wherein the producer cell line comprises a) nucleic acid encoding AAV rep and cap genes, and b) a rAAV genome, wherein the rAAV genome is greater than about 4.7 kb. In some embodiments, the expression of the oversized rAAV genome is about 1.25-fold, about 1.5-fold, about 1.75-fold, about 2.0-fold, about 2.5-fold, about 2.75-fold, about 3-fold, or about 5-fold greater than expression of the oversized rAAV genome from rAAV particles produced by transient transfection. In some embodiments, the expression kinetics of the oversized rAAV genome from particles produced by a producer cell line are faster expression kinetics compared to the expression kinetics of the oversized rAAV genome from rAAV particles produced by transient transfection. In some embodiments, the expression kinetics of the oversized rAAV genome produced by a producer cell line is about 5% faster, about 10% faster, about 25% faster, about 50% faster, about 75% faster, or about 90% faster than expression kinetics of the oversized rAAV genome from rAAV particles produced by transient transfection.

In some embodiments of the enhanced expression of an oversized rAAV genome, the nucleic acid encoding AAV rep and cap genes and/or the rAAV genome are stably maintained in the producer cell line. In some embodiments, the nucleic acid encoding AAV rep and cap genes and/or the rAAV genome are stably integrated into the genome of the producer cell line. In some embodiments, the rAAV genome comprises one or more AAV inverted terminal repeats (ITRs) and a heterologous transgene. In some embodiments, the rAAV genome comprises two AAV ITRs. In some embodiments, the rAAV genome is between about 4.7 kb and about 9.4 kb. In some embodiments, the rAAV genome is between about 4.7 kb and about 5 kb, about 4.7 kb and about 6 kb, about 4.7 kb and about 7 kb, about 4.7 kb and about 8 kb, or about 4.7 kb and about 9 kb. In some embodiments, the rAAV genome is between about 4.7 kb and 6.7 kb or between about 5.2 kb and about 8.7 kb.

In some embodiments of the enhanced expression of an oversized rAAV genome, the heterologous transgene encodes a therapeutic transgene product. In some embodiments, the heterologous transgene encodes Factor VIII, dystrophin, dysferlin or cystic fibrosis transmembrane conductance regulator (CFTR). In some embodiments, the heterologous transgene is a human transgene. In some embodiments, the heterologous transgene is operably linked to a promoter. In some embodiments, the promoter is the mouse transthyretin (mTTR) promoter. In some embodiments, the rAAV genome comprises an intron. In some embodiments, the intron is a synthetic intron. In some embodiments, the rAAV genome comprises a polyadenylation signal. In some embodiments, the polyadenylation signal is a synthetic polyadenylation signal or a bovine growth hormone polyadenylation signal.

In some embodiments of the enhanced expression of an oversized rAAV genome, the rAAV particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the AAV serotype is AAV1, AAV2, AAV5, AAV6, AAV7, AAV8, AAVrh8, AAVrh8R, AAV9, AAV10, or AAVrh10. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the ITR and the capsid of the rAAV particle are derived from the same AAV serotype. In some embodiments, the ITR and the capsid are derived from AAV2. In some embodiments, the ITR and the capsid of the rAAV particles are derived from different AAV serotypes. In some embodiments, the AAV particles comprise AAV2 ITRs and AAVrh8R capsid. In some embodiments, the AAV particles comprise AAV2 ITRs and AAV8 capsid.

In some embodiments of the enhanced expression of an oversized rAAV genome, the producer cell line is derived from primate cells. In some embodiments, the producer cell line is derived from HeLa, 293, A549, or Perc.6 cells. In some embodiments, the producer cell line is adapted for growth in suspension. In some embodiments, the AAV helper functions are provided by adenovirus, HSV or baculovirus. In some embodiments, the rAAV particles are collected from between about 48 hours and about 96 hours after the provision of helper functions. In some embodiments, the methods further comprise purification of the rAAV particles. In some embodiments, the purification comprises one or more chromatography steps.

In some aspects, the invention provides a cell line for producing an adeno-associated virus (AAV) particle comprising an oversized recombinant AAV genome, the cell line comprising a) nucleic acid encoding AAV rep and cap genes, and b) a rAAV genome, wherein the rAAV genome is greater than about 4.7 kb. In some embodiments, the nucleic acid encoding AAV rep and cap genes and/or the rAAV genome are stably maintained in the producer cell line. In some embodiments, the nucleic acid encoding AAV rep and cap genes and/or the rAAV genome are stably integrated into the genome of the producer cell line. In some embodiments, the rAAV genome comprises one or more AAV inverted terminal repeats (ITRs) and a heterologous transgene. In some embodiments, the rAAV genome is between about 4.7 kb and about 9.4 kb. In some embodiments, the rAAV genome is between about 4.7 kb and about 5 kb, about 4.7 kb and about 6 kb, about 4.7 kb and about 7 kb, about 4.7 kb and about 8 kb, or about 4.7 kb and about 9 kb. In some embodiments, the rAAV genome is between about 4.7 kb and 6.7 kb or between about 5.2 kb and about 8.7 kb. In some embodiments, the rAAV genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 8.0 kb, 8.7 kb, or 9.0 kb in length or any value therebetween.

In some embodiments of the cell lines, the heterologous transgene encodes a therapeutic transgene product. In some embodiments, the heterologous transgene is a human transgene. In some embodiments, the heterologous transgene encodes Factor VIII, dystrophin, dysferlin or cystic fibrosis transmembrane conductance regulator (CFTR). In some embodiments, the heterologous transgene is operably linked to a promoter. In further embodiments, the promoter is the mouse transthyretin (mTTR) promoter. In some embodiments, the rAAV genome comprises an intron. In further embodiments, the intron is a synthetic intron. In some embodiments, the rAAV genome comprises a polyadenylation signal. In further embodiments, the polyadenylation signal is a synthetic polyadenylation signal or a bovine growth hormone polyadenylation signal.

In some embodiments of the above cell lines, the rAAV particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the AAV serotype is AAV1, AAV2, AAV5, AAV6, AAV7, AAV8, AAVrh8, AAVrh8R, AAV9, AAV10, or AAVrh10. In some embodiments of the above methods, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the ITR and the capsid of the rAAV particle are derived from the same AAV serotype. In some embodiments, the ITR and the capsid are derived from AAV2. In other embodiments, the ITR and the capsid of the rAAV particles are derived from different AAV serotypes. In some embodiments, the AAV particles comprise AAV2 ITRs and AAVrh8R capsid. In some embodiments, the AAV particles comprise AAV2 ITRs and AAV8 capsid.

In some embodiments of the above cell lines, the producer cell line is derived from primate cells. In some embodiments, the producer cell line is derived from HeLa, 293, A549, or Perc.6 cells. In some embodiments, the producer cell line is adapted for growth in suspension. In some embodiments, AAV particles are produced in the cell line by providing AAV helper functions. In some embodiments, the AAV helper functions are provided by adenovirus or HSV. In some embodiments, rAAV particles are collected from between about 48 hours and about 96 hours after the provision of helper functions.

In some aspects, the invention provides an adeno-associated virus (AAV) particle comprising a rAAV genome encapsidated by an AAV capsid, wherein the rAAV genome is greater than about 4.7 kb. In some embodiments, the rAAV genome comprises one or more AAV inverted terminal repeats (ITRs) and a heterologous transgene. In some embodiments, the rAAV genome comprises two AAV ITRs. In some embodiments, the rAAV genome is between about 4.7 kb and about 9.4 kb. In some embodiments, the rAAV genome is between about 4.7 kb and about 5 kb, about 4.7 kb and about 6 kb, about 4.7 kb and about 7 kb, about 4.7 kb and about 8 kb, or about 4.7 kb and about 9 kb. In some embodiments, the rAAV genome is between about 4.7 kb and 6.7 kb or between about 5.2 kb and about 8.7 kb. In some embodiments, the rAAV genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 8.0 kb, 8.7 or 9.0 kb in length or any value therebetween.

In some embodiments, the invention provides AAV particles comprising an oversized rAAV genome wherein the heterologous transgene encodes a therapeutic transgene product. In some embodiments, the heterologous transgene is a human transgene. In some embodiments, the heterologous transgene encodes Factor VIII, dystrophin, dysferlin or cystic fibrosis transmembrane conductance regulator (CFTR). In some embodiments, the heterologous transgene is operably linked to a promoter. In further embodiments, the promoter is the mouse transthyretin (mTTR) promoter. In some embodiments, the rAAV genome comprises an intron. In further embodiments, the intron is a synthetic intron. In some embodiments, the rAAV genome comprises a polyadenylation signal. In further embodiments, the polyadenylation signal is a synthetic polyadenylation signal or a bovine growth hormone polyadenylation signal.

In some embodiments of the above cell lines, the rAAV particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the AAV serotype is AAV1, AAV2, AAV5, AAV6, AAV7, AAV8, AAVrh8, AAVrh8R, AAV9, AAV10, or AAVrh10. In some embodiments of the above methods, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the ITR and the capsid of the rAAV particle are derived from the same AAV serotype. In some embodiments, the ITR and the capsid are derived from AAV2. In other embodiments, the ITR and the capsid of the rAAV particles are derived from different AAV serotypes. In some embodiments, the AAV particles comprise AAV2 ITRs and AAVrh8R capsid. In some embodiments, the AAV particles comprise AAV2 ITRs and AAV8 capsid.

In some embodiments of the invention, the AAV particles comprising an oversized AAV genome are produced in a producer cell. In some embodiments, the producer cell line is derived from primate cells. In some embodiments, the producer cell line is derived from HeLa, 293, A549, or Perc.6 cells. In some embodiments, the producer cell line is adapted for growth in suspension. In some embodiments, the AAV helper functions are provided by adenovirus or HSV. In some embodiments, the rAAV particles are collected from between about 48 hours and about 96 hours after the provision of helper functions.

In some embodiments, the invention provides an AAV particle comprising an oversized rAAV genome wherein the rAAV genome comprises 5' to 3' an AAV2 ITR, a mTTR promoter, a synthetic intron, a transgene encoding human FVIII, a synthetic polyadenylation sequence, and an AAV2 ITR. In some embodiments, the rAAV genome comprises 5' to 3' an AAV2 ITR, a mTTR promoter, a synthetic intron, a transgene encoding human FVIII, a bovine growth hormone synthetic polyadenylation sequence, and an AAV2 ITR. In some embodiments, the FVIII comprises a deletion of all or part of the B domain. In some embodiments, the AAV particle comprises AAVrh8R capsid. In some embodiments, the AAV particle comprises AAV8 capsid.

In some aspects, the invention provides a rAAV vector comprising a rAAV genome, wherein the rAAV genome comprises 5' to 3' an AAV2 ITR, a mTTR promoter, a synthetic intron, a transgene encoding human FVIII, a synthetic polyadenylation sequence, and an AAV2 ITR. In some embodiments, the rAAV genome comprises 5' to 3' an AAV2 ITR, a mTTR promoter, a synthetic intron, a transgene encoding human FVIII, a bovine growth hormone synthetic polyadenylation sequence, and an AAV2 ITR. In some embodiments, the FVIII comprises a deletion of all or part of the B domain.

In some embodiments, the invention provides method of treating an individual with a disease or disorder comprising administering to the individual an AAV particle comprising an oversized rAAV genome encoding a therapeutic transgene wherein the therapeutic transgene is suitable for treating the disease or disorder. In some embodiments, the individual is a mammal (e.g., a human). In some embodiments, the disease or disorder is hemophilia A. In some embodiments, the therapeutic transgene encodes factor VIII; for example, human factor VIII including B domain-deleted human factor VIII.

In some embodiments, the invention provides kits comprising AAV particles comprising an oversized rAAV genome as described herein.

All references cited herein, including patent applications and publications, are incorporated by reference in their entirety.

BRIEF DESCRIPTION OF THE DRAWINGS

FIG. 1B shows an alignment of the mTTR promoter sequences used in the experiments described herein.

(FIG. 2A) FVIII TriplePlay plasmid was cut with SpeI that generates a 13 kb linear fragment. This was used as a size control for unit-length TriplePlay plasmid and for integrated copy number standard. (FIG. 2B) Integrity of the integrated vector genome was analyzed by digestion with BglII and HincII. These enzymes cut within the FVIII expression cassette resulting in 1.8 and 2.8 kb fragments. In both figures, diagrams showing the vectors and restriction sites are provided.

(FIG. 3A) Time-course for AAVrh8R/5.1 kb vector production. Shaker cultures were infected with wild-type adenovirus (wt Ad), samples were collected on days 2, 3 and 4, and vector yield was quantitated by qPCR in vector genomes per ml (VG/ml). (FIG. 3B) The stability of selected high producing masterwells. rAAV vector production levels are shown for MW #287 (AAV8/5.1 kb), MW #35 (AAVrh8R/5.1 kb) and MW #163 (AAVrh8R/5.4 kb). Masterwells were passaged up to passage 20 or 26 and rAAV productivity (DRP/ml) was quantitated by qPCR.

(FIG. 6A) Southern analysis using with 4.0 kb FVIII probe (FVIII domains A1, A2, A3 and C1). VG were loaded at 1.1 and $6.0 \times 10^9$ VG/lane and separated on 1% alkaline gel. 5.1 kb FVIII vector generated by PCL (MW #35) or triple transfection were compared to 4.6 kb size vector (identical to rh8R/5.1 kb vector except C1 domain was deleted to create normal size vector). (FIG. 6B) The signal intensity of each distinct VG size was quantitated and graphed as % of total signal in each lane.

(FIG. 7A) Diagram showing the location of the oligonucleotide probes used. Values indicate distance in nucleotides for the respective 3' termini. (FIG. 7B) Analysis of the minus strands. (FIG. 7C) Analysis of the plus strands.

FIGS. 8A, 8B, 8C and 8D show the characterization of 5' and 3' ends of packaged vector genomes in PCL or TXN generated rAAVrh8R/5.1 kb vectors. (FIG. 8A) Diagram showing the location of the oligonucleotide probes to 5' and 3'termini of plus and minus strands of vector genomes used. (FIG. 8B) Quantitation of plus and minus strands of 5.1 kb vector genomes in each lot. Vector analyzed included consisted 4.6 kb or 5.1 kb mTTR-FVIII genomes. Vector production method (PCL or TXN) is indicated. All vectors were purified in similar manner. Analysis was performed as described in FIG. 5 by applying 2-fold serial dilutions of each vector onto membrane (starting at $3.0 \times 10^9$; total of eight decreasing vector concentrations). Plasmids containing FIX (negative control) or FVIII (positive control) cDNA were used as controls for specificity of the signal. (FIG. 8C) Southern analysis using 3' and 5' terminal oligonucleotide probes for the 5.1 kb vectors. VG were loaded at 1.5 and $7.5 \times 10^9$ VG/lane and separated on 1% alkaline gel. 5.1 kb FVIII vector generated by PCL (MW #35) or triple transfection (TXN) were compared to 4.6 kb size vector. Size markers (2.7, 4.7 and 5.1 kb) are shown. Top panel, plus strand analysis; bottom panel, minus strand analysis. Oligonucleotides used for each panel are shown. White arrows indicate missing signals. (FIG. 8D) Quantitation of genome sizes in each vector. The signal intensity in the panels probed with the 3' terminal oligonucleotide probes (detects all packaged genomes) was quantitated by ImageJ. The intensity of each distinct VG size (>4.7 kb, 4.7 kb and <4.7 kb) was quantitated and graphed as % of total signal in each lane.

(FIG. 9A) Diagram showing the location of the oligonucleotide probes to 5' and 3'termini of plus and minus strands of vector genomes used. (FIG. 9B) Quantitation of plus and minus strands of 5.4 kb vector genomes in each lot by dot blot analysis. Analysis was performed as described in FIG. 8. (FIG. 9C) Southern analysis of 5.4 kb vectors using 3' and 5' terminal oligonucleotide probes. Experiment was performed as described in FIG. 8.

(FIG. 10A) Plasma FVIII protein activity. Activity was measured in day 7, 14, 28, 42 and 56 plasma samples by Coatest assay. (FIG. 10B) Clotting times on days 28 and 56. Clotting times were analyzed by activated partial thromboplastin time (aPTT). Each treatment group contained n=7-10 mice/group. Statistical significance is indicated as follows: *, $p<0.05$; , $p<0.01$, *, $p<0.001$ by Student t-test.

(FIG. 11A) Plasma FVIII protein activity. Activity was measured in days 21, 35, 56, 70 and 84 samples by Coatest assay. (FIG. 11B) Plasma clotting times on day 21. (FIG. 11C) Plasma clotting times on day 56. Plasma clotting times were measured by aPTT assay. Clotting times for mouse strains (129S and BALB/c) are shown for comparison.

(FIG. 12A) Plasma FVIII activity. Activity was measured in day 24 and 43 plasma samples by Coatest assay. (FIG. 12B) Day 24 plasma clotting times by aPTT assay. (FIG. 12C) Vector genome (VG) copies in liver on days 3 and 43. Animals were sacrificed 3 and 43 days after vector administration and VG copies were quantitated by qPCR and are shown as copies/500 ng of total liver DNA. Each treatment group contained n=6-8 mice/group. Statistical significance is indicated as follows: *, p<0.05; , p<0.01; *, p<0.001 by Student t-test.

FIG. 13A shows a diagram for 5.1, 5.9 and 6.7 kb AAV2/SEAP vectors. FIG. 13B shows data from individual masterwells (MWs) with respect to the vector yield in relative and specific production (n=2) assays. The vector yield is indicated as DRP/ml.

DETAILED DESCRIPTION

Figure 1A:
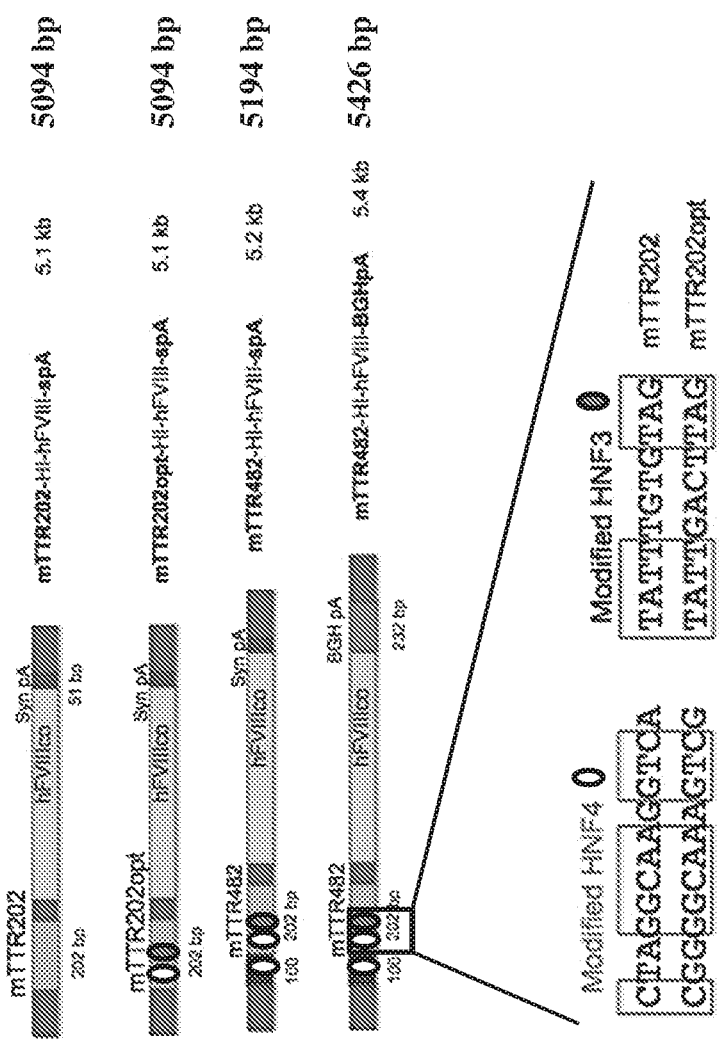
FIG. 1A shows a diagram of hFVIII expression cassettes, based on mouse transthyretin (mTTR) promoter, ranging from 5.1 to 5.4 kb vector genome sizes (as indicated). Sequence modification in HNF4 binding sites (open circles) and HNF3 binding sites (filled circles) and their location are shown. Abbreviations for FIGS. 1A, 1B and 1C: ITRs, rAAV inverted terminal repeats; mTTR, mouse transthyretin promoter (202 or 482 bp); HI, hybrid intron; FVIII, B-domain deleted human FVIII cDNA; syn pA, synthetic (syn pA); BGH or bovine growth hormone (BGH) poly A (pA).

As discussed in detail herein, the inventors have developed a producer cell line platform capable of generating higher yield of better quality oversized recombinant adeno-associated virus (rAAV) vectors. This platform has been characterized using rAAV vectors containing human factor VIII cDNA as an exemplary construct. Compared to production using the standard triple transfection method, this platform generated rAAV vectors with a higher amount of encapsidated larger genomes. rAAV vectors generated using this platform were also competent for gene transfer in vivo and resulted in production of functional factor VIII.

Accordingly, the present invention provides methods for producing an adeno-associated virus (AAV) particle containing an oversized recombinant AAV genome. In some embodiments, the methods include culturing an AAV producer cell line under conditions to generate rAAV particles, where the AAV producer cell line contains i) nucleic acid encoding AAV rep and cap genes, and ii) a rAAV genome, where the rAAV genome is between about 4.7 kb and about 9.4 kb, optionally about 4.7 kb and 6.7 kb; b) providing AAV helper functions; and c) collecting the rAAV particles containing oversized rAAV genomes. In some embodiments, the rAAV genome is greater than about 5 kb. In some embodiments, the rAAV genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 8.0 kb or 9.0 kb in length or any value therebetween. Further provided herein are rAAV particles containing an oversized recombinant AAV genome produced by the methods of the present disclosure.

Still further provided herein are compositions including rAAV particles where at least at least about 15%, at least about 20%, at least about 25%, at least about 30%, at least about 35%, at least about 40%, at least about 45%, at least about 50%, at least about 55%, at least about 60% or at least about 70% of the rAAV particle encapsidate an rAAV genome greater than about 5 kb.

Yet further provided herein are cell lines for producing an adeno-associated virus (AAV) particle containing an oversized recombinant AAV genome, the cell line including a) nucleic acid encoding AAV rep and cap genes, and b) a rAAV genome, where the rAAV genome is between about 4.7 kb and about 9.4 kb, optionally about 4.7 kb and 6.7 kb. In some embodiments, the rAAV genome is greater than about 5 kb.

Yet further provided herein are adeno-associated virus (AAV) particles containing a rAAV genome encapsidated by an AAV capsid, where the rAAV genome is between about 4.7 kb and about 9.4 kb, optionally about 4.7 kb and 6.7 kb. In some embodiments, the rAAV genome is greater than about 5 kb.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH$_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one inverted terminal repeat sequences (ITRs). In some embodiments, the recombinant nucleic acid is flanked by two ITRs.

A "recombinant AAV vector (rAAV vector)" refers to a polynucleotide vector comprising one or more heterologous sequences (i.e., nucleic acid sequence not of AAV origin) that are flanked by at least one or two AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e., AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and encapsidated in a viral particle, e.g., an AAV particle. A rAAV vector can be packaged into an AAV virus capsid to generate a "recombinant adeno-associated viral particle (rAAV particle)".

As used herein, a "producer cell line" is a stable cell line capable of producing AAV particles. In some embodiments, AAV replication and/or capsid genes are stably maintained in the host cell line. In some embodiments, an AAV vector genome comprising one or more AAV ITRs and heterologous nucleic acid (e.g., a heterologous transgene) are stably maintained in the host cell line. In some embodiments, AAV replication and/or capsid genes and an AAV vector genome comprising one or more AAV ITRs and heterologous nucleic acid (e.g., a heterologous transgene) are stably maintained in the host cell line. In some embodiments, one or more of AAV replication genes, capsid genes or an AAV vector genome comprising one or more AAV ITRs are stably integrated into the genome of the host cell line. One skilled in the art would understand that a stably maintained nucleic acid is maintained in the host cell line upon multiple passages (e.g., 5, 10, 15, 25, or more passages).

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as miRNA, siRNA, or shRNA.

The term "transthyretin (TTR) promoter" refers to a polynucleotide sequence capable of driving gene expression derived from a transthyretin gene. In some embodiments, the transthyretin promoter may be from a mouse transthyretin (mTTR) gene (e.g., *Mus musculus* transthyretin, as represented by GenBank Entrez Gene ID 22139). Examples of TTR promoters are presented in FIG. 1B.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.*, 10:1031-1039; Veldwijk et al. (2002) *Mol. Ther.*, 6:272-278.

The term "vector genome (vg)" as used herein may refer to one or more polynucleotides comprising a set of the polynucleotide sequences of a vector, e.g., a viral vector. A vector genome may be encapsidated in a viral particle. Depending on the particular viral vector, a vector genome may comprise single-stranded DNA, double-stranded DNA, or single-stranded RNA, or double-stranded RNA. A vector genome may include endogenous sequences associated with a particular viral vector and/or any heterologous sequences inserted into a particular viral vector through recombinant techniques. For example, a recombinant AAV vector genome may include at least one ITR sequence flanking a promoter, a sequence of interest (e.g., a heterologous transgene), optionally an intron, and a polyadenylation sequence. A complete vector genome may include a complete set of the polynucleotide sequences of a vector. In some embodiments, the nucleic acid titer of a viral vector may be measured in terms of vg/mL. Methods suitable for measuring this titer are known in the art (e.g., quantitative PCR).

The term "oversized recombinant AAV genome" may refer to a recombinant AAV genome with a size (as measured in nucleotide base pairs) greater than the conventional packaging limit for an AAV genome, which has been defined in the art as 4.7 to 4.8 kb (see, e.g., Dong, J-Y et al. (1996)

*Human Gene Therapy* 7:2101-2112). In some embodiments, an oversized recombinant AAV genome is greater than about 4.7 kb. In some embodiments, an oversized recombinant AAV genome is greater than about 5 kb. In some embodiments, an oversized recombinant AAV genome is between about 4.7 kb and about 9.4 kb, optionally about 4.7 kb and 6.7 kb.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.,* 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.,* 144:113-124; or in Fisher et al. (1996) *J. Virol.,* 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

"AAV helper functions" refer to functions that allow AAV to be replicated and packaged by a host cell. AAV helper functions can be provided in any of a number of forms, including, but not limited to, helper virus or helper virus genes which aid in AAV replication and packaging. Other AAV helper functions are known in the art such as genotoxic agents.

A "helper virus" for AAV refers to a virus that allows AAV (which is a defective parvovirus) to be replicated and packaged by a host cell. A number of such helper viruses have been identified, including adenoviruses, herpesviruses, poxviruses such as vaccinia and baculovirus. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV). Examples of adenovirus helper functions for the replication of AAV include E1A functions, E1B functions, E2A functions, VA functions and E4orf6 functions. Baculoviruses available from depositories include *Autographa californica* nuclear polyhedrosis virus.

A preparation of rAAV is said to be "substantially free" of helper virus if the ratio of infectious AAV particles to infectious helper virus particles is at least about $10^2:1$; at least about $10^4:1$, at least about $10^6:1$; or at least about $10^8:1$ or more. In some embodiments, preparations are also free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. An example of an alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms.

As used herein, a "therapeutic" agent (e.g., a therapeutic polypeptide, nucleic acid, or transgene) is one that provides a beneficial or desired clinical result, such as the exemplary clinical results described above. As such, a therapeutic agent may be used in a treatment as described above.

As used herein, "differential coefficient distribution value" or "C(S)" is a variant of the distribution of Lamm equation solutions to describe distributions of sedimenting particles; for example during ultracentrifugation.

As used herein, "Svedberg units" refers to a unit for sedimentation rate. The sedimentation rate for a particle of a given size and shape measures how fast the particle sediments. One Svedberg unit is equivalent to $10^{-13}$ seconds. For example, Svedberg units are often used to reflect the rate at which a molecule travels under the centrifugal force of a centrifuge.

As used herein, "sedimentation velocity conditions" or "boundary sedimentation velocity conditions" may refer to any experimental conditions under which a sample solution is subjected to sedimentation velocity analysis. Sedimentation velocity allows the study of particles over a wide range of pH and ionic strength conditions and at temperatures 4 to 40° C. The rate at which the sedimentation boundary moves is a measure of the sedimentation coefficient of the sedimenting species. The sedimentation coefficient depends on the molecular weight (larger particles sediment faster) and also on molecular shape. The minimum width of the sedimentation boundary is related to the diffusion coefficient of the molecule; the presence of multiple species with similar sedimentation coefficients will cause the boundary to be broader than expected on the basis of diffusion alone. Sedimentation velocity conditions may include without limitation any conditions related to the rotor speed, distance between sample and rotor center, temperature, solvent, sample, buffer, ultracentrifugation time, time interval for detection, sector and optical window characteristics, AUC instrumentation (including ultracentrifuge and detection apparatus), equilibrium dialysis of reference solvent, and data analysis algorithms.

As used herein, the term "analytical density gradient sedimentation equilibrium" relates to methods for measuring the buoyant density of a particle, or using differences in buoyant density to separate different species of particles. These methods may use, for example, AUC sedimentation equilibrium techniques. In these methods, a particle solution (e.g., without limitation, a solution of a polypeptide, polynucleotide, or viral capsids) may be subjected to ultracentrifugation in a gradient solvate, such as a cesium chloride or cesium sulfate gradient, until equilibrium with the solvate is attained. At equilibrium, the particle solution will concentrate, or band, at the position in the gradient where the density of the particle is equal to that of the solvate. The position of bands may be used to calculate particle density, or a band may be extracted to isolate a single species of particle.

As used herein, the "SEDFIT algorithm" is an algorithm that allows one to analyze hydrodynamic data such as sedimentation velocity (Schuck (2000) *Biophys. J.*, 78:1606-19). In the SEDFIT algorithm, a grid of sedimentation coefficients across an expected range is created. Sedimentation boundaries are simulated using solutions to the Lamm equation for each sedimentation coefficient, assuming constant particle shape and solvent frictional ratio.

As used herein, the term "F statistic" or "F ratio" refers to the confidence level. This parameter controls the amount of regularization used. It has a different meaning for different ranges: From 0 to 0.5, no regularization is used. Values from 0.5 to 0.999 correspond to probabilities P (confidence levels). From these P-values, the desired chi-square increase allowed for the parsimony constraint of the regularization is calculated with F-statistics. A value of 0.51 will cause very little regularization; values of 0.68 to 0.90 would correspond to commonly used confidence levels (usually, with 50 scans or more the chi-square increase corresponding to a probability of 0.7 is of the order of 0.1%), while values close to 0.99 would cause very high regularization. The relationship of these values with probabilities can be examined using the F-statistics calculator. If numbers>1 are entered, they are taken directly as chi-square ratios (as there are no probabilities>1). For example, a value of 1.1 will result in regularization with 10% chi-square increase.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

III. Viral Particles

Certain aspects of the present disclosure relate to adeno-associated virus (AAV) particles containing an oversized recombinant AAV (rAAV) genome (e.g., as produced by the methods and/or cell lines disclosed herein). Certain aspects of the present disclosure relate to adeno-associated virus (AAV) particles containing a rAAV genome between about 4.7 kb and about 9.4 kb, optionally about 4.7 kb and 6.7 kb. In some embodiments, the rAAV genome is greater than about 5 kb encapsidated by an AAV capsid. In some embodiments, the rAAV particle comprises a rAAV vector. In some embodiments, the rAAV vector contains a rAAV genome between about 4.7 kb and about 9.4 kb, optionally about 4.7 kb and 6.7 kb. In some embodiments, the rAAV genome is greater than about 5 kb. In some embodiments, the rAAV genome is between about 5 kb and about 7.0 kb, between about 4.7 kb and about 9.4 kb, or between about 4.7 kb and about 6.7 kb. In some embodiments, the rAAV genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.2 kb, 9.3 kb or 9.4 kb in length or any value therebetween.

In some embodiments, the viral particle is a recombinant AAV particle comprising a nucleic acid comprising a heterologous nucleic acid (e.g., a heterologous transgene) flanked by one or two AAV inverted terminal repeats (ITRs). The nucleic acid is encapsidated in the AAV particle. The AAV particle also comprises capsid proteins. In some embodiments, the nucleic acid comprises the coding sequence(s) of interest (e.g., a heterologous transgene) operatively linked components in the direction of transcription, control sequences including transcription initiation and termination sequences, thereby forming an expression cassette. The expression cassette is flanked on the 5' and 3' end by at least one functional AAV ITR sequence. By "functional AAV ITR sequence" it is meant that the ITR sequence functions as intended for the rescue, replication and packaging of the AAV virion. See Davidson et al., *PNAS*, 2000, 97(7)3428-32; Passini et al., *J. Virol.*, 2003, 77(12):7034-40; and Pechan et al., *Gene Ther.*, 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10):6081-6; and Bossis et al., *J. Virol.*, 2003, 77(12): 6799-810. Use of any AAV serotype is considered within the scope of the present invention. In some embodiments, a rAAV vector is a vector derived from an AAV serotype, including without limitation, AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV or the like. For example, in some embodiments, the AAV serotype is AAV1, AAV2, AAV5, AAV6, AAV7, AAV8, AAVrh8, AAVrh8R, AAV9, AAV10, or AAVrh10. In some embodiments, the nucleic acid in the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs or the like. In certain embodiments, the nucleic acid in the AAV comprises an AAV2 ITR.

In further embodiments, the rAAV particles comprise an AAV1 capsid, an AAV2 capsid, an AAV3 capsid, an AAV4 capsid, an AAV5 capsid, an AAV6 capsid (e.g., a wild-type AAV6 capsid, or a variant AAV6 capsid such as ShH10, as described in U.S. PG Pub. 2012/0164106), an AAV7 capsid, an AAV8 capsid, an AAVrh8 capsid, an AAVrh8R capsid, an AAV9 capsid (e.g., a wild-type AAV9 capsid, or a modified AAV9 capsid as described in U.S. PG Pub. 2013/0323226), an AAV10 capsid, an AAVrh10 capsid, an AAV11 capsid, an AAV12 capsid, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, a mouse AAV capsid, a rAAV2/HBoV1 capsid, or an AAV capsid described in U.S. Pat. No. 8,283,151 or International Publication No. WO/2003/042397. In some embodiments, a mutant capsid protein maintains the ability to form an AAV capsid. In some embodiments, the rAAV particle comprises AAV5 tyrosine mutant capsid (Zhong L. et al., (2008) *Proc Natl Acad Sci USA* 105(22):7827-7832. In further embodiments, the rAAV particle comprises capsid proteins of an AAV serotype from Clades A-F (Gao, et al., *J. Virol.* 2004, 78(12):6381). In some embodiments, the rAAV particle comprises an AAV1 capsid protein or mutant thereof. In other embodiments, the rAAV particle comprises an AAV2 capsid protein or mutant thereof. In some embodiments, the AAV serotype is AAV1, AAV2, AAV5, AAV6, AAV7, AAV8, AAVrh8, AAVrh8R, AAV9, AAV10, or AAVrh10. In some embodiments, the rAAV particle comprises an AAV serotype 1 (AAV1) capsid. In some embodiments, the rAAV particle comprises an AAV serotype 2 (AAV2) capsid. In some embodiments, the rAAV particle comprises an AAVrh8R capsid or mutant thereof.

Different AAV serotypes are used to optimize transduction of particular target cells or to target specific cell types within a particular target tissue (e.g., liver or CNS tissue). A rAAV particle can comprise viral proteins and viral nucleic acids derived from the same serotype or different serotypes (e.g., a mixed serotype). For example, in some embodiments a rAAV particle can comprise AAV1 capsid proteins and at least one AAV2 ITR or it can comprise AAV2 capsid proteins and at least one AAV1 ITR. Any combination of AAV serotypes for production of a rAAV particle is provided herein as if each combination had been expressly stated herein. In some embodiments, the invention provides rAAV particles comprising an AAV1 capsid and a rAAV vector of the present disclosure (e.g., an expression cassette comprising a heterologous nucleic acid), flanked by at least one AAV2 ITR. In some embodiments, the invention provides rAAV particles comprising an AAV2 capsid. In some embodiments, the ITR and the capsid are derived from AAV2. In other embodiments, the ITR is derived from AAV2, and the capsid is derived from AAVrh8R.

Further aspects of the present disclosure relate to compositions including rAAV particles, where at least about 15%, at least about 20%, at least about 25%, at least about 30%, at least about 35%, at least about 40%, at least about 45%, at least about 50%, at least about 55%, at least about 60% or at least about 70%, at least about 80%, at least about 90% or at least about 95% of the rAAV particles encapsidate a rAAV genome between about 4.7 kb and about 9.4 kb, optionally about 4.7 kb and 6.7 kb. In some embodiments, the rAAV particles encapsidate a genome greater than about 5 kb. In some embodiments, the rAAV particles encapsidate a genome greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 8.0 kb or 9.0 kb in length or any value therebetween. In some embodiments, the packaged AAV genome did not contain a truncation of the 5' end. In some embodiments, the packaged AAV genome did not contain a truncation of the 3' end. Methods for assaying the size of a rAAV genome are known in the art and include without limitation Southern blotting and analytical ultracentrifugation, as described below.

In some embodiments, the compositions of the present disclosure contain rAAV particles, where at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% of the rAAV particles encapsidate a rAAV genome greater than about 4.7 kb, greater than about 5.0 kb, greater than about 5.1 kb, greater than about 5.2 kb, greater than about 5.3 kb, greater than about 5.4 kb, greater than about 5.5 kb, greater than about 5.6 kb, greater than about 5.7 kb, greater than about 5.8 kb, greater than about 5.9 kb, greater than about 6.0 kb, greater than about 6.5 kb, greater than about 7.0 kb, greater than about 7.5 kb, greater than about 8.0 kb, greater than about 8.5 kb, greater than about 9.0 kb, or greater than about 9.4 kb. In some embodiments, the packaged AAV genome did not contain a truncation of the 5' end. In some embodiments, the packaged AAV genome did not contain a truncation of the 3' end.

In some embodiments of the invention, recombinant viral particles in the composition are highly purified, suitably buffered, and concentrated. In some embodiments, the viral particles are concentrated to at least about $1 \times 10^7$ vg/mL to about $9 \times 10^{13}$ vg/mL or any concentration therebetween.

As described herein, one technique for characterizing a preparation of viral particles (e.g., one or more properties related to vector genome size and/or integrity) is through use of Southern blotting. For example, as described in more detail in the Examples below, a preparation of rAAV particles (optionally purified as described herein) may be treated with DNase to remove any non-encapsidated nucleic acid, treated with an agent to stop DNase digestion (e.g., EDTA), digested with a proteinase, then subjected to DNA extraction to remove packaged vector genomes. Vector genomes may then be separated using electrophoresis, cross-linked onto a membrane, and probed with one or more labeled probes that specifically hybridize to the vector genome. The size of the DNA fragments that are labeled by hybridization to the labeled probe (e.g., as compared to one or more specific size markers) indicates vector genome size. In addition, one or more probes may be used that hybridize to known segments of the vector genome (e.g., 5' or 3' ends). If one or more of these probes fail to hybridize to a vector genome, this indicates that the vector genome(s) of the preparation may be truncated or otherwise deleted, such that they are shorter than their predicted full size. Since packaging of AAV genomes is known to occur starting from the 3' ends (King, J. A. et al. (2001) *EMBO J.* 20:3282-3291), oversized vectors may lack sequence in 5' ends of minus and plus strands when genome size exceeds 4.7 kb. In some embodiments, the viral particles comprise oversized rAAV genomes greater than about 5.0 kb wherein the viral genomes encapsidated in the rAAV particles comprise relatively intact 5' and 3' ends; for example, as measured by hybridization to probes specific for the 5' and/or 3'ends. Hybridization may be measured by methods known in the art such as, but not limited to, Southern blot analysis or PCR. In some embodiments, the packaged AAV genome did not contain a truncation of the 5' end. In some embodiments, the packaged AAV genome did not contain a truncation of the 3' end.

Analytical Ultracentrifugation

As described herein, one technique for characterizing a preparation of viral particles (e.g., one or more properties related to vector genome size and/or integrity) is through use of analytical ultracentrifugation (AUC). For example, in some embodiments, AUC is used to assess vector genome integrity of recombinant adeno-associated viral (rAAV) particles in preparations of rAAV particles to distinguish viral particles with full, intact genomes, empty viral capsids and viral particles with variant (e.g., truncated, aggregates, impurities and the like) viral genomes. Further description of the use of analytical ultracentrifugation for characterizing viral (e.g., AAV) particles may be found in U.S. Provisional Patent Application Ser. No. 62/105,714, "Analytical Ultracentrifugation for Characterization of Recombinant Viral Particles," filed Jan. 20, 2015, which is hereby incorporated by reference in its entirety.

Analytical ultracentrifugation is a means to evaluate the molecular weight and the hydrodynamic and thermodynamic properties of a protein or other macromolecule. Heterogeneity of a protein or macromolecule by sedimentation velocity over a range of conditions including concentration, temperature, ionic strength, and pH. For example, a protein may be analyzed in a clinically relevant formulation. Use of analytical ultracentrifugation to characterize adenovirus preparations is provided by Berkowitz, S A & Philo J S, (2007) *Anal. Biochem.*, 362:16-37.

AUC analysis refers to quantitative methods for characterizing the biophysical properties of particles (e.g., polypeptides, polynucleotides, and viral capsids) by measuring their migration through a solvent in a centrifugal field. AUC analysis has been well characterized over many decades and is highly versatile. Because AUC analysis relies upon first-principle hydrodynamic and thermodynamic information, AUC may be applied to determine the biophysical properties of many types of particles across a wide range of particle concentrations and sizes. AUC analysis typically encompasses two basic types of experiment: sedimentation velocity and sedimentation equilibrium. Sedimentation equilibrium analysis yields thermodynamic properties of particles that may be used to measure characteristics such as stoichiometry and association constants. Sedimentation velocity yields hydrodynamic properties of particles that may be used to measure characteristics such as size, shape, and concentration. A feature of AUC analysis of viral preparations is that the same assay conditions may be used to analyze different preparations of viral particles regardless of nucleotide sequence of the viral genome or serotype of the capsid.

Certain aspects of the present disclosure relate to the use of sedimentation velocity analysis to characterize viral capsid properties. In some embodiments, sedimentation velocity analysis uses an ultracentrifuge velocity cell with two sectors in dialysis equilibrium (one for an experimental sample and one for a solvent-only reference sample), each containing two optical windows that allow light to pass through the compartment. Ultracentrifugation applies an angular velocity to the cell and leads to rapid sedimentation of the solute particles towards the bottom of the sector. As sedimentation occurs, solute is depleted near the meniscus at the top of the cell, creating a sedimenting boundary between the depleted region and the sedimenting solute. The rate of movement or migration of the sedimenting boundary is measured by taking measurements that compare the properties of the sample and reference sectors at specific time intervals (for sedimentation velocity, these intervals are typically on the order of minutes). If multiple species of solute are present, this may lead to the formation of multiple sedimenting boundaries, each corresponding to a resolvable species.

Several methods for optically detecting a sedimenting boundary and measuring its rate of movement or migration are known in the art (for reference, see Cole et al. (2008) *Methods Cell Biol.*, 84:143-79). In some embodiments, the reference and sample sectors may be assayed using absorbance detection. In this detection method, the absorbance at a particular wavelength may be measured for the sample and reference sectors at different radial positions within each sector. Alternatively, the time course of absorbance at a single radial position may be measured. Beer's Law provides a mathematical relationship between absorbance and a solute's extinction coefficient.

In some embodiments, the reference and sample sectors may be assayed using interference detection (e.g., Rayleigh interference detection). In the Rayleigh interference detection method, the interference optical system contains two parallel slits. A single, coherent beam of light is split such that it passes through both windows, and then the two beams are re-merged. When these two light waves are merged, they form an interference pattern of alternating light and dark fringes. If the sample and reference samples were to have an identical refractive index, the resulting interference fringes would be perfectly straight. Increasing the concentration of solute increases the solution's refractive index, thereby retarding the sample light beam and causing a vertical fringe shift. By measuring this fringe shift, one may measure the concentration of solute in the sample. Unlike absorbance detection, which measures absolute values for the sample and reference, interference detection measures a relative difference between the sample and reference. However, interference detection yields integrated peaks that are directly proportional to concentration, and it may be used for types of samples that do not absorb significantly. For a reference on using Rayleigh interference optics with AUC, see Furst (1997) *Eur. Biophys. J.* 35:307-10.

Measurement of the rate at which the sedimentation boundary moves may be used to derive many physical properties of solute particles. The rate of the boundary movement determines the sedimentation coefficient, which is based on the mass and shape (frictional coefficient) of the particle. The sedimentation coefficient of a particle, s, refers to the ratio of its velocity to the acceleration applied to it by a centrifugal field. Sedimentation coefficients are expressed in Svedberg units, S (one Svedberg unit is equivalent to $10^{-13}$ seconds). The sedimentation coefficient of a particle or solution of particles depends upon its properties, for example molecular weight (corrected for buoyancy), and the properties of the solvent.

The change in the concentration boundary of a solute over time during ultracentrifugation may be determined using the Lamm equation (Schuck (2000) *Biophys. J.*, 78:1606-19). Briefly, the Lamm equation calculates the change in the concentration boundary of a solute over time in response to the competing forces of sedimentation (which concentrates the solute) and diffusion (which disperses the solute), taking into account the sector-shaped cell and the centrifugal field generated by the rotor. The Lamm equation may be expressed as:

$$\partial c/\partial t = D[(\partial^2 c/\partial r^2) + 1/r(\partial c/\partial r)] - s\omega^2[r(\partial c/\partial r) + 2c] \quad \text{Equation 1:}$$

where c is the solute concentration, D represents the solute diffusion constant, s represents the sedimentation coefficient, ω represents the angular velocity of the rotor, r is the radius, and t is time.

By fitting raw AUC data to solutions of the Lamm equation, it is possible to determine solute characteristics such as the sedimentation coefficient and the change in concentration distribution. For example, experimentally determined values for the rate of change of a sedimenting boundary may be modeled using the Lamm equation to derive the sedimentation coefficient, molecular mass, or concentration of the solute forming the boundary. Several programs known in the art, such as SEDFIT (Schuck (2000) *Biophys. J.*, 78:1606-19), may be used to model the Lamm equation to AUC data. These programs are also able to apply the Lamm equation to solutions containing multiple solutes or multiple sedimenting boundaries.

One example of a suitable program for the determination of solute characteristics is the SEDFIT algorithm. In some embodiments, the SEDFIT algorithm may be used to calculate a differential coefficient distribution value, or C(S), using AUC data from a solution containing a mixture of particle species (for reference, see Schuck (2000) *Biophys. J.*, 78:1606-19). In the SEDFIT algorithm, a grid of sedimentation coefficients across an expected range is created. Sedimentation boundaries are simulated using solutions to the Lamm equation for each sedimentation coefficient, assuming constant particle shape and solvent frictional ratio. Actual AUC data are then fit to these Lamm solutions to derive the differential coefficient distribution value, or C(S). Many other programs useful for analyzing AUC data may be found in Cole and Hansen (1999) *J. Biomol. Tech.* 10:163-76.

In some embodiments, viral particles are generated in a suitable host cells and purified. In some embodiments, the viral particles are purified by affinity chromatography. Methods to purify AAV particles are known in the art. For example, by use of an antibody of a viral capsid protein or binding ligand of a viral capsid protein immobilized on a chromatography media.

In some embodiments, sedimentation velocity analytical ultracentrifugation (SV-AUC) analysis is performed using an analytical ultracentrifuge that is capable of characterizing a sample in its native state under biologically relevant solution conditions (e.g., ProteomeLab™ XL-I (Beckman Coulter)). When using the ProteomeLab™ XL-1, sample is loaded into the sample sector of a two sector velocity cell, a vehicle control (e.g., PBS without recombinant viral) is loaded into the corresponding reference sector. The sample is placed in the four-hole rotor and allowed to equilibrate in the instrument until a temperature of about 20° C. and full vacuum are maintained for about one hour. In an exemplary embodiment, sedimentation velocity centrifugation is performed at about 20,000 RPM, about 20° C., and about 0.003 cm radial step setting, with no delay and with no replicates. As noted below, different parameters may be used for centrifugation. In some embodiments, absorbance (260 nm) and/or interference optics (e.g., Rayleigh interference optics) are used to simultaneously record radial concentration as a function of time until the smallest sedimenting component clears the optical window. In some embodiments, the radial concentration is recorded until the sedimenting species with the lowest density clears the sector. In some embodiments, sedimentation is monitored until the recombinant viral particles with the lowest density sediments to the bottom of a sector of an ultracentrifuge. A sector may be a portion of an ultracentrifuge; for example an ultracentrifuge velocity cell. In some embodiments, a sector may be a portion of an ultracentrifuge where samples are detected. In some embodiments, the ultracentrifugation utilizes an ultracentrifuge comprising an ultracentrifuge velocity cell. In some embodiments, is monitored until recombinant viral particles sediment to the bottom of an ultracentrifuge velocity cell. In some embodiments, sedimentation is monitored until the recombinant viral particles with the lowest density sediments and clears the optical window. In some embodiments, the radial concentration is recorded for at least about any of 0.5 hours, 0.75 hours, 1.0 hours, 1.5 hours, 2.0 hours, 3.0 hours, 4.0 hours, or 5.0 hours. In some embodiments, the radial concentration is recorded for about 1.2 hours. Optimizing runs conditions may include, for example, continuing the run until all of the sedimenting species are fully sedimented to the bottom of the sector, with the temperature held constant at 20° C. and a speed between 18,000 rpm and 20,000 rpm. As noted below, other temperatures and speeds may be used.

The percent full capsid is determined by analyzing a multiple of scans (e.g., 75) from each detection method using the SEDFIT continuous size C(S) distribution model. Second ($2^{nd}$) derivative regularization is applied to the fitting. In some embodiments, the confidence level of F statistic is about 0.68. In some embodiments, the confidence level of F statistic is more than about any of 0.68, 0.70, 0.75, 0.80, 0.85, 0.90, 0.95 or 0.99, or any value therebetween. In some embodiments, the following C(S) parameters are held constant: resolution of about 200S to about 5000S, S min is about 1S to about 100S, S max is about 100S to about 5000S, and frictional ratio is about 1.0 or is left to float to a value determined by centrifugation software. In some embodiments, the resolution is about any of 200S, 300S, 400S, 500S, 600S, 700S, 800S, 900S, or 1000S or any value therebetween. In some embodiments, the resolution is about 200S. In some embodiments, the Smax is about any of 100S, 200S, 300S, 400S, 500S, 600S, 700S, 800S, 900S, or 1000S or any value therebetween. In some embodiments, wherein Smax is about 200S. In some embodiments, the frictional ratio is left to float to a value determined by centrifugation software. In some embodiments, the frictional ratio is about 1.0. In some embodiments, radial invariant (RI) and time invariant (TI) noise subtractions are applied. In some embodiments, the meniscus position is allowed to float, letting the software choose the optimal position. In some embodiments, the frictional ratio is allowed to float, letting the software choose the optimal position. The model fits the data to the Lamm equation, and the resulting size distribution is a "distribution of sedimentation coefficients" that looks like a chromatogram with the area under each peak proportional to concentration in units of Fringes or $OD_{260}$ units. The sedimentation coefficient (in Svedberg units) and the relative concentration (in OD units) are determined for each component in the distribution. In some embodiments, multiple AUC runs are independent assays, and each analysis the following attributes are monitored to ensure quality of results: goodness of fit (rmsd), the ratio of $OD_{260\ nm}$/interference signal in fringes (A260/IF ratio) for each peak, consistency of sedimentation coefficients for each species between runs, and overall quality of the scans.

In some embodiments of the invention, extinction coefficients are used to calculate molar concentration and the actual percent value of the intact vector peak from absorbance data. Molar absorbance extinction coefficients for both empty capsids ($\epsilon_{260}/_{capsid}$=3.72e6) and intact vector ($\epsilon_{260}/_{vector}$=3.00e7) can be calculated based on published formulae (Sommer et al. (2003) *Mol Ther.*, 7:122-8).

Extinction coefficients are available for empty capsid and intact vector peaks. The C(S) values can be determined using the SEDFIT algorithm described by Schuck (2000) *Biophys. J.*, 78:1606-19. Molar concentration of both intact vector and empty capsid can be calculated using Beer's Law and the percentage of full capsid are calculated from these values. In some embodiments, values are reported in terms of the percentage of full capsid.

In some embodiments, it is not possible to determine empirically the extinction coefficient of particular species of recombinant viral particles (e.g., viral particles with fragmented genomes of unknown size and sequence). A relationship between S value and genome size may be established by analyzing recombinant viral vector preps with encapsidated viral genomes of known nucleotide size and a corresponding S value are determined as described herein. The calculated S values can be plotted to generate a standard curve to which recombinant viral species of unknown molecular weight or genome size can be compared to determine the molecular weight of the unknown species.

In some aspects, a preparation of recombinant viral particles (e.g., rAAV particles) is characterized by a) subjecting the preparation to analytical ultracentrifugation under boundary sedimentation velocity conditions wherein the sedimentation of recombinant viral particles is monitored at time intervals (e.g., one or more times), b) plotting the differential sedimentation coefficient distribution value (C(s)) versus the sedimentation coefficient in Svedberg units (S), c) integrating the area under each peak in the C(s) distribution to determine the relative concentration of each peak, wherein each peak represents a species of recombinant viral particle. In some embodiments, the species of recombinant viral particle identified include, but are not limited to: full recombinant viral particles comprising intact recombinant viral genomes, empty recombinant viral capsid particles, and recombinant viral particles comprising variant recombinant viral genomes. In some embodiments the variant genomes are smaller than the intact recombinant viral genome (e.g., truncated genomes). In some embodiments, the variant genomes are larger than the intact recombinant viral genome (e.g., aggregates, recombinants, etc.). In some embodiments, a preparation of recombinant viral particles (e.g., rAAV particles) is characterized by a) subjecting the preparation to analytical ultracentrifugation under boundary sedimentation velocity conditions wherein the sedimentation of recombinant viral particles is monitored at time intervals (e.g., one or more times), b) plotting the differential sedimentation coefficient distribution value C(s) versus the sedimentation coefficient in Svedberg units (S), c) identifying species of recombinant viral particles in the preparation by presence of peaks on the plot corresponding to an S value, wherein the genome size of a particular species of recombinant viral particles is calculated by comparing the S value of the species to a standard curve generated by S values of recombinant viral particles comprising encapsidated viral genomes of different known size. In some embodiments, the methods further comprise integrating the area under each peak in the C(S) distribution to determine the relative concentration of each species of recombinant viral particles. In some embodiments, the sedimentation of recombinant viral particles is monitored at one time interval. In some embodiments, the sedimentation of recombinant viral particles is monitored at more than one time interval.

In some embodiments, the sedimentation of recombinant viral particles (e.g., rAAV particles) is monitored by measuring optical density or absorbance at about 260 nm. Means of measuring absorbance are known in the art. In some embodiments, an ultracentrifuge used for AUC is equipped with means for measuring absorbance. In other embodiments, the sedimentation of recombinant viral particles is monitored by interference. In some embodiments, the sedimentation of recombinant viral particles is monitored by Rayleigh interference. Means of measuring interference are known in the art (Furst (1997) Eur. Biophys. J. 35:307-10). In some embodiments, an ultracentrifuge used for AUC is equipped with means for measuring interference. In some embodiments, the sedimentation of recombinant viral particles is monitored by both absorbance and interference. In some embodiments, the absorbance and/or interference are measured using a reference standard. In some embodiments, the reference standard matches the solution of the recombinant viral preparation with the exception that the recombinant viral is not present. For example, the recombinant viral preparation may comprise recombinant viral in a buffer such as phosphate buffered saline. In this example, the reference standard may be phosphate buffered saline without recombinant viral particles.

In some embodiments, the sedimentation velocity of viral particles during ultracentrifugation is determined by monitoring the sedimentation of viral particles continuously during ultracentrifugation. It is within the purview of the skilled artisan to optimize the parameters of AUC for different types of viral particles. In some embodiments, data acquisition for rAAV particles is performed with an AUC speed of between about 3,000 and about 20,000 rpm. In some embodiments, data analysis for rAAV particles is performed with an $S_{min}$ of about 1S and an $S_{max}$ of about 1000S. In some embodiments, data analysis for rAAV particles is performed with a resolution of about 200S to about 1,000S. In some embodiments, the resolution is about any of 200S, 300S, 400S, 500S, 600S, 700S, 800S, 900S, or 1000S or any value therebetween. In some embodiments, the resolution is about 200S. In some embodiments, data analysis for rAAV particles is performed with an $S_{max}$ of about any of 100S, 200S, 300S, 400S, 500S, 600S, 700S, 800S, 900S, or 1000S or any value therebetween. In some embodiments, $S_{max}$ is about 200S to about 5000S. In some embodiments, wherein $S_{max}$ is about 200S. In some embodiments, radial invariant (RI) and time invariant (TI) noise subtractions are applied. In some embodiments, the meniscus position is allowed to float, letting the software choose the optimal position. In some embodiments, the frictional ratio is allowed to float, letting the software choose the optimal position. In some embodiments, data analysis for rAAV particles is held constant at 1. In some embodiments, data analysis for rAAV particles is allowed to float by using the FIT command with a value optimized using non-linear regression.

With respect to recombinant viral particles (e.g., rAAV particles), in some embodiments, the sedimentation velocity of recombinant viral during ultracentrifugation is determined by monitoring (e.g., scanning) the sedimentation of recombinant viral particles once in more than about every 15 seconds, 30 seconds, 45 seconds, 1 minute (60 seconds), 2 minutes, 3 minutes, 4 minutes, 5 minutes, 6 minutes, 7 minutes, 8 minutes, 9 minutes, 10 minutes, 15 minutes, 20 minutes, 25 minutes. Scans may be continuously acquired without delay as quickly as the optical systems allow. Interference scans are rapid, and a single scan is complete in ~10-15 seconds, while absorbance scans require ~60 seconds. When dual detection is used the speed of scan acquisition for both are determined by the absorbance system. In some embodiments of the invention, more than about 5, 10, 15, 20, 25, 30, 35, 40, 45, 50, 55, 60, 65, 70, 75, 80, 85, 90, 95, or 100 scans are used to monitor sedimentation of recombinant viral particles during ultracentrifugation. In some embodiments, a minimum of 30 scans is required for analysis, and scans are collected until the sedimentation process is complete. In some embodiments, the sedimentation process may typically be described by between 40 and 75 scans. In some embodiments, the sedimentation velocity of recombinant viral particles is determined based on about 75 scans. In some embodiments, the sedimentation velocity of recombinant viral particles is determined based on about 55 scans to about 75 scans. In some embodiments, the sedimentation velocity of recombinant viral particles is determined based on about 55 scans to about 60 scans. In some embodiments, the sedimentation velocity of recombinant viral particles is determined based on about 60 scans to about 75 scans. In some embodiments, the sedimentation velocity of recombinant viral particles is determined based on about 60 scans to about 70 scans. In some embodiments, the sedimentation velocity of recombinant viral particles is determined based on multiple ultracentrifugations (runs). In some embodiments, the sedimentation velocity of recombinant viral particles is determined based on any of 1, 2, 3, 4, 5, 6, 7, 8, 9, 10 or more ultracentrifugation runs. In some embodiments, the sedimentation velocities are used to determine C(S) values using the SEDFIT algorithm. In some embodiments, a second derivative regularization is applied to a fitting level with a confidence level of F statistic of about 0.68. In some embodiments, the following C(S) parameters are held constant: resolution 100S to about 200S, S min is about 1, S max is about 200S to 300S, and frictional ratio is about 1.0 to 1.2S. In some embodiments, radial invariant (RI) and time invariant (TI) noise subtractions are applied.

In some embodiments, the boundary sedimentation velocity of recombinant viral particles (e.g., rAAV particles) in a preparation of recombinant viral particles is determined by ultracentrifuging the preparation of recombinant viral particles at more than about any of 5,000 rpm; 10,000 rpm; 15,000 rpm; 20,000 rpm; 25,000 rpm; 30,000 rpm; 35,000 rpm; 40,000 rpm; 45,000 rpm; or 50,000 rpm or any value therebetween. In some embodiments of the invention, the boundary sedimentation velocity of recombinant viral particles in a preparation of recombinant viral particles is determined by ultracentrifuging the preparation of recombinant viral particles at about 20,000 rpm. In some embodiments of the invention, the boundary sedimentation velocity of recombinant viral particles in a preparation of recombinant viral particles is determined by ultracentrifuging the preparation of recombinant viral particles at about 15,000 rpm to about 20,000 rpm.

In some embodiments, the boundary sedimentation velocity of recombinant viral particles in a preparation of recombinant viral particles (e.g., rAAV particles) is determined by ultracentrifuging the preparation of recombinant viral particles at about or more than 4° C., 10° C., 15° C., 20° C., 25° C., or 30° C. or any temperature therebetween. In some embodiments, the boundary sedimentation velocity of recombinant viral particles in a preparation of recombinant viral particles is determined by ultracentrifuging the preparation of recombinant viral particles at about 20° C. In some embodiments, the boundary sedimentation velocity of recombinant viral particles in a preparation of recombinant viral particles is determined by ultracentrifuging the preparation of recombinant viral particles at about 15° C. to about 20° C.

Viral Particles with Enhanced Expression

In some aspects, the invention provides viral particles comprising oversized vector genomes with enhanced expression. In some embodiments, oversized rAAV genomes display enhanced expression when packaged in AAV particles using a producer cell line compared to AAV particles prepared by transient transfection of cells. In some embodiments the invention provides methods for enhancing the expression of an oversized rAAV genome, the method comprising producing rAAV particles in a producer cell line by providing AAV helper functions to the cell line, wherein the producer cell line comprises a) nucleic acid encoding AAV rep and cap genes, and b) a rAAV genome, wherein the rAAV genome is greater than about 4.7 kb. In some embodiments, expression of the oversized rAAV genome is about 1.25-fold, about 1.5-fold, about 1.75-fold, about 2.0-fold, about 2.25-fold, about 2.5-fold, about 2.75-fold, about 3-fold, about 3.25-fold, about 3.5-fold, about 3.75-fold, about 4-fold, about 4.25-fold, about 4.5-fold, about 4.75-fold, or about 5-fold greater than expression of the oversized rAAV genome when produced by transient transfection. In some embodiments, enhanced expression of an oversized rAAV genome is faster expression kinetics compared to the expression kinetics of the oversized rAAV genome from AAV particles produced by transient transfection. In some embodiments, the faster expression kinetics is a faster increase in expression of the oversized rAAV genome over time following delivery of an AAV particle comprising an oversized rAAV genome to a cell. In some embodiments, the faster expression kinetics is a faster time to reach maximum or steady state expression levels of the oversized rAAV genome following delivery of an AAV particle comprising the oversized rAAV genome to a cell compared to expression levels of the oversized rAAV genome following delivery of an AAV particle comprising the oversized rAAV genome from rAAV particles prepared by transient transfection. In some embodiments, the expression kinetics of the oversized rAAV genome produced by a producer cell line is about any of 5%, 10%, 15%, 20%, 25%, 30%, 35%, 40%, 45%, 50%, 55%, 60%, 65%, 70%, 75%, 80%, 85%, 90%, 95%, or 100% faster than expression kinetics of the oversized rAAV genome from rAAV particles produced by transient transfection. In some embodiments, the oversized vector genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.2 kb, 9.3 kb or 9.4 kb in length or any value therebetween.

Heterologous Transgenes

In some embodiments, the viral particle is a recombinant AAV particle comprising an oversized vector genome comprising a heterologous nucleic acid (e.g., a heterologous transgene) flanked by one or two AAV inverted terminal repeats (ITRs). The nucleic acid is encapsidated in the AAV particle. In some embodiments, a rAAV genome of the present disclosure contains one or more AAV inverted terminal repeats (ITRs) and a heterologous transgene. For example, in some embodiments, a rAAV genome of the present disclosure contains two AAV inverted terminal repeats (ITRs). In certain embodiments, a rAAV genome of the present disclosure contains two AAV inverted terminal repeats (ITRs) and a heterologous transgene. In some embodiments, the vector genome is between about 4.7 kb and about 9.4 kb, optionally about 4.7 kb and 6.7 kb. In some embodiments, the vector genome is greater than about 5 kb. In some embodiments, the vector genome is between about 5 kb and about 7 kb, between about 4.7 kb and about 9.4 kb, or between about 4.7 kb and 6.7 kb, or any value therebetween. In some embodiments, the vector genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.2 kb, 9.3 kb or 9.4 kb in length or any value therebetween.

In some embodiments, the heterologous transgene encodes a therapeutic transgene product. In some embodiments, the therapeutic transgene product is a therapeutic polypeptide. A therapeutic polypeptide may, e.g., supply a polypeptide and/or enzymatic activity that is absent or present at a reduced level in a cell or organism. Alternatively, a therapeutic polypeptide may supply a polypeptide and/or enzymatic activity that indirectly counteracts an imbalance in a cell or organism. For example, a therapeutic polypeptide for a disorder related to buildup of a metabolite caused by a deficiency in a metabolic enzyme or activity may supply a missing metabolic enzyme or activity, or it may supply an alternate metabolic enzyme or activity that leads to reduction of the metabolite. A therapeutic polypeptide may also be used to reduce the activity of a polypeptide (e.g., one that is overexpressed, activated by a gain-of-function mutation, or whose activity is otherwise misregulated) by acting, e.g., as a dominant-negative polypeptide.

In some embodiments, the heterologous transgene encodes Factor VIII. In some embodiments, the Factor VIII is a human Factor VIII coding sequence, including without limitation any coding sequence expressed by a human Factor VIII gene. The human Factor VIII gene (e.g., GenBank Entrez Gene ID 2157) is also known as AHF, F8, F8B, F8C, HEMA, FVIII, and DXS1253E. In some embodiments, Factor VIII has the amino acid sequence of human Factor VIII (e.g., as represented by GenBank Accession No. AAA52484). A heterologous transgene encoding Factor VIII may be used, for example, to express Factor VIII in an individual suffering from hemophilia A, a recessive, X-linked coagulation disorder associated with a deficiency in Factor VIII. Factor VIII is known to participate in blood coagulation as part of the intrinsic blood coagulation pathway and is normally expressed by the liver sinusoidal cells and endothelial cells throughout the body.

In some embodiments, the heterologous transgene encodes dystrophin. In some embodiments, the dystrophin is a human dystrophin coding sequence, including without limitation any coding sequence expressed by a human dystrophin gene. The human dystrophin gene (e.g., GenBank Entrez Gene ID 1756) is also known as DMD, BMD, CMD3B, MRX85, DXS142, DXS164, DXS206, DXS230, DXS239, DXS268, DXS269, DXS270, and DXS272. In some embodiments, dystrophin has the amino acid sequence of human dystrophin (e.g., as represented by GenBank Accession No. AAA53189). A heterologous transgene encoding dystrophin may be used, for example, to express dystrophin in an individual suffering from Duchenne or Becker muscular dystrophy, recessive, X-linked muscular dystrophies associated with mutations in dystrophin. Becker muscular dystrophy is a less severe disorder caused by loss of function mutations in dystrophin, whereas Duchenne muscular dystrophy is associated with more severe loss of function or null mutations (e.g., nonsense or frameshift mutations) in dystrophin. Dystrophin is known to function in the dystrophin-glycoprotein complex (DGC), which is required to connect the F-actin of muscle cells to the extracellular matrix, thereby stabilizing the sarcolemma during muscle contraction and relaxation.

In some embodiments, the heterologous transgene encodes cystic fibrosis transmembrane conductance regulator (CFTR), also known as ATP-binding cassette subfamily C, member 7. In some embodiments, the CFTR is a human CFTR coding sequence, including without limitation any coding sequence expressed by a human CFTR gene. The human CFTR gene (e.g., GenBank Entrez Gene ID 1080) is also known as CF, MRP7, ABC35, ABCC7, CFTR/MRP, TNR-CFTR, and dj760C5.1. In some embodiments, CFTR has the amino acid sequence of human CFTR (e.g., as represented by GenBank Accession No. NP_000483). A heterologous transgene encoding CFTR may be used, for example, to express CFTR in an individual suffering from cystic fibrosis, an autosomal, recessive disorder associated with mutations in CFTR that affects the lungs, pancreas, intestines, and many other organs. CFTR is known to function as an ATP-gated ion channel involved in Cl⁻ ion transport. The absence of sufficient CFTR function leads to multiple pathologies; one example is that ion transport across epithelial cells is disrupted, leading to increased cellular water absorption and the pathological thickening and buildup of mucus in the lungs and other tissues.

In some embodiments, the therapeutic transgene product is a therapeutic nucleic acid. In some embodiments, a therapeutic nucleic acid may include without limitation an siRNA, an shRNA, an RNAi, an miRNA, an antisense RNA, a ribozyme or a DNAzyme. As such, a therapeutic nucleic acid may encode an RNA that when transcribed from the nucleic acids of the vector can treat a disorder by interfering with translation or transcription of an abnormal or excess protein associated with the disorder. For example, the heterologous transgene may encode an RNA which treats a disorder by highly specific elimination or reduction of mRNA encoding the abnormal and/or excess proteins. Therapeutic RNA sequences include RNAi, small inhibitory RNA (siRNA), micro RNA (miRNA), and/or ribozymes (such as hammerhead and hairpin ribozymes) that can treat disorders by highly specific elimination or reduction of mRNA encoding the abnormal and/or excess proteins.

In some embodiments, the heterologous transgene is a human transgene. In some embodiments, the heterologous transgene is linked to a promoter. In some embodiments, the transgene (e.g., a heterologous nucleic acid described herein) is operably linked to a promoter. Exemplary promoters include, but are not limited to, the cytomegalovirus (CMV) immediate early promoter, the GUSB promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., *Gene,* 1991, 108(2):193-9) and the elongation factor 1-alpha promoter (EF1-alpha) promoter (Kim et al., *Gene,* 1990, 91(2):217-23 and Guo et al., *Gene Ther.,* 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the promoter is a mouse transthyretin promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1a promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., *Proc. Natl. Acad. Sci. USA,* 93:3346-3351 (1996)), the tetracycline-repressible system (Gossen et al., *Proc. Natl. Acad. Sci. USA,* 89:5547-5551 (1992)), the tetracycline-inducible system (Gossen et al., *Science,* 268:1766-1769 (1995), see also Harvey et al., *Curr. Opin. Chem. Biol.,* 2:512-518 (1998)), the RU486-inducible system (Wang et al., *Nat. Biotech.,* 15:239-243 (1997) and Wang et al., *Gene Ther.,* 4:432-441 (1997)) and the rapamycin-inducible system (Magari et al., *J. Clin. Invest.,* 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter, or fragment thereof, for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. For example, tissue-specific expression in the liver, lungs, muscle, intestine, pancreas, and/or other tissues may be desired. Appropriate tissue-specific regulatory sequences (e.g., promoters, enhancers, etc.) are well known in the art. For example, in some embodiments, the promoter is a mouse transthyretin (mTTR) promoter, which is known to drive gene expression in the liver.

In some embodiments, the rAAV genome includes an intron. In some embodiments, the intron is a hybrid intron.

In some embodiments, the rAAV genome includes a polyadenylation signal. Many polyadenylation signals are known in the art. In some embodiments, the polyadenylation signal is a synthetic polyadenylation signal. In other embodiments, the polyadenylation signal is a bovine growth hormone (BGH) polyadenylation signal. For a more detailed description of the BGH polyadenylation signal, see, e.g., Goodwin, E. C. and Rottman, F. M. (1992) *J. Biol. Chem.* 267:16330-16334.

In some embodiments, the invention provides AAV particles comprising an oversized AAV genome, wherein the AAV genome comprises 5' to 3' and AAV2 ITR, an mTTR202 promoter, a hybrid intron, a B-domain deleted Factor VIII transgene, a synthetic polyadenylation signal and an AAV2 ITR. In some embodiments, the oversized AAV genome comprises 5' to 3' and AAV2 ITR, an mTTR202opt promoter, a hybrid intron, a B-domain deleted Factor VIII transgene, a synthetic polyadenylation signal and an AAV2 ITR. In some embodiments, the oversized AAV genome comprises 5' to 3' and AAV2 ITR, an mTTR482 promoter, a hybrid intron, a B-domain deleted Factor VIII transgene, a synthetic polyadenylation signal and an AAV2 ITR. In some embodiments, the oversized AAV genome comprises 5' to 3' and AAV2 ITR, an mTTR482 promoter, a hybrid intron, a B-domain deleted Factor VIII transgene, a bovine growth hormone polyadenylation signal and an AAV2 ITR.

The rAAV genome elements described above (e.g., a promoter, an intron, and a polyadenylation signal) may be present alone or in any combination with a heterologous transgene of the present disclosure. The rAAV genome may include any element to establish the expression of a heterologous transgene, for example, a promoter, a heterologous nucleic acid, an ITR, a ribosome binding element, terminator, enhancer, selection marker, intron, a polyadenylation (polyA) signal, and/or origin of replication. For example, in some embodiments, the rAAV genome contains a heterologous transgene and one or more elements selected from a promoter of the present disclosure, an intron of the present disclosure, and a polyadenylation signal of the present disclosure. In some embodiments, the rAAV genome may include at least one ITR sequence flanking a heterologous transgene and one or more elements selected from a promoter of the present disclosure, an intron of the present disclosure, and a polyadenylation signal of the present disclosure.

In some embodiments, the oversized rAAV vector is a self-complementary rAAV vector, e.g., one that comprises a recombinant self-complementing (the term "self-complementary may be used interchangeably herein) genome. AAV viral particles with self-complementing genomes and methods of use of self-complementing AAV genomes are described in U.S. Pat. Nos. 6,596,535; 7,125,717; 7,465,583; 7,785,888; 7,790,154; 7,846,729; 8,093,054; and 8,361,457; and Wang Z., et al., (2003) Gene Ther 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the vector comprises first nucleic acid sequence encoding the heterologous nucleic acid and a second nucleic acid sequence encoding a complement of the nucleic acid, where the first nucleic acid sequence can form intrastrand base pairs with the second nucleic acid sequence along most or all of its length.

In some embodiments, the first heterologous nucleic acid sequence and a second heterologous nucleic acid sequence are linked by a mutated ITR (e.g., the right ITR). In some embodiments, the ITR comprises the polynucleotide sequence 5'-CACTCCCTCTCTGCGCGC TCGCTCGCT-CACTGAGGCCGGGCGACCAAAGGTCGCCCACGC-CCGGGCTTTGCCC GGGCG-3' (SEQ ID NO:24). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR. In some embodiments, the scAAV vector genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, or 7.0 kb or any value therebetween.

IV. Methods of Producing Viral Particles

Certain aspects of the present disclosure relate to methods for producing an adeno-associated virus (AAV) particle containing an oversized recombinant AAV genome. In some embodiments, the methods include culturing an AAV producer cell line under conditions to generate rAAV particles, where the AAV producer cell line comprises i) nucleic acid encoding AAV rep and cap genes, and ii) a rAAV genome, where the rAAV genome is between about 4.7 kb and about 9.4 kb, optionally about 4.7 kb and 6.7 kb; b) providing AAV helper functions; and c) collecting the rAAV particles containing oversized rAAV genomes. In some embodiments, the AAV producer cell line comprises stably maintained nucleic acid encoding AAV rep and cap genes. In some embodiments, the AAV producer cell line comprised a stably maintained a rAAV genome, where the rAAV genome between about 4.7 kb and about 9.4 kb, optionally about 4.7 kb and 6.7 kb. In some embodiments, the AAV producer cell line comprises stably maintained nucleic acid encoding AAV rep and cap genes and a stably maintained a rAAV genome, where the rAAV genome is between about 4.7 kb and about 9.4 kb, optionally about 4.7 kb and 6.7 kb. In some embodiments, the AAV producer cell line comprises nucleic acid encoding AAV rep and cap genes stably integrated into the cell line genome. In some embodiments, the AAV producer cell line comprised a rAAV genome stably integrated into the cell line genome, where the rAAV genome is between about 4.7 kb and about 9.4 kb, optionally about 4.7 kb and 6.7 kb. In some embodiments, the AAV producer cell line comprises nucleic acid encoding AAV rep and cap genes and a rAAV genome stably integrated into the cell line genome, where the rAAV genome is between about 4.7 kb and about 9.4 kb, optionally about 4.7 kb and 6.7 kb. In some embodiments of the above embodiments, the rAAV genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.2 kb, 9.3 kb or 9.4 kb in length or any value therebetween. In some embodiments, the packaged AAV genome did not contain a truncation of the 5' end. In some embodiments, the packaged AAV genome did not contain a truncation of the 3' end.

Other aspects of the present disclosure relate to cell lines for producing an adeno-associated virus (AAV) particle comprising an oversized recombinant AAV genome, the cell line including a) nucleic acid encoding AAV rep and cap genes, and b) a rAAV genome, wherein the rAAV genome is between about 4.7 kb and about 9.4 kb, optionally about 4.7 kb and 6.7 kb. In some embodiments, the AAV producer cell line comprises stably maintained nucleic acid encoding AAV rep and cap genes. In some embodiments, the AAV producer cell line comprised a stably maintained a rAAV genome, where the rAAV genome is between about 4.7 kb and about 9.4 kb, optionally about 4.7 kb and about 6.7 kb or about 5.2 kb to about 8.7 kb. In some embodiments, the AAV producer cell line comprises stably maintained nucleic acid encoding AAV rep and cap genes and a stably maintained a rAAV genome, where the rAAV genome between about 4.7 kb and about 9.4 kb, optionally about 4.7 kb and about 6.7 kb or about 5.2 kb to about 8.7 kb. In some embodiments, the AAV producer cell line comprises nucleic acid encoding AAV rep and cap genes stably integrated into the cell line genome. In some embodiments, the AAV producer cell line comprised a rAAV genome stably integrated into the cell line genome, where the rAAV genome is between about 4.7 kb and about 9.4 kb, optionally about 4.7 kb and about 6.7 kb or about 5.2 kb to about 8.7 kb. In some embodiments, the AAV producer cell line comprises nucleic acid encoding AAV rep and cap genes and a rAAV genome stably integrated into the cell line genome, where the rAAV genome is between about 4.7 kb and about 9.4 kb, optionally about 4.7 kb and about 6.7 kb or about 5.2 kb to about 8.7 kb. In some embodiments, the rAAV genome is greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.2 kb, 9.3 kb or 9.4 kb in length or any value therebetween.

Numerous methods are known in the art for production of rAAV vectors, including transfection, stable cell line production, and infectious hybrid virus production systems which include adenovirus-AAV hybrids, herpesvirus-AAV hybrids (Conway, J E et al., (1997) *J. Virology* 71(11):8780-8789) and baculovirus-AAV hybrids. rAAV production cultures for the production of rAAV virus particles all require; 1) suitable host cells, 2) suitable helper virus function, 3) AAV rep and cap genes and gene products; 4) a nucleic acid (such as a therapeutic nucleic acid) flanked by at least one AAV ITR sequences (e.g., an oversized rAAV vector genome); and 5) suitable media and media components to support rAAV production. In some embodiments, the suitable host cell is a primate host cell. In some embodiments, the suitable host cell is a human-derived cell lines such as HeLa, A549, 293, or Perc.6 cells. In some embodiments, the suitable helper virus function is provided by wild-type or mutant adenovirus (such as temperature sensitive adenovirus), herpes virus (HSV), baculovirus, or a plasmid construct providing helper functions. In some embodiments, the AAV rep and cap gene products may be from any AAV serotype. In general, but not obligatory, the AAV rep gene product is of the same serotype as the ITRs of the rAAV vector genome as long as the rep gene products may function to replicated and package the rAAV genome. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors. In some embodiments, the AAV helper functions are provided by adenovirus or HSV. In some embodiments, the AAV helper functions are provide by baculovirus and the host cell is an insect cell (e.g., *Spodoptera frugiperda* (Sf9) cells).

One method for producing rAAV particles is the triple transfection method. Briefly, a plasmid containing a rep gene and a capsid gene, along with a helper adenoviral plasmid, may be transfected (e.g., using the calcium phosphate method) into a cell line (e.g., HEK-293 cells), and virus may be collected and optionally purified. As such, in some embodiments, the rAAV particle was produced by triple transfection of a nucleic acid encoding the rAAV vector, a nucleic acid encoding AAV rep and cap, and a nucleic acid encoding AAV helper virus functions into a host cell, wherein the transfection of the nucleic acids to the host cells generates a host cell capable of producing rAAV particles.

In some embodiments, rAAV particles may be produced by a producer cell line method, such as the exemplary producer cell line method provided infra (see also Martin et al., (2013) *Human Gene Therapy Methods* 24:253-269; U.S. PG Pub. No. US2004/0224411; and Liu, X. L. et al. (1999) *Gene Ther.* 6:293-299). Briefly, a cell line (e.g., a HeLa, 293, A549, or Perc.6 cell line) may be stably transfected with a plasmid containing a rep gene, a capsid gene, and an oversized vector genome comprising a promoter-heterologous nucleic acid sequence. Cell lines may be screened to select a lead clone for rAAV production, which may then be expanded to a production bioreactor and infected with a helper virus (e.g., an adenovirus or HSV) to initiate rAAV production. Virus may subsequently be harvested, adenovirus may be inactivated (e.g., by heat) and/or removed, and the rAAV particles may be purified. As such, in some embodiments, the rAAV particle was produced by a producer cell line comprising one or more of nucleic acid encoding the rAAV vector, a nucleic acid encoding AAV rep and cap, and a nucleic acid encoding AAV helper virus functions. As described herein, the producer cell line method may be advantageous for the production of rAAV particles with an oversized genome, as compared to the triple transfection method.

In some embodiments, the nucleic acid encoding AAV rep and cap genes and/or the rAAV genome are stably maintained in the producer cell line. In some embodiments, nucleic acid encoding AAV rep and cap genes and/or the rAAV genome is introduced on one or more plasmids into a cell line to generate a producer cell line. In some embodiments, the AAV rep, AAV cap, and rAAV genome are introduced into a cell on the same plasmid. In other embodiments, the AAV rep, AAV cap, and rAAV genome are introduced into a cell on different plasmids. In some embodiments, a cell line stably transfected with a plasmid maintains the plasmid for multiple passages of the cell line (e.g., 5, 10, 20, 30, 40, 50 or more than 50 passages of the cell). For example, the plasmid(s) may replicate as the cell replicates, or the plasmid(s) may integrate into the cell genome. A variety of sequences that enable a plasmid to replicate autonomously in a cell (e.g., a human cell) have been identified (see, e.g., Krysan, P. J. et al. (1989) *Mol. Cell Biol.* 9:1026-1033). In some embodiments, the plasmid(s) may contain a selectable marker (e.g., an antibiotic resistance marker) that allows for selection of cells maintaining the plasmid. Selectable markers commonly used in mammalian cells include without limitation blasticidin, G418, hygromycin B, zeocin, puromycin, and derivatives thereof. Methods for introducing nucleic acids into a cell are known in the art and include without limitation viral transduction, cationic transfection (e.g., using a cationic polymer such as DEAE-dextran or a cationic lipid such as lipofectamine), calcium phosphate transfection, microinjection, particle bombardment, electroporation, and nanoparticle transfection (for more details, see, e.g., Kim, T. K. and Eberwine, J. H. (2010) *Anal. Bioanal. Chem.* 397:3173-3178).

In some embodiments, the nucleic acid encoding AAV rep and cap genes and/or the rAAV genome are stably integrated into the genome of the producer cell line. In some embodiments, nucleic acid encoding AAV rep and cap genes and/or the rAAV genome is introduced on one or more plasmids into a cell line to generate a producer cell line. In some embodiments, the AAV rep, AAV cap, and rAAV genome are introduced into a cell on the same plasmid. In other embodiments, the AAV rep, AAV cap, and rAAV genome are introduced into a cell on different plasmids. In some embodiments, the plasmid(s) may contain a selectable marker (e.g., an antibiotic resistance marker) that allows for selection of cells maintaining the plasmid. Methods for stable integration of nucleic acids into a variety of host cell lines are known in the art (see Examples below for more detailed description of an exemplary producer cell line created by stable integration of nucleic acids). For example, repeated selection (e.g., through use of a selectable marker) may be used to select for cells that have integrated a nucleic acid containing a selectable marker (and AAV cap and rep genes and/or a rAAV genome). In other embodiments, nucleic acids may be integrated in a site-specific manner into a cell line to generate a producer cell line. Several site-specific recombination systems are known in the art, such as FLP/FRT (see, e.g., O'Gorman, S. et al. (1991) *Science* 251:1351-1355), Cre/loxP (see, e.g., Sauer, B. and Henderson, N. (1988) *Proc. Natl. Acad. Sci.* 85:5166-5170), and phi C31-att (see, e.g., Groth, A. C. et al. (2000) *Proc. Natl. Acad. Sci.* 97:5995-6000).

In some embodiments, the producer cell line is derived from a primate cell line (e.g., a non-human primate cell line, such as a Vero or FRhL-2 cell line). In some embodiments, the cell line is derived from a human cell line. In some embodiments, the producer cell line is derived from HeLa, 293, A549, or PERC.6® (Crucell) cells. For example, prior to introduction and/or stable maintenance/integration of nucleic acid encoding AAV rep and cap genes and/or the oversized rAAV genome into a cell line to generate a producer cell line, the cell line is a HeLa, 293, A549, or PERC.6® (Crucell) cell line, or a derivative thereof.

In some embodiments, the producer cell line is adapted for growth in suspension. As is known in the art, anchorage-dependent cells are typically not able to grow in suspension without a substrate, such as microcarrier beads. Adapting a cell line to grow in suspension may include, for example, growing the cell line in a spinner culture with a stirring paddle, using a culture medium that lacks calcium and magnesium ions to prevent clumping (and optionally an antifoaming agent), using a culture vessel coated with a siliconizing compound, and selecting cells in the culture (rather than in large clumps or on the sides of the vessel) at each passage. For further description, see, e.g., ATCC frequently asked questions document (available at www.atcc.org/Global/FAQs/9/1/Adapting%20a%20monolayer%20cell%20line%20to%20suspension-40.aspx) and references cited therein.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication and/or encapsidation protein; (ii) a rAAV pro-vector comprising a nucleic acid encoding a heterologous nucleic acid as described herein flanked by at least one AAV ITR, and (iii) an AAV helper function; and (b) recovering the rAAV particles produced by the host cell. In some embodiments, said at least one AAV ITR is selected from the group consisting of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs or the like. For example, in some embodiments, the AAV serotype is AAV1, AAV2, AAV5, AAV6, AAV7, AAV8, AAVrh8, AAVrh8R, AAV9, AAV10, or AAVrh10. In certain embodiments, the nucleic acid in the AAV comprises an AAV2 ITR. In some embodiments, said encapsidation protein is selected from the group consisting of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, goat AAV, AAV1/AAV2 chimeric, bovine AAV, or mouse AAV capsid rAAV2/HBoV1 serotype capsid proteins or mutants thereof. In some embodiments, the encapsidation protein is an AAV5 capsid protein including AAV5 capsid proteins having tyrosine capsid mutations. In some embodiments, the encapsidation protein is an AAV5 capsid protein including AAV5 capsid proteins having tyrosine capsid mutations and the ITR is an AAV2 ITR. In further embodiments, the rAAV particle comprises capsid proteins of an AAV serotype from Clades A-F. In some embodiments, the AAV serotype is AAV1, AAV2, AAV5, AAV6, AAV7, AAV8, AAVrh8, AAVrh8R, AAV9, AAV10, or AAVrh10. In some embodiments, the rAAV particle comprises an AAV serotype 1 (AAV1) capsid. In some embodiments, the rAAV particle comprises an AAV serotype 2 (AAV2) capsid. In some embodiments, the rAAV particle comprises an AAVrh8R capsid or mutant thereof. In some embodiments, the rAAV particles comprise an AAV1 capsid and a recombinant genome comprising AAV2 ITRs, a mutant AAV2 ITR and nucleic acid encoding a therapeutic transgene/nucleic acid. In some embodiments, the AAV ITRs are AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In certain embodiments, the AAV ITRs are AAV2 ITRs. In some embodiments, the ITR is derived from AAV2, and the capsid is derived from AAV2. In some embodiments, the ITR is derived from AAV2, and the capsid is derived from AAVrh8R.

Suitable rAAV production culture media of the present invention may be supplemented with serum or serum-derived recombinant proteins at a level of 0.5%-20% (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components know in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

Certain aspects of the present disclosure relate to collecting the rAAV particles containing oversized rAAV genomes. rAAV vector particles of the invention may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118). Suitable methods of lysing cells are also known in the art and include for example multiple freeze/thaw cycles, sonication, microfluidization, and treatment with chemicals, such as detergents and/or proteases.

In some embodiments, the AAV particles collected contain rAAV genomes greater than about 5.0 kb. In some embodiments, the rAAV particles collected contain rAAV genomes greater than about any of 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, or 7.0 kb, 8.0 kb or 9.0 kb in length or any value therebetween in length. In some embodiments, the rAAV particles collected contain rAAV genomes between any of about 5.0 kb and about 9.0 kb, about 5.0 kb and about 8.5 kb, about 5.0 kb and about 8.0 kb, about 5.0 kb and about 7.5 kb, about 5.0 kb and about 7.0 kb, about 5.0 kb and about 6.5 kb, about 5.0 kb and about 6.0 kb, about 5.0 kb and about 5.5 kb, about 5.2 kb and about 9.0 kb, about 5.2 kb and about 8.5 kb, about 5.2 kb and about 8.0 kb, about 5.2 kb and about 7.5 kb, about 5.2 kb and about 7.0 kb, about 5.2 kb and about 6.5 kb, about 5.2 kb and about 6.0 kb, about 5.2 kb and about 5.5 kb, about 5.5 kb and about 9.0 kb, about 5.5 kb and about 8.5 kb, about 5.5 kb and about 8.0 kb, about 5.5 kb and about 7.5 kb, about 5.5 kb and about 7.0 kb, about 5.5 kb and about 6.5 kb, about 5.5 kb and about 6.0 kb, about 6.0 kb and about 9.0 kb, about 6.0 kb and about 8.5 kb, about 6.0 kb and about 8.0 kb, about 6.0 kb and about 7.5 kb, about 6.0 kb and about 7.0 kb, about 6.0 kb and about 6.5 kb, about 6.5 kb and about 9.0 kb, about 6.5 kb and about 8.5 kb, about 6.5 kb and about 8.0 kb, about 6.5 kb and about 7.5 kb, about 6.5 kb and about 7.0 kb, about 7.0 kb and about 9.0 kb, about 7.0 kb and about 8.5 kb, about 7.0 kb and about 8.0 kb, about 7.0 kb and about 7.5 kb, about 7.5 kb and about 9.0 kb, about 7.5 kb and about 8.5 kb, about 7.5 kb and about 8.0 kb, about 8.0 kb and about 9.0 kb, about 8.0 kb and about 8.5 kb, or about 8.5 kb and about 9.0 kb. In some embodiments, the rAAV particles collected contain rAAV genomes between about 4.7 kb and about 9.4 kb, optionally about 4.7 kb and about 6.7 kb or about 5.2 kb and about 8.7 kb.

In some embodiments, rAAV particles are collected from between about 48 hours and about 96 hours after the provision of helper functions. For example, in some embodiments, rAAV particles are collected about 48 hours, about 60 hours, about 72 hours, about 84 hours, or about 96 hours after the provision of helper functions. In some embodiments, rAAV particles are collected about 48 hours and about 96 hours, about 48 hours and about 84 hours, about 48 hours and about 72 hours, about 48 hours and about 60 hours, about 60 hours and about 96 hours, about 60 hours and about 84 hours, about 60 hours and about 72 hours, about 72 hours and about 96 hours, about 72 hours and about 84 hours, or about 84 hours and about 96 hours after the provision of helper functions.

In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

In some embodiments, the rAAV production culture harvest is clarified to remove host cell debris. In some embodiments, the production culture harvest is clarified by filtration through a series of depth filters including, for example, a grade DOHC Millipore Millistak+HC Pod Filter, a grade A1HC Millipore Millistak+HC Pod Filter, and a 0.2 µm Filter Opticap XL1O Millipore Express SHC Hydrophilic Membrane filter. Clarification can also be achieved by a variety of other standard techniques known in the art, such as, centrifugation or filtration through any cellulose acetate filter of 0.2 µm or greater pore size known in the art.

In some embodiments, the rAAV production culture harvest is further treated with Benzonase® to digest any high molecular weight DNA present in the production culture. In some embodiments, the Benzonase® digestion is performed under standard conditions known in the art including, for example, a final concentration of 1-2.5 units/ml of Benzonase® at a temperature ranging from ambient to 37° C. for a period of 30 minutes to several hours.

rAAV particles may be isolated or purified using one or more of the following purification steps: equilibrium centrifugation; flow-through anionic exchange filtration; tangential flow filtration (TFF) for concentrating the rAAV particles; rAAV capture by apatite chromatography; heat inactivation of helper virus; rAAV capture by hydrophobic interaction chromatography; buffer exchange by size exclusion chromatography (SEC); nanofiltration; and rAAV capture by anionic exchange chromatography, cationic exchange chromatography, or affinity chromatography. In some embodiments, the purification comprises one or more chromatography steps (e.g., one or more of the chromatography steps described above). These steps may be used alone, in various combinations, or in different orders. In some embodiments, the method comprises all the steps in the order as described below. Methods to purify rAAV particles are found, for example, in Xiao et al., (1998) *Journal of Virology* 72:2224-2232; U.S. Pat. Nos. 6,989,264 and 8,137,948; and WO 2010/148143.

In some embodiments, the rAAV particle is in a pharmaceutical composition. In some embodiments, the rAAV particle is in a pharmaceutical composition comprising a pharmaceutically acceptable excipient. As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolarity, encapsulating agents, pH buffering substances, and buffers. Such excipients include any pharmaceutical agent suitable for delivery to a target tissue which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991).

Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

V. Methods of Treatment

In some aspects, the invention provides methods of treating of treating a disease or disorder in an individual in need thereof comprising administering to the individual AAV particles The AAV particles may be administered to a particular tissue of interest, or it may be administered systemically. In some embodiments, an effective amount of the AAV particles may be administered parenterally. Parenteral routes of administration may include without limitation intravenous, intraosseous, intra-arterial, intracerebral, intramuscular, intrathecal, subcutaneous, intracerebroventricular, and so forth. In some embodiments, an effective amount of AAV particles may be administered through one route of administration. In some embodiments, an effective amount of AAV particles may be administered through a combination of more than one route of administration. In some embodiments, the individual is a mammal. In some embodiments, the individual is a human.

An effective amount of AAV particles comprising an oversized AAV genome is administered, depending on the objectives of treatment. For example, where a low percentage of transduction can achieve the desired therapeutic effect, then the objective of treatment is generally to meet or exceed this level of transduction. In some instances, this level of transduction can be achieved by transduction of only about 1 to 5% of the target cells of the desired tissue type, in some embodiments at least about 20% of the cells of the desired tissue type, in some embodiments at least about 50%, in some embodiments at least about 80%, in some embodiments at least about 95%, in some embodiments at least about 99% of the cells of the desired tissue type. As a guide, the number of particles administered per injection is generally between about $1 \times 10^6$ and about $1 \times 10^{14}$ particles, between about $1 \times 10^7$ and $1 \times 10^{13}$ particles, between about $1 \times 10^9$ and $1 \times 10^{12}$ particles or about $1 \times 10^9$ particles, about $1 \times 10^{10}$ particles, or about $1 \times 10^{11}$ particles. The rAAV composition may be administered by one or more administrations, either during the same procedure or spaced apart by days, weeks, months, or years. One or more of any of the routes of administration described herein may be used. In some embodiments, multiple vectors may be used to treat the human.

Methods to identify cells transduced by AAV viral particles are known in the art; for example, immunohistochemistry or the use of a marker such as enhanced green fluorescent protein can be used to detect transduction of viral particles; for example viral particles comprising a rAAV capsid with one or more substitutions of amino acids.

In some embodiments the AAV viral particles comprising an oversized AAV genome with are administered to more than one location simultaneously or sequentially. In some embodiments, multiple injections of rAAV viral particles are no more than one hour, two hours, three hours, four hours, five hours, six hours, nine hours, twelve hours or 24 hours apart.

In some embodiments, the invention provides methods of treatment of a disease or disorder in an individual comprising administering an AAV particle comprising an oversized AAV genome, wherein the oversized AAV genome comprises a transgene suitable for treating the disease of disorder. In some embodiments, the invention provides methods for treating hemophilia A with an AAV particle comprising an oversized AAV genome encoding a Factor VIII transgene (e.g., a human factor VIII transgene). In some embodiments, the invention provides methods for treating muscular dystrophy with an AAV particle comprising an oversized AAV genome encoding a dystrophin transgene (e.g., a human dystrophin transgene). In some embodiments, the invention provides methods for treating dysferlinopathy with an AAV particle comprising an oversized AAV genome encoding a dysferlin transgene (e.g., a human dysferlin transgene). In some embodiments, the invention provides methods for treating cystic fibrosis with an AAV particle comprising an oversized AAV genome encoding a CFTR transgene (e.g., a human CFTR transgene). The invention is not limited, however, to diseases or disorders which require expression of a transgene greater than what fits in a 4.8 kb AAV vector genome. For example, in some embodiments, the invention provides AAV particles comprising an AAV genome comprising one or more heterologous transgenes wherein the combination of heterologous transgene and regulatory factors (promoters, enhances, introns, etc) results in an AAV genome greater than about 5.0 kb.

VI. Kits

In some embodiments, the invention comprises kits comprising the AAV particles comprising oversized genomes of the invention. In some embodiments, the kits further comprise a device for delivery (e.g., parenteral administration) of compositions of rAAV particles. In some embodiments, the instructions for use include instructions according to one of the methods described herein. In some embodiments, the instructions are printed on a label provided with (e.g., affixed to) a container. In some embodiments, the instructions for use include instructions for treating a disease or disorder.

In some embodiments, the kit comprises a single fluid (e.g., a pharmaceutically acceptable fluid comprising an effective amount of the vector). In some embodiments, the kit comprises 2 or more fluids. A fluid may include a diluent, buffer, excipient, or any other liquid described herein or known in the art suitable for delivering, diluting, stabilizing, buffering, or otherwise transporting a AAV particle of the present disclosure. In some embodiments, the system comprises one or more buffers, e.g., an aqueous pH buffered solution. Examples of buffers may include without limitation phosphate, citrate, Tris, HEPES, and other organic acid buffers.

In some embodiments, the kit comprises a container. Suitable containers may include, e.g., vials, bags, syringes, and bottles. The container may be made of one or more of a material such as glass, metal, or plastic. In some embodiments, the container is used to hold a rAAV composition of the present disclosure. In some embodiments, the container may also hold a fluid and/or other therapeutic agent.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Generation of Producer Cell Lines with an Oversized 5.1 kb and 5.4 kb FVIII Vectors As discussed above, a need exists for a platform capable of producing rAAV vectors having oversized genomes with high yields, uniform product, and high quality genomes. This Example describes the generation of a producer cell line (PCL) platform that is particularly advantageous for producing rAAV vectors with genomes containing large constructs (e.g., over 5 kb).

Methods

Construction of pTP Plasmid for Oversized 5.1 and 5.4 kb FVIII Vectors

FVIII expression cassettes were generated in pUC57-based plasmids and consisted of mouse transthyretin (mTTR) promoter (Costa, R H et al., *Mol Cell Biol* 1986, 6:4697-4708.) (202 bp core sequence with and without 100 bp enhancer sequencer), hybrid intron (Jiang, H. et al., *Blood* 2006 108:107-115), codon-optimized human B-domain deleted FVIII cDNA, synthetic or BGH polyA and rAAV2 inverted terminal repeat sequences. These generated rAAV vectors with vector genome sizes ranging from 5.1 and 5.4 kb (FIG. 1A).

Plasmid vectors with FVIII expression cassettes were tested for FVIII production in vivo by high volume injection into normal C57BL/6 mice. To generate producer cell line (PCL) for AAVrh8R/5.1 kb FVIII vector, a TriplePlay plasmid, pAFTGEN-SEAP-caprh8R, was digested with BglII, and blunt-ended. The FVIII vector genome with flanking 5' and 3' AAV2 ITRs were excised from pUC57-mTTR-hFVIIIco (pITR-mTTR-hFVIIISQco-SpA) using PvuI and SapI sites. The 5.5 kb PvuI/SapI blunted fragment was ligated to the TriplePlay plasmid to generate plasmid with 5.1 kb FVIII vector and AAVrh8R cap gene. A similar construct was generated containing AAV8 cap gene. A TriplePlay plasmid with AAVrh8R cap gene and 5.4 kb vector was made by replacing a synthetic polyA region with bovine growth hormone (BGH) polyA. The resulting kanamycin resistant clones were transfected into Huh7 cells to test FVIII protein production.

Quantitation of FVIII levels in media by standard ELISA assay confirmed FVIII production from selected TriplePlay plasmids. rAAV vector generation from selected TriplePlay plasmids (pTGEN/AAVrh8R/mTTRhFVIII or pTGEN/AAV8/mTTRhFVIII) was tested by co-transfection of pAd-helper into 293 cells. Cell lysates were harvested and qPCR with FVIII primer/probe was performed to quantify the amount of packaged genomes.

Primers and probes used in the Examples presented herein are found in Table 1.

Generation of Producer Cell Lines for 5.1 kb and 5.4 kb FVIII Vectors

Plasmid pTGEN/AAVrh8R/mTTR-hFVIII (with 5.1 or 5.4 kb vector) or plasmid pTGEN/AAV8/mTTR-hFVIII was transfected with Lipofectamine and Plus reagent into HeLaS3 cells. Cells were plated onto 60×96-well plates and plates were washed and fed weekly. After selection, plates were scored for colony growth. Masterwells (MWs) were harvested and transferred to 24-well dish and were harvested based on size into 24-well dish.

Masterwells were next plated onto 96-well plates for relative production (RP) screen and positive MWs for vector production from RP screens were then tested for specific production (SP) level; e.g., via vector production by qPCR (Martin, J. et al., 2013 *Hum. Gene Ther. Meth.* 24:253-269).

Characterization of Genomic DNA of Producer Cell Lines with 5.1 kb and 5.4 kb FVIII Vectors Genomic DNA was analyzed for copy numbers of vector, rep and puromycin sequences by qPCR using specific primers and probes to each sequence. Additionally, the size and integrity of the integrated "TriplePlay" plasmid were analyzed by Southern blot. For this, genomic DNA was digested with SpeI (single cutter in Tripleplay plasmid) to determine the size of integrated TriplePlay plasmid and with BglII/HincII to look for integrity of vector expression cassette. BglII/HincII digestion cuts within mTTR promoter, FVIII cDNA and synthetic polyA generate 1.8 and 2.8 kb fragments. Digested genomic DNA and TriplePlay plasmid (spiked into genomic DNA and used as copy number and size markers) were run on 0.8% agarose gel. DNA was transferred onto nylon membrane and probed with DIG-labeled FVIII NcoI fragment.

Characterization of AAV/mTTR-hFVIII Vector Production from Producer Cell Lines

Selected MWs were analyzed for rAAV vector production. For comparison, the 5.1 and 5.4 kb FVIII vectors were made by triple transfection production method by transfecting plasmid pUC57-mTTR-hFVIIIco into 293 cells. Cells were harvested, lysed and purification was performed comparable to producer cell line method. Samples from both methods were quantitated for vector genomes copies by qPCR and virus recoveries and yields were calculated. Vector lots were characterized by SDS-PAGE analysis of capsids, AUC analysis, and for packaged genome sizes (see below).

Characterization of rAAV/mTTR-hFVIII Vector Genomes Generated from Producer Cell Lines Packaged vector genomes (VGs) were extracted from purified capsids as follows. Virus was incubated with 110 U of DNAse (Promega) 37° C. for 1 h. EDTA was added to stop digestion followed by incubation with proteinase K digestion with presence of N-lauryl sarcosyl 50° C. for 45 min. DNA was extracted twice with phenol:chloroform:isoamyl alcohol (25:24:1) and centrifuged at 14,000 rpm at 4° C. for 10 min. The DNA was precipitated with 100% ethanol and 3 M sodium acetate T −80° C. for 1 h, centrifuged for 1 h. DNA and the pellet resuspended in TE.

For Southern analysis, genomes were separated by 1% alkaline gel electrophoresis in running buffer consisting of 30 mM NaOH and 1 mM EDTA. Samples were transferred and cross-linked onto Hybond membrane (Amersham), probed with various fragments specific to FVIII expression cassette. These included a 4.0 kb NheI-XcmI fragment containing all FVIII domains except C2. Additionally, various 25- to 30-mer strand-specific oligonucleotide probes were used. The larger probes were labeled with AlkPhos Direct Labeling system (Amersham). Oligonucleotide probes were 3'end-labeled using DIG Oligo 3'-End Labeling Kit (Roche) according to the manufacturer's instructions.

For DNA dot blot analysis, VGs were denatured in TE buffer pH 7.0 by heating at 100° C. for 5 min followed by a 5 min chill on ice and manual application to nylon membrane using a multichannel pipette. DNA was fixed to the membrane by UV cross-linking. Hybridization was carried out for each DIG-labeled oligonucleotide probe at 50° C. for 6 h in Easy Hyb buffer followed by high stringency washes, a blocking step (30 min), detection with alkaline phosphatase-conjugated anti-DIG Fab fragments (30 min), further washes, reaction with CDP-Star substrate (5 minutes) and exposure to X-ray film according to 3'-End labeling kit instructions (Roche). The density of signal in Southern and dot blots was quantitated using ImageJ software (available at rsb.info.nih.gov/ij).

TABLE 1

Primers and probes

| Description | Sequence | SEQ ID NO: |
|---|---|---|
| FVIII vector genome quantitation | | |
| FVIII A1-Forward Primer | GACGTGGTGCGCTTCGA | 5 |
| FVIII A1-Reverse Primer | GGGCGTAATCCCAGTCCTCT | 6 |
| FVIII A1 probe | AAGCGTGGCCAAGAAGCACCCC | 7 |
| Ampicillin$^R$ gene quantitation | | |
| Amp-Forward Primer | GTTGCCATTGCTACAGGCATC | 8 |
| Amp-Reverse Primer | ACTCGCCTTGATCGTTGGG | 9 |
| Amp-probe | FAM-ACGCTCGTCGTTTGGTATGGCTTCATTC-TAMRA | 10 |
| Puromycin$^R$ gene quantitation | | |
| Puromycin-Forward Primer | GGACCGCCACATCGAGC | 11 |
| Puromycin-Reverse Primer | CCCCGCTTCGACGCT | 12 |
| Puromycin-probe | FAM-TCACCGAGCTGCAAGAACTCTTCCTCAC-TAMRA | 13 |
| Rep gene quantitation | | |
| Rep-Forward Primer | GACCAGGCCTCATACATCTCCTT | 14 |
| Rep-Reverse Primer | GGCAGCCTTGATTTGGGA | 15 |
| Rep-probe | FAM-AATGCGGCCTCCAACTCGCG-TAMRA | 16 |
| E6 gene quantitation | | |
| E6-Forward Primer | CAACACGGCGACCCTACAA | 17 |
| E6-Reverse Primer | TCCAATACTGTCTTGCAATATACACAGG | 18 |
| E6-probe | FAM-TGCACGGAACTGAACACTTCACTGCAAG-TAMRA | 19 |
| Vector genome analysis | | |
| Oligo#4768 (+) | CCGTCGTGAATAGCCTGGACCCTC | 20 |
| Oligo#4924 (+) | ATCTGTGTGTTGGTTTTTTGTGTGCGGC | 21 |
| Oligo#3342 (−) | AATCCCAGTCCTCTTCCTCGGCGGCGATA | 22 |
| Oligo#4900 (−) | AGTATCGGAACACTCGCTCTACGAAATGT | 23 |

Evaluation of AAV/mTTR-hFVIII Vector Generated from Producer Cell Lines in Vivo rAAV vector were evaluated in male hemophilia A KO mice (C56BL/6, 129S-F8$^{tm1Kaz}$[neo gene in exon 16]) at 8-12 weeks age (Jackson Laboratories). Vectors (4, 10 and 30×10$^{10}$ DRP/mouse) were administered by intravenous route via tail vein. Blood was collected via retro-orbital sinus into sodium citrate tubes and plasma was stored frozen until analysis. Plasma samples were analyzed for FVIII activity levels using Coatest assay (Diapharma) according to manufacturer's protocol (modified for a 96-well format). Values were measured as % FVIII activity present in normal plasma and converted to ng/ml (100% FVIII=150 ng FVIII/ml). Some samples were also tested for partial thromboplastin time (PTT, IDEXX). FVIII protein levels were quantitated by standard ELISA (Enzyme Research Laboratories) using pooled normal human plasma (Innovative Research) as standard.

Liver samples were collected at the end of each study. Livers (50-400 mg) in 1 mL RLTplus with 10 µl β-mercaptoethanol and ¼ inch of zirconia 1 mm beads were homogenized with bead beater-16. A portion of the homogenate was placed into Trizol (for RNA) or DNA Stat-60 (for DNA). RNA was purified using the Trimega protocol followed by purification with a spin column (Promega Z3100) according to the manufacturer. The RNA was eluted with nuclease-free water and centrifuged for 1 min at 15,000×g. RNA was used to generate cDNA (Invitrogen). DNA was purified by DNA extraction Purelink columns (Invitrogen) according to manufacturer's instructions. Both cDNA and DNA were subsequently used to quantitate FVIII mRNA and vector genome copies, respectively, by qPCR using primers and probe specific to FVIII A2 region (Table 1).

Results

In order to generate a PCL platform for oversized rAAV vector production, novel cassettes were constructed for expression of FVIII. These cassettes were flanked by AAV ITRs and ranged from 5.1 to 5.4 kb vector genomes (FIG. 1A). Each cassette included a promoter derived from the mTTR promoter, and different mTTR variants were constructed to examine their effects on expression (see alignment and explanation of variants provided in FIG. 1B).

Figure 1C:
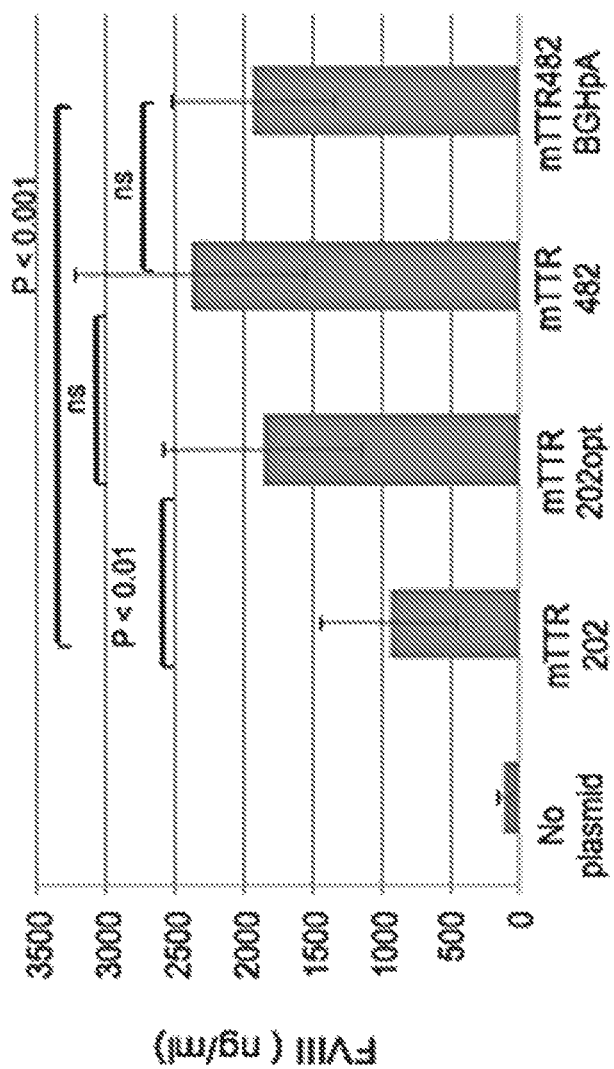
FIG. 1C FVIII levels from mTTR-FVIII expression cassettes in vivo. The plasmid vectors were injected intravenously by high volume injection into C56BL/6 mice, and Factor VIII levels in plasma were measured by ELISA assay.
Figure 1D:
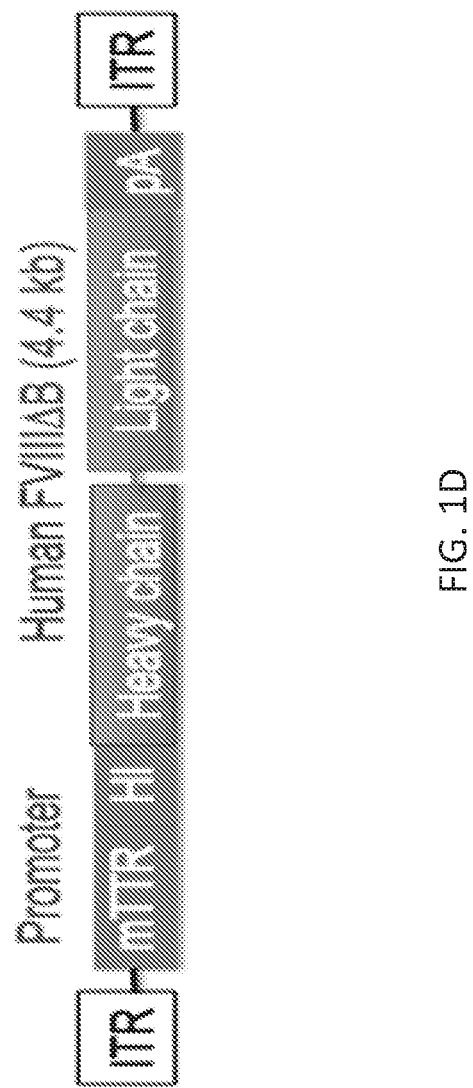
FIG. 1D shows the structure of the 5.1 kb FVIII expression cassette. This cassette includes rAAV inverted terminal repeats (ITRs), mouse transthyretin (mTTR) promoter, hybrid intron (HI), a B-domain deleted human FVIII cDNA, and a synthetic poly A sequence.
Figure 1E:
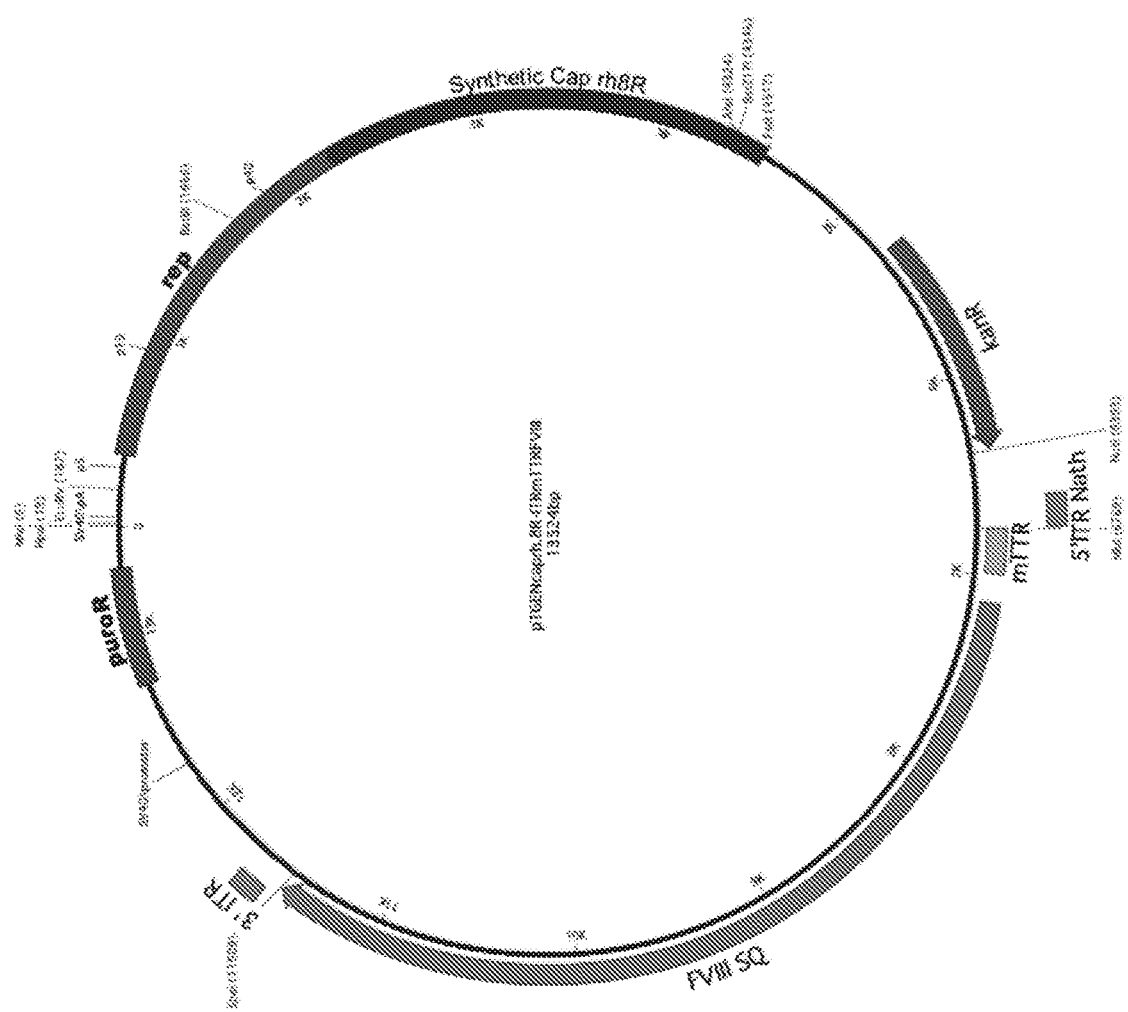
FIG. 1E shows the TriplePlay plasmid containing the FVIII vector genome, AAV rep and cap genes, as well as genes responsible for puromycin and kanamycin drug resistance.

All of these expression cassettes in the context of plasmids produced FVIII when tested in vivo in mice (FIG. 1C). Modifications in HNF3 and HNF4 binding sites shown in FIGS. 1A & 1B increased FVIII production over core mTTR promoter ("202") but additional modifications such as mTTR enhancer and BGH polyA did not (FIG. 1C). FIG. 1D shows a diagram of the FVIII expression cassette. FIG. 1E shows the design for the TriplePlay plasmid.

The expression cassettes with core mTTR (5.1 kb) and expression cassette with enhancer, mTTR and BGH poly A (5.4 kb) were used for subsequent testing of PCL production for oversized FVIII vectors after generating a TriplePlay plasmid for each. The FVIII ELISA results confirmed that transfected TriplePlay/FVIII plasmids produced FVIII in vitro when transfected into Huh7 cells. FVIII plasmids were also able to generate rAAV in small-scale packaging experiments.

In summary, mTTR promoter modifications were generated that increased expression from the core mTTR promoter in vivo. All TriplePlay plasmids expressed FVIII in vitro and were able to generate virus in small-scale packaging experiments.

To generate the producer cell lines with an oversized 5.1 kb mTTR-FVIII vector, MWs were analyzed for rAAVrh8R/FVIII production levels. Of these, high producers, medium producers, and low producers were identified. As such, it was shown that PCLs could be generated for the oversized rAAV/mTTR-FVIII vectors.

Example 2: Characterization of Genomic DNA for Producer Cell Line with mTTR-FVIII Vector To evaluate integrated copies of the TriplePlay plasmid and the integrity of FVIII expression cassette described in Example 1, MWs containing AAVrh8R/5.1 kb, AAVrh8R/5.4 kb, or AAV8/5.1 kb FVIII vector were chosen for analysis of genomic DNA.

Figure 2B:
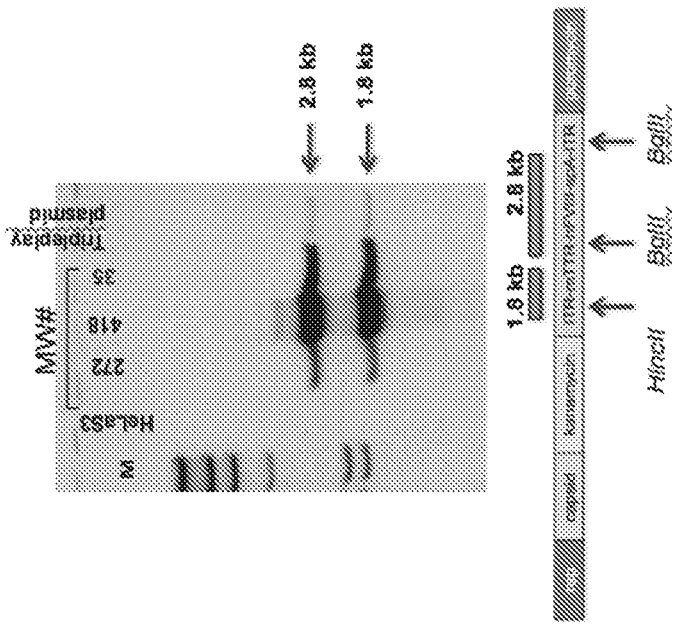
FIGS. 2A and 2B show Southern blot analyses of genomic DNA from selected masterwell clones (MWs).
Figure 2A:
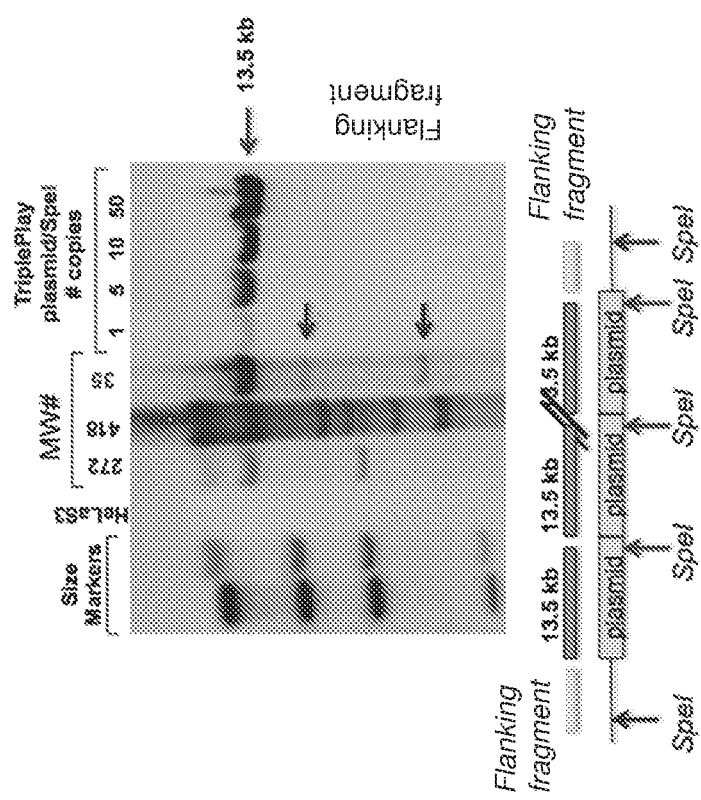

In the high producing MW (MW #35), the Southern analysis revealed approximately 50 copies of the vector in the cell line genome while the medium producing MW #272 had less than 10 copies of each by Southern (FIG. 2A).

High and medium producing MWs for production of AAVrh8R/5.1 kb, AAVrh8R/5.4 kb or AAV8/5.1 kb with mTTR-FVIII were also analyzed by qPCR (Table 2). Copy numbers for FVIII, rep and puroR genes were determined using specific primers/probes to each and copy numbers were normalized to E6 gene present in HeLaS3 cells (11 copies per HeLaS3 genome). In the high producing MW (MW #35), the qPCR analysis revealed approximately 59-67 copies of vector, rep and puromycin (Table 2) while the medium producing MW #272 had 15 to 18 copies of each by qPCR (Table 2). These values were slightly higher compared to the results obtained by Southern but had similar ranking order (FIG. 2A). For comparison, normal size vector (4.3 kb) expressing SEAP was packaged into AAV2 or AAV8 capsids and analyzed.

TABLE 2

Genomic analysis of selected MWs for copies of integrated TriplePlay plasmid.

| | | Copies/cell | | | |
| --- | --- | --- | --- | --- | --- |
| Cell line | Masterwell | FVIII (stdev) | REP (stdev) | PUROMYCIN (stdev) | Production level |
| AAVrh8R/FVIII 5.1kb | MW#35 | 67 (2) | 65 (0) | 59 (1) | H |
| AAVrh8R/FVIII 5.1kb | MW#272 | 15 | 16 | 18 | M |
| AAVrh8R/FVIII 5.1kb | MW#418 | 229 | 195 | 260 | H |
| AAVrh8R/FVIII 5.4kb | MW#61 | 235 (13) | 256 (1) | 196 (12) | M |
| AAVrh8R/FVIII 5.4kb | MW#163 | 253 (40) | 265 (1) | 237 (5) | H |
| AAV8/FVIII 5.1kb | MW#287 | 270 (38) | 294 (6) | 266 (13) | H |
| AAV8/FVIII 5.1kb | MW#342 | 101 (5) | 126 (2) | 108 (4) | H |

TABLE 2-continued

Genomic analysis of selected MWs for copies of integrated TriplePlay plasmid.

| Cell line | Masterwell | FVIII (stdev) | REP (stdev) | PUROMYCIN (stdev) | Production level |
|---|---|---|---|---|---|
| AAVrh8R/FVIIIopt 5.1KB | MW#14 | 1362 (48) | 1499 (22) | 1343 (42) | H |
| AAVrh8R/FVIIIopt 5.1KB | MW#27 | 77 (4) | 82 (3) | 73 (73) | M |
| AAV2/SEAP | control (MW#156 SEAP) | 0 | 73 (1) | 70 (2) | H |
|  | HeLaS3 | 0 | 0 | 0 |  |

Southern blot analysis of genomic DNA digested with a restriction enzyme (SpeI) predicted to cut only once in Tripleplay/FVIII plasmid showed a generation of a ~13 kb band that migrated similar to linearized Tripleplay/FVIII plasmid spiked into genomic DNA. Therefore, all clones contained the entire plasmid integrated into HeLaS3 genome.

As shown in FIG. 2A, all MWs also had varying sizes of low copy (one copy) bands representing the genomic DNA flanking the integration sites. While 272 (medium producer) and 35 (high producer) had a pattern indicative of a single integration site (only two flanking fragments observed), MW418 had multiple flanking fragments as well as larger (around 2×14=24 kb) fragment, potentially representing a tandem of forward and reverse orientations of the integrated plasmid. This fact, along with the multiple integration patterns, suggests that MW418 was a mixture of clones.

As shown in FIG. 2B, FVIII vector genome integrity was analyzed by digesting with enzymes (HincII, BglII) cleaving within the FVIII expression cassette. Correct size fragments were observed based on similar results obtained with digesting the original TriplePlay plasmid as compared to control. These results demonstrated that no rearrangements of the vector occurred upon integration. Similar analysis was done for producer cell lines with 5.4 kb vector as well as for 5.1 kb vector with AAV8 capsids and comparable results were obtained. In summary, no rearrangements or deletions in integrated 5.1 or 5.4 kb vector sequences were observed in the genomic DNA isolated from the producer cells lines indicating that generation of producer cell line containing oversized AAV vector genomes is feasible.

Figure 3A:
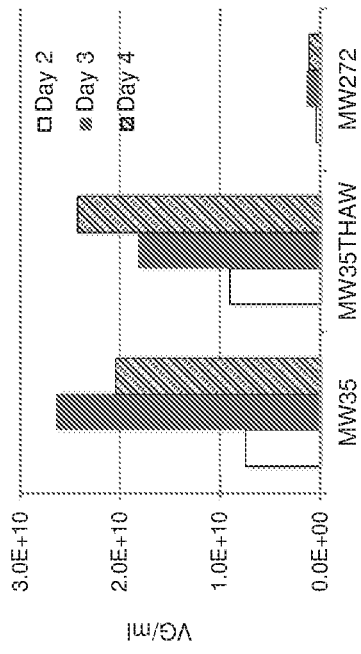
FIGS. 3A and 3B show analyses of AAVrh8R/5.1 kb mTTR-FVIII vector production yield and stability.

Example 3: Oversized Vector Production Using Producer Cell Lines and Vector Analysis Next, rAAV vector production using the MW35 cell line described above was examined. The high producing clone for AAVrh8R/5.1 kb FVIII vector (MW35) was tested for rAAV vector production in small-scale cultures. Peak rAAV production was seen on day 3 and 4 and high production levels were maintained during culture scale-up (FIG. 3A).

This is further demonstrated by the results shown in Table 3 below. Production by MW #35 was scaled up to compare vector production levels. Additionally, vector levels in cell pellet (cell) and culture media (CM) were quantitated. Normal size AAV2/SEAP vector is shown for comparison.

TABLE 3

AAVrh8R/5.1 kb vector production by MW#35.

| FVIII MW#35 | SP: VG/ml | Cell (%) | CM (%) |
|---|---|---|---|
| 20 ml (4 × $10^6$ cells) | 2.41 × $10^{10}$ | 39 | 61 |
| 250 ml (5 × $10^7$ cells) | 2.64 × $10^{10}$ | 45 | 55 |
| 1000 ml (2 × $10^8$ cells) | 3.17 × $10^{10}$ | 35 | 64 |
| MW156 (SEAP): 20 mls | 4.15 × $10^{10}$ | NT | NT |

Figure 3B:
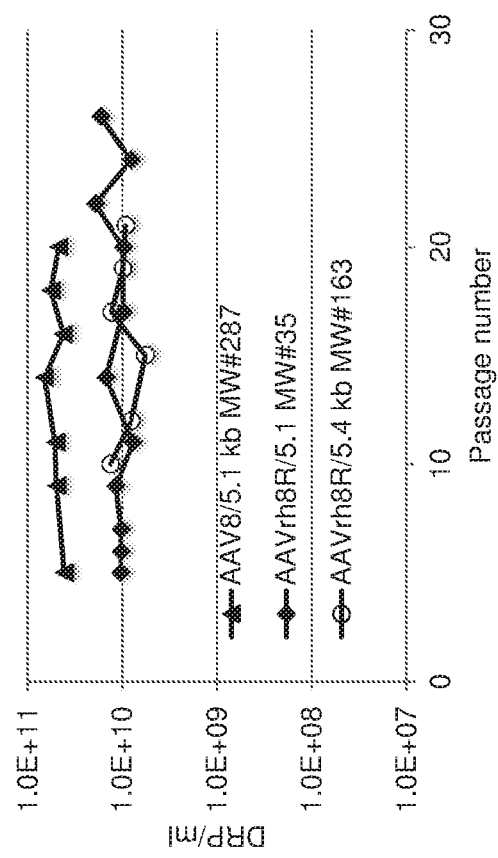

For the vector serotype used, the vector was equally detected in cell pellet and culture media. Both MWs 35 and 418 were stable over several passages. MW35 maintained high level of production (≥1×$10^{10}$ DRP/ml) from passage 5 through passage 20 (FIG. 3B). Similarly, MW418 (classified as medium producer) maintained stable medium level production (≥1×$10^9$ drp/ml) from passage 5 through passage 21. Stable vector production was also demonstrated for MW287 that generated 5.1 kb vector with different capsid serotype (AAV8) (FIG. 3B).

These data demonstrate that high and stable production can be obtained from oversized vectors, independent of capsid serotype, similar to what has previously been shown for normal size vectors (Martin, J. et al. (2013) *Molecular Therapy* 21:2205-2216). Robust vector production was also obtained with PCL with the 5.4 kb mTTR-FVIII vector as well as for PCL with the 5.1 kb vector with AAV8 capsids, yielding comparable results.

Figure 4A:
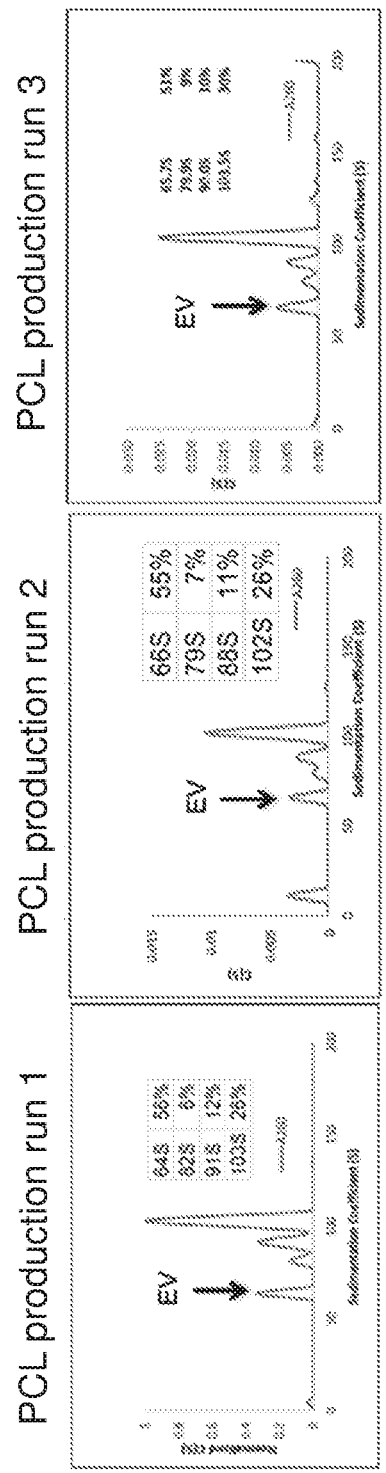
FIGS. 4A and 4B show an analysis of quality of oversized 5.1 kb rAAVrh8R/FVIII vectors. PCL and TXN produced 5.1 kb vector lots were compared by AUC analysis. AAVrh8R/5.1 kb FVIII was generated three times using MW #35 (FIG. 4A) and was compared to same vector produced by TXN method (FIG. 4B). Quality of the vectors was assessed by analytical ultracentrifugation analysis (AUC) that measures differences in the mass of the virus. Insert indicates % of capsids with differing sedimentation (S) values. The empty capsids typically have S value of 63 to 66 while capsids with wild-type size vector genome are typically at S of 100 to 103.
Figure 4B:
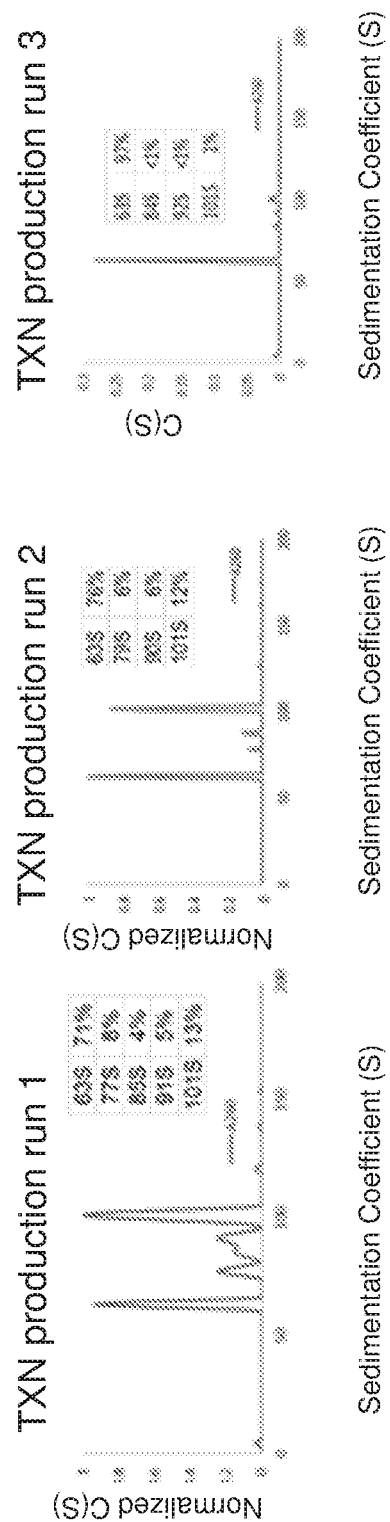

Next, vector production using high producing masterwells (MW #35 for AAVrh8R/5.1 kb FVIII, MW #287 for AAV8/5.1 kb FVIII and MW #163 for AAVrh8R/5.4 kb FVIII) were scaled-up to evaluate vector yield and quality (Table 4 and FIG. 4A). Vector production was compared to vector generated by the triple transfection method (Table 4 and FIG. 4B). Three PCL and two TXN lots were included in the comparison of AAVrh8R/5.1 kb FVIII vector. Data with AAVrh8R capsid with 5.1 kb genome is shown for example.

TABLE 4

Comparison of AAVrh8R/5.1 kb FVIII vector generated by PCL or triple transfection methods.

| Analysis | Producer cell line | Triple transfection |
|---|---|---|
| Cells/production | 2 × $10^9$ cells | 3 × $10^9$ cells |
| Total vector yield | 2 × $10^{14}$ DRPs | 6 × $10^{13}$ DRPs |
| Yield/cell | 1 × $10^5$ DRP/cell | 2 × $10^4$ DRP/cell |
| % VG containing virus | 44-50% | 24-30% |
| % virus with >4.7 kb VG | 59-61% | 43-50% |

PCL production runs with MW35 resulted in consistent product profile as assessed by AUC analysis (FIG. 4A). As summarized in Table 4 above, the percentage of vector genome containing capsids determined by this analysis was 44-50% for virus generated by PCL, while triple transfection material had lower levels (30%; only 1-5% for HLP19, large backbone vector plasmid). Furthermore, a higher portion of virus with larger genomes (≥4.7 kb) were present in the PCL generated material. The vector yields/cell were $1\times10^5$ DRP/cell by high producing PCL and $1\text{-}3\times10^4$ DRP/cell by TXN (with HLP19 and large vector backbones lower, $1\times10^3$ DRP/cell)

TABLE 5

Comparison of AAVrh8R/5.4 kb FVIII vector generated by PCL or triple transfection methods.

| Analysis | Producer cell line | Triple transfection |
| --- | --- | --- |
| Cells/production | $2 \times 10^9$ cells | $2 \times 10^9$ cells |
| Total vector yield (crude) | $2 \times 10^{13}$ DRPs | $2 \times 10^{14}$ DRPs |
| Yield/cell | $2 \times 10^4$ DRP/cell | $7 \times 10^4$ DRP/cell |
| % VG containing virus | 24% | 23% |
| % virus with >4.7 kb VGs | 68% | 39% |

Similar analysis for a 5.4 kb vector using MW163 showed slightly lower DRP/cell levels by PCL compared to triple transfection (Table 5 above). While total percentage of VG containing capsids was comparable, the PCL generated virus had higher level of virus with larger genomes (FIG. 5B).

Figure 5A:
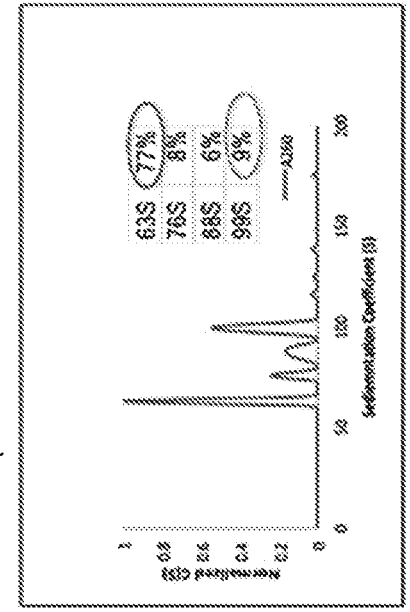
FIGS. 5A and 5B show analysis of quality of oversized 5.4 kb rAAVrh8R/FVIII vectors. PCL (FIG. 5A) and TXN (FIG. 5B) produced 5.4 kb vector lots were compared by AUC analysis. Insert indicates % of capsids with differing sedimentation (S) values. Percentages of empty capsids (64S/63S) and particles with larger genomes (101S/99S) are circled.
Figure 5B:
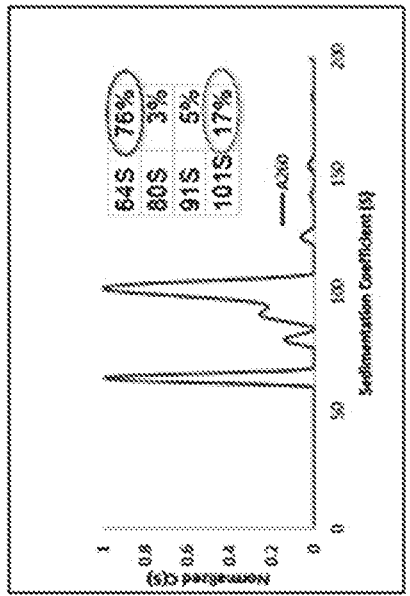

When PCL material and triple transfection material were characterized by AUC analysis, the proportion of larger genomes was 2-fold higher in PCL material (FIG. 5A) compared to triple transfection material (FIG. 5B).

TABLE 6

Analysis of aberrant packaging in vector produced by PCL and triple transfection.

| | Vector titer (DRP/ml) | | |
| --- | --- | --- | --- |
| Vector by PCL | FVIII | Puromucin | % Puromycin |
| AAVrh8R/5.1-FVIII | 1.2E+12 | 5.40E+09 | 0.44 |
| AAVrh8R/5.4-FVIII | 7.6E+12 | 1.54E+10 | 0.20 |
| AAV8/5.1-FVIII | 5.1E+12 | 1.21E+10 | 0.24 |
| Vector by TXN | FVIII | Ampicillin | % Ampicillin |
| AAVrh8R/5.1-FVIII | 2.3E+13 | 4.76E+11 | 2.10 |
| AAVrh8R/5.4-FVIII | 1.6E+13 | 5.38E+11 | 3.40 |
| AAVrh8R/FVIII 4.6kb | 1.2E+13 | 2.47E+11 | 2.00 |

The level of aberrant, unwanted DNA packaging as measured by the presence of plasmid-derived antibiotic resistance gene (puromycin for PCL, ampicillin for TXN) in the packaged virus was low in the virus generated by PCL (<1%) (Table 6). In contrast, the TXN generated virus had approximately 10-fold higher levels of aberrant packaging.

In summary, the data showed that selected producer cell lines were able to generate high level of oversized vector (>100,000 DRP/cell). Furthermore, these cell lines maintained the vector production ability over several passages (>20) that would be required for large scale-up for manufacturing. Comparison of PCL produced vector to that generated by standard triple transfection method showed that the PCL material contained more vector genome containing virus and a higher proportion of wild-type size or larger vector genomes as well as contained less unwanted, non-vector related DNA.

Figure 6B:
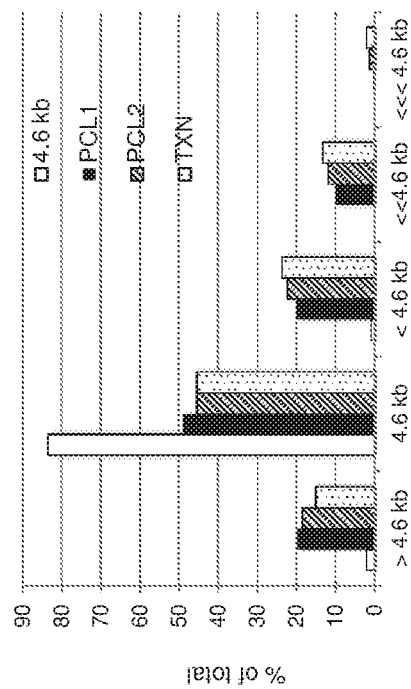
FIGS. 6A and 6B show characterization of packaged vector genomes in PCL or TXN generated rAAVrh8R/5.1 kb vectors by Southern blot. Vector genomes were isolated from purified virions and analyzed for sizes by alkaline gel electrophoreses followed by Southern blot using probes specific to the vector.
Figure 6A:
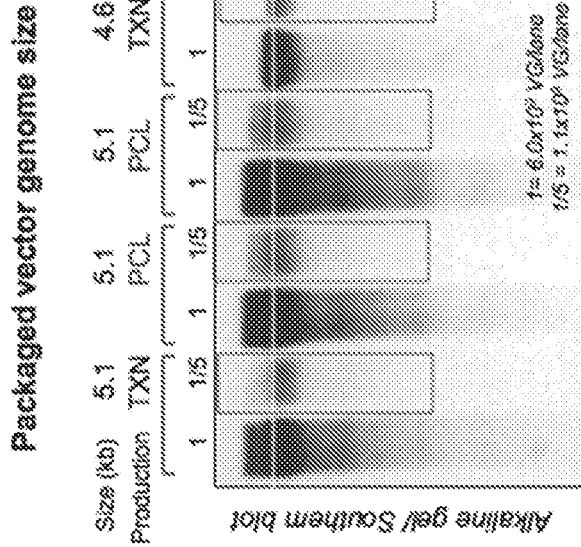

Example 4: Characterization of Packaged Vector Genomes in PCL Produced Oversized Vectors Next, the encapsidated vector genomes in oversized rAAV vectors produced by the PCL platform were analyzed. Vector genomes were isolated from purified virions and analyzed for single-stranded genome sizes by alkaline gel electrophoreses followed by Southern blot analysis using probes specific to the vector (FIG. 6A). Southern blot probed by 4.0 kb fragment of FVIII expression cassette showed that the majority of VGs sizes were approximately at 4.6 kb or larger in vectors generated by either methods (FIG. 6B). The density of signal in Southern blots was quantitated using ImageJ software (http://rsb.info.nih.gov/ij).

VGs were also analyzed using strand specific oligonucleotide probes to quantitate proportion of deleted 5' terminal ends. Since packaging of AAV genomes is known to occur starting from the 3' ends (King, J. A. et al. (2001) *EMBO J.* 20:3282-3291), oversized vectors may lack sequence in 5' ends of minus and plus strands when genome size exceeds 4.7 kb. Vector lots used in FIGS. 4A & 4B were analyzed by applying 2-fold serial dilutions of each vector onto membrane (starting at $2.4\times10^9$; total of eight decreasing vector concentrations plus no genomes applied as negative control). Each blot was hybridized with 3' end labeled oligonucleotide probes specific to 3' or 5' terminal ends of vector genomes (plus or minus polarity). The signal intensity was quantitated and normalized to 4.6 kb vector (completely packaged). Three concentrations were used to generate standard error.

Figure 7B:
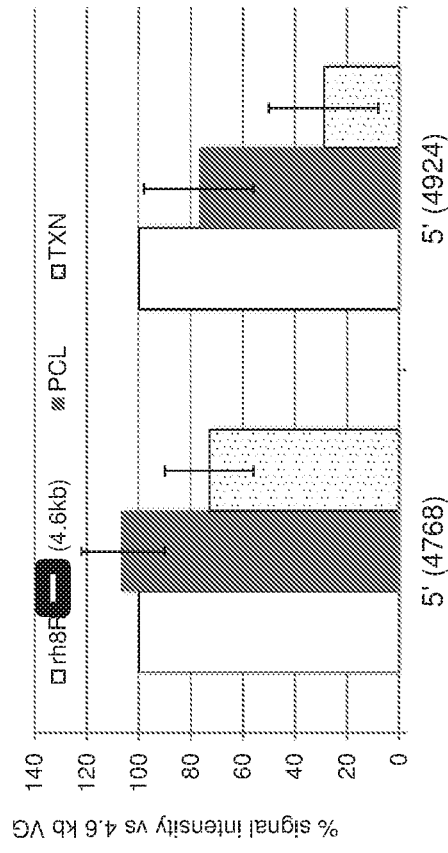
FIGS. 7A, 7B and 7C show characterization for 5' ends of packaged vector genomes in PCL or TXN generated rAAVrh8R/5.1 kb vectors by DNA dot blot analysis. Vector lots used in FIG. 5 were analyzed by applying 2-fold serial dilutions of each vector onto membrane (starting at $2.4 \times 10^9$; total of eight decreasing vector concentrations plus no genomes applied as negative control). Each blot was hybridized with 3' end-labeled oligonucleotide probe specific to middle or the 5' terminal ends of the vector genomes (plus or minus polarity). The signal intensity was quantitated and normalized to 4.6 kb vector (completely packaged). Three concentrations were used to generate standard error.
Figure 7C:
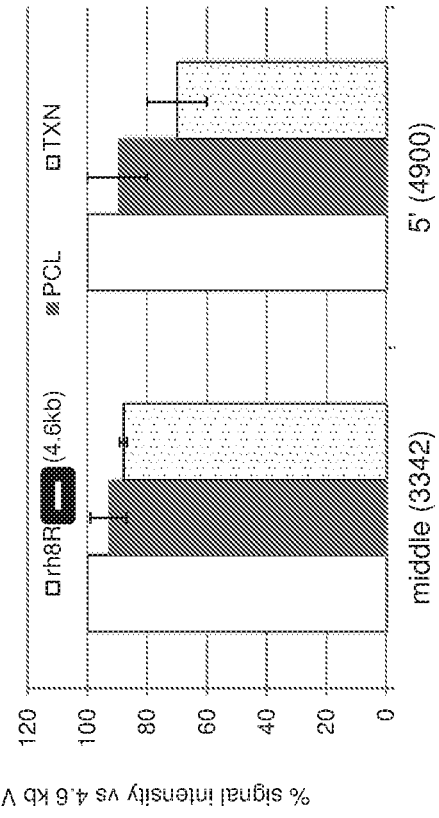
Figure 7A:
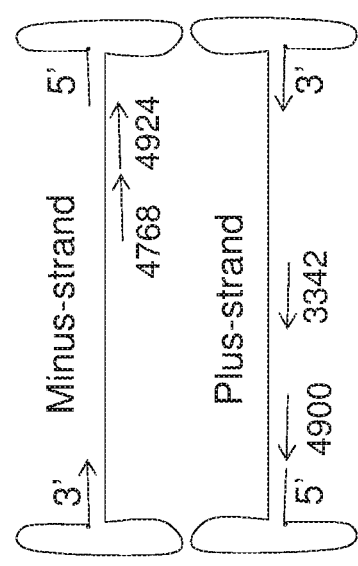

The data showed that compared to completely packaged 4.6 kb vector (with comparable sequence to 5.1 kb vector except region encoding for the C1 domain of FVIII), the 5.1 kb vectors had a lower signal intensity when oligonucleotides complementary to the regions beyond 4.7 kb were used for both polarities of single-stranded genomes (FIGS. 7A & 7B & 7C). This difference was higher in triple transfected material compared PCL vector with most of the 5' probes used.

Figure 8B:
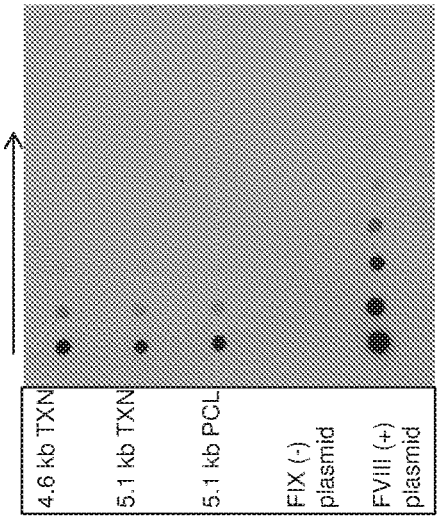
Figure 8B:
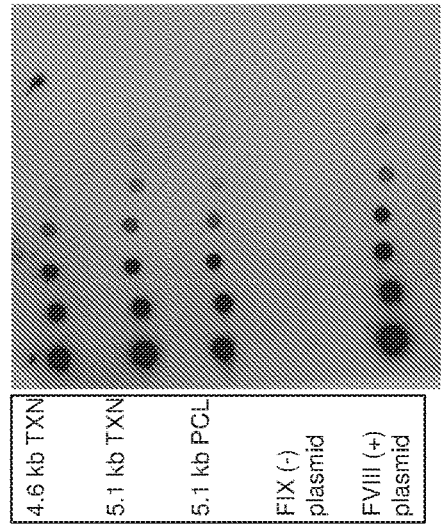
Figure 8A:
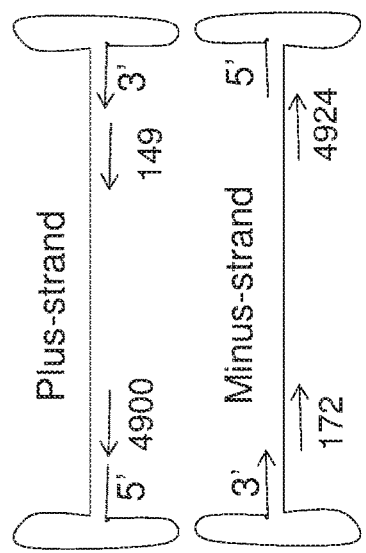

The difference in the 5' ends in PCL and triple transfection generated vectors was also observed when Southern blots were probed with oligonucleotide probes complementary to + or − strands. The distance of each oligonucleotide probe from the respective 3' termini is shown (FIG. 8A). Equal detection of PCL and triple transfection (TXN) generated virus was first compared by DNA dot blot analysis with strand-specific oligonucleotide probes and showed comparable amounts of each virus for each strand (4.6 kb virus was used as control for completely packaged virus; FIX and FVIII containing plasmids were used as negative and positive controls for detection specificity) (FIG. 8B). When Southern blots were probed with oligonucleotide probes to the 3' termini, both the PCL and TXN generated viruses demonstrated presence of + and − strands (FIG. 8C, left panels). Higher levels of vector genomes larger than 4.6 kb were detected in PCL virus similar to observations shown in FIG. 6A. When the Southern blots were probed with oligonucleotides specific to the 5' termini, the PCL vector showed presence of packaged genomes larger than 4.6 kb while the triple transfection generated virus showed a clear lack of signal for these larger genomes (probe used detected a region at 4.9 kb from the 3' end) (FIG. 8C). The higher portion of genomes larger than 4.7 kb were also confirmed by quantitation of signal intensity for various size packaged genomes in the Southern blots (using probe to 3' termini)

(FIG. 8D). The quantitation also showed less fragmented/smaller genomes (<4.7 kb) in PCL vector compared to TXN vector.

Figure 9B:
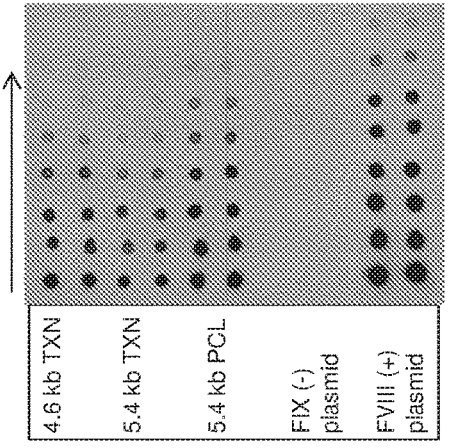
FIGS. 9A, 9B and 9C show characterization of 5' and 3' ends of packaged vector genomes in PCL or TXN generated rAAVrh8R/5.4 kb vectors.
Figure 9B:
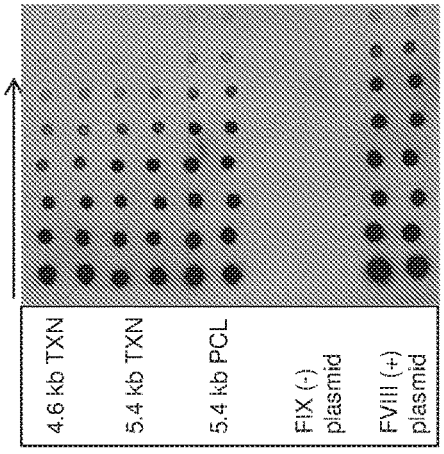
Figure 9A:
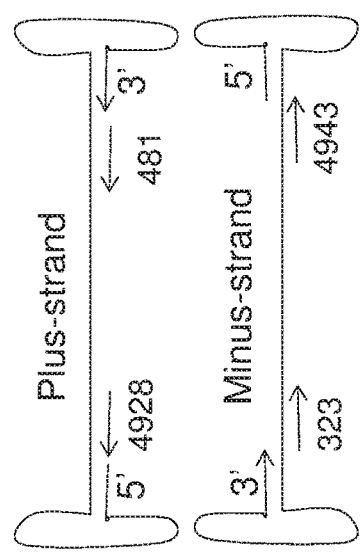
Figure 9C:
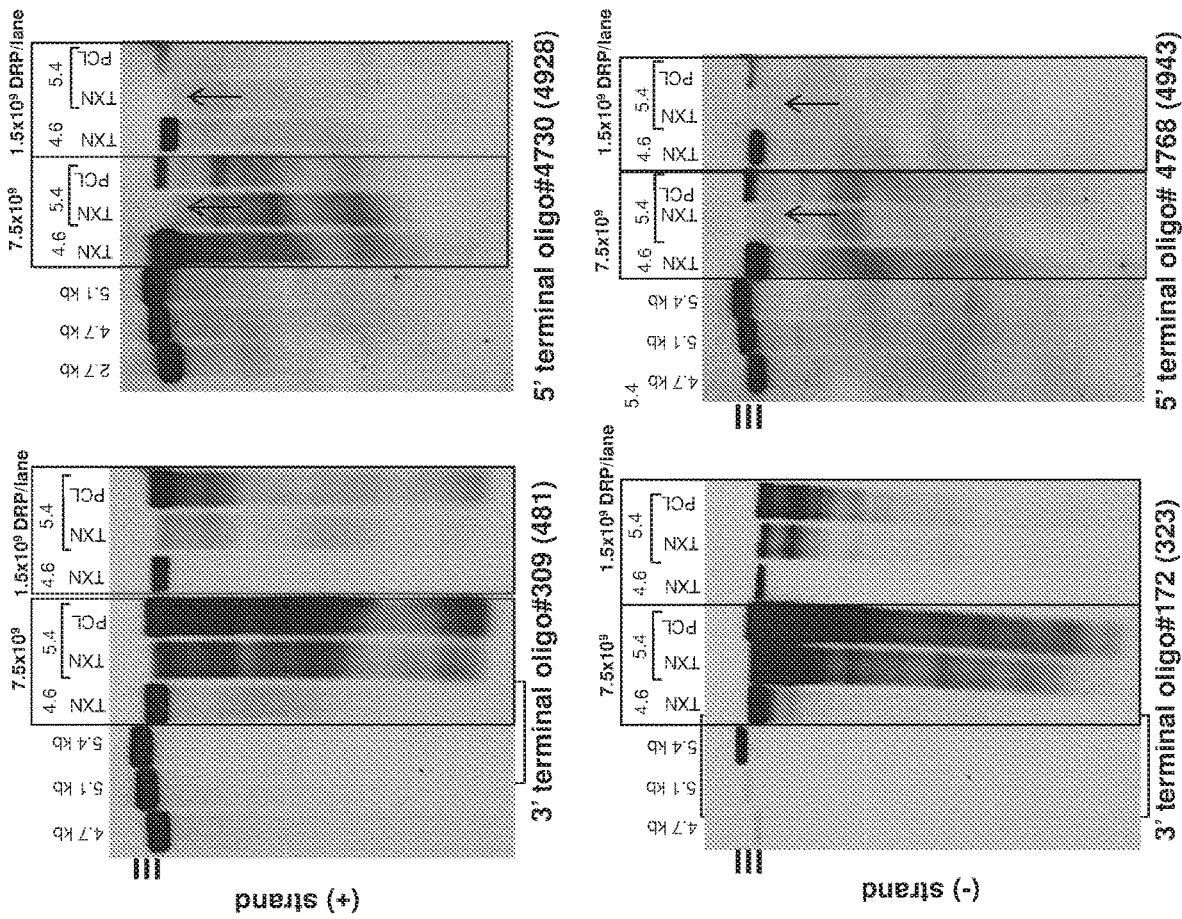

We next evaluated vector genome packaging of 5.4 kb FVIII vector generated by PCL and TXN by similar methods. The location of complementary sequence for each oligonucleotide probe in the 5.4 kb genome from their respective 3' termini is shown (FIG. 9A). Similar to results for the 5.1 kb vectors, the + and − strands of the 5.4 kb vectors were detected in comparable levels with oligonucleotide probes to the 3' termini of the genomes (FIG. 9B). However, the probes specific to areas located further than 4.7 kb from the 3' ends failed to detect genomes in vectors generated by TXN method (FIG. 9C). In contrast, vectors generated by PCL method showed presence of genomes larger than 4.7 kb (though not as large as 5.4 kb).

In summary, the data demonstrated higher level of larger vector genome packaging in vectors generated by PCL method compared to that of TXN method.

Example 5: Efficacy of Oversized rAAV/mTTR-FVIII Vectors In Vivo

Figure 10A:
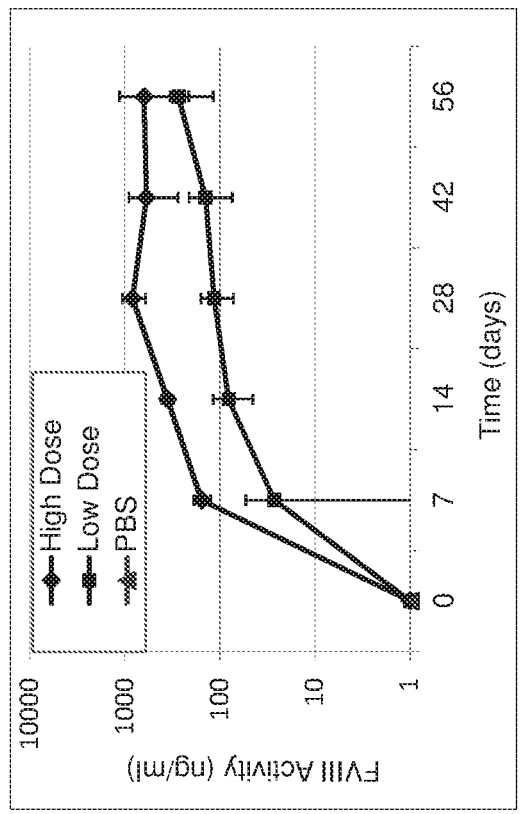
FIGS. 10A and 10B show efficacy of PCL produced rAAVrh8R/5.1 kb vector in vivo in hemophilia A KO mice. The vector was administered to mice by tail vein at $3 \times 10^{11}$ and $4 \times 10^{10}$ DRP/mouse and plasma FVIII levels were analyzed up to day 56.
Figure 10B:
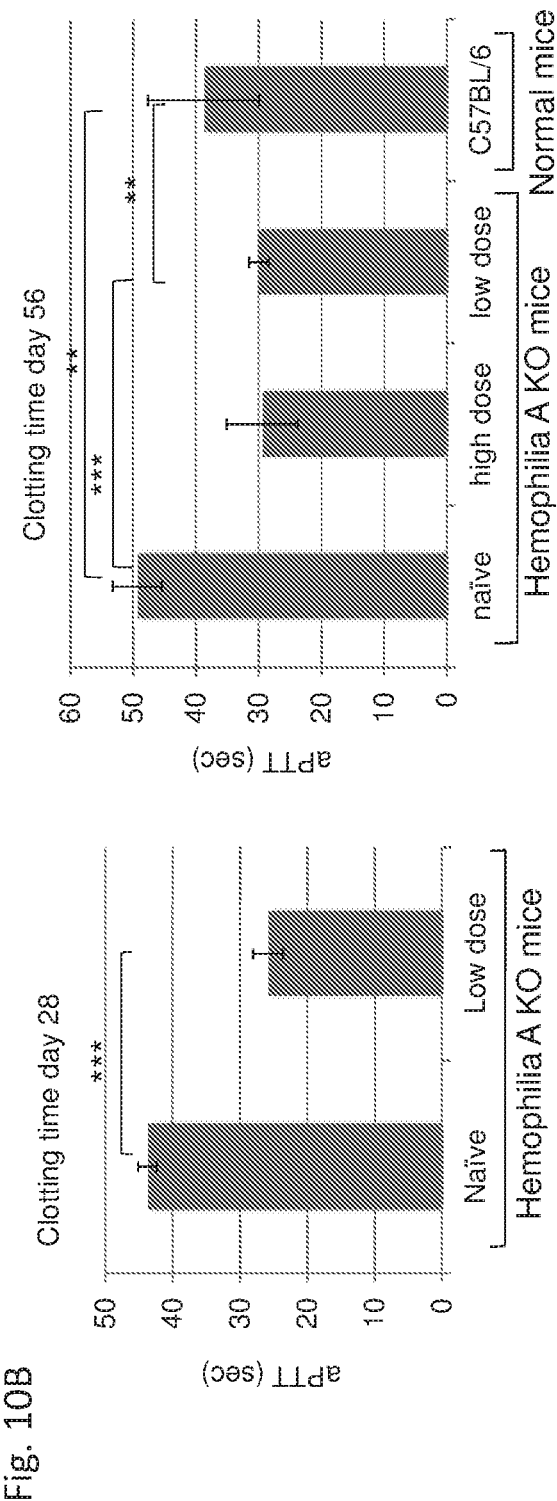

Next, oversized rAAV vectors produced by the PCL platform were examined for efficacy in vivo. Vector was administered to mice by tail vein at $3\times10^{11}$ and $4\times10^{10}$ DRP/mouse and analyzed till day 56. The PCL produced AAVrh8R/5.1 kb mTTR-FVIII vector generated active FVIII protein detectable in plasma of treated hemophilia A KO mice in a dose-responsive manner (FIG. 10A). In addition to Coatest activity assay, the FVIII activity was also evaluated for functionality by clotting time using an activated partial thromboplastin time (aPTT) assay. This assay showed comparable clotting times for the low and high doses tested, thus indicating that the clinically relevant low dose was sufficient to normalize the clotting time in hemophilia A KO mice (FIG. 10B).

Figure 11A:
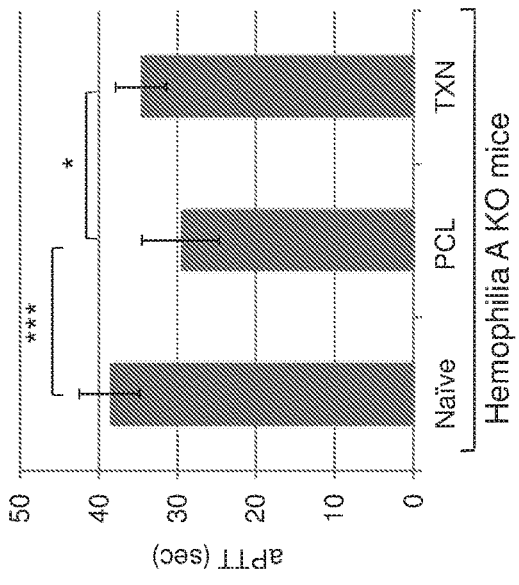
FIGS. 11A, 11B and 11C show comparison of PCL and TXN produced 5.1 kb AAVrh8R/FVIII vectors in vivo using hemophilia A KO mice. Vectors were administered to mice by tail vein at $4 \times 10^{10}$ DRP/mouse.
Figure 11C:
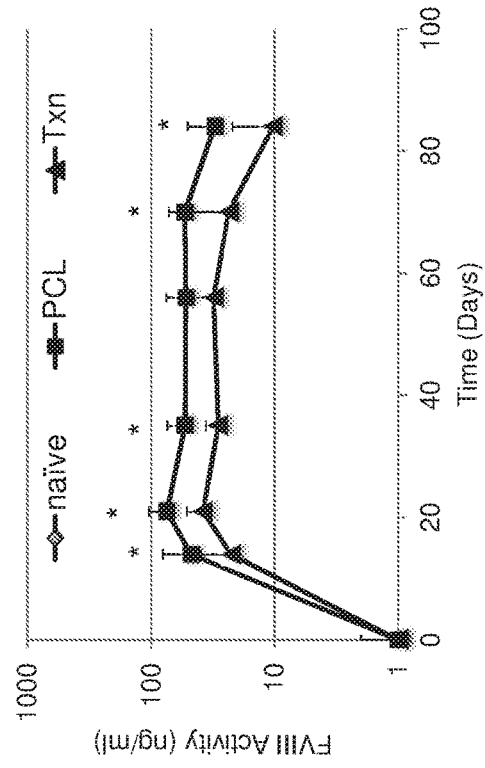
Figure 11B:
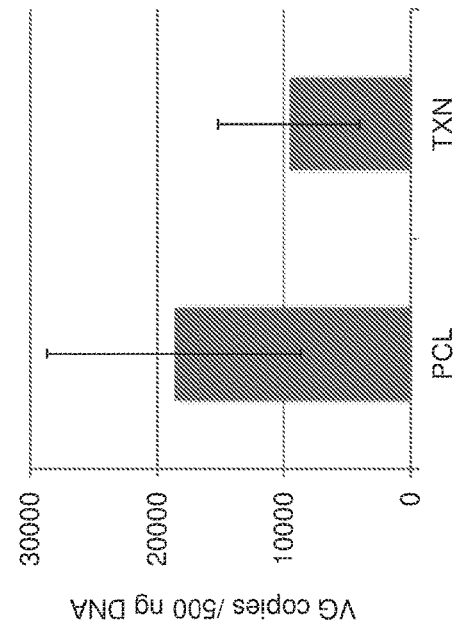
Figure 11D:
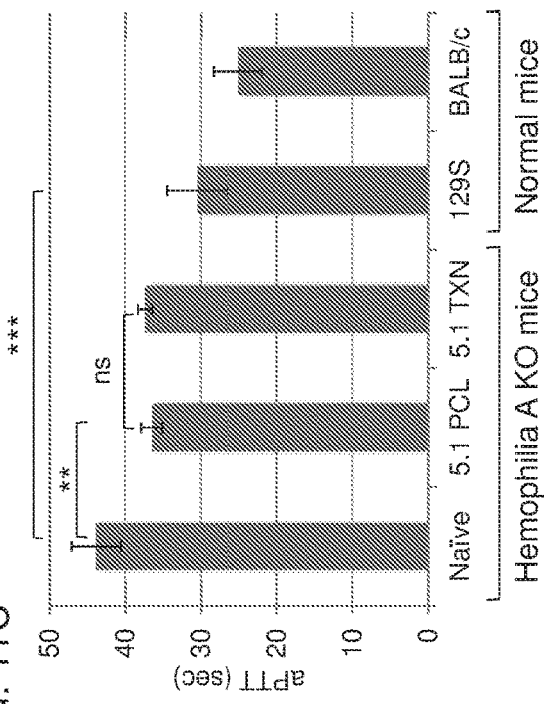
(FIG. 11D) Vector genome (VG) copies in the liver on day 84. VG copies were quantitated by qPCR and are shown as copies/500 ng of total liver DNA. Each treatment group contained n=8 mice/group. Statistical significance is indicated as follows: *, $p<0.05$; , $p<0.01$, *, p<0.001 by Student t-test. The method of virus production is indicated (PCL or TXN) in each panel.

The PCL generated vector was then compared to triple transfection-produced vector using a clinically relevant vector dose ($2\times10^{12}$ DRP/kg, $4\times10^{10}$ DRP/mouse). Vectors were administered to hemophilia A KO mice by tail vein. The PCL generated virus produced more active FVIII protein than TXN produced virus as determined by Coatest activity assay (FIG. 11A). This also correlated with a significantly shorter clotting time on day 21 by aPTT assay by the PCL generated vector (FIG. 11B). Little difference was observed between PCL and TXN material on day 56 suggesting that the PCL material resulted in faster expression kinetics (FIG. 11C). Quantitation of liver vector genome copies showed more persistent vector genomes in the animals treated by the PCL generated vector than that observed with the TXN material (FIG. 11D).

Figure 12A:
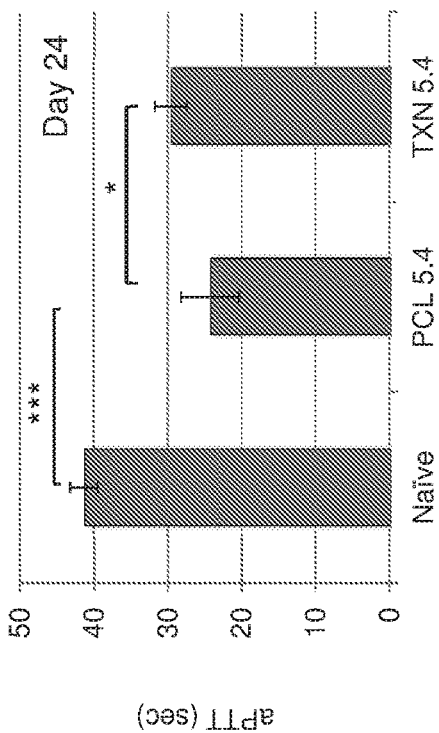
FIGS. 12A, 12B and 12C show comparison of PCL and TXN produced 5.4 kb AAVrh8R/FVIII vectors in vivo using hemophilia A KO mice. Vectors were administered to mice by tail vein at $4 \times 10^{10}$ DRP/mouse and plasma samples collected on days 24 and 43 after vector administration.
Figure 12B:
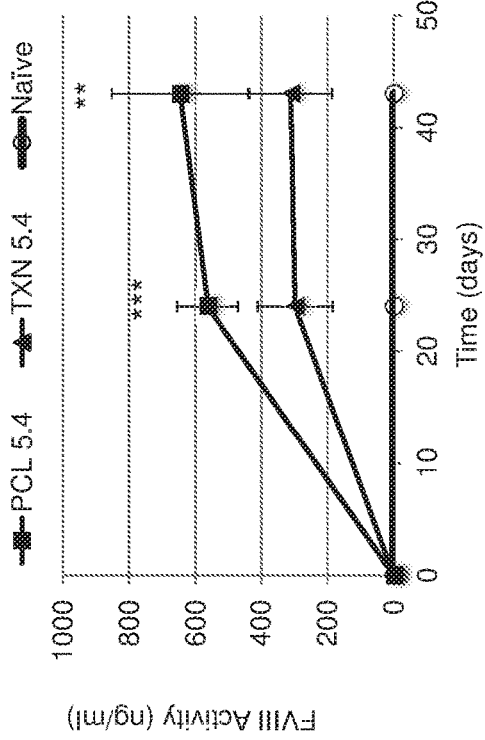
Figure 12C:
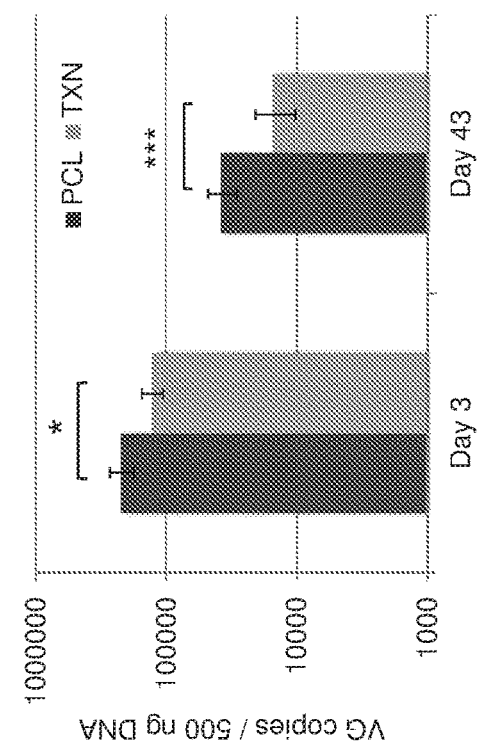

PCL and TXN generated larger, 5.4 kb FVIII vector was also tested hemophilia A knock-out mice. Similar to 5.1 kb vector, the 5.4 kb vector generated by PCL showed higher FVIII activity by Coatest assay and shorter clotting time on day 24 (FIGS. 12A, B). To analyze the kinetics of the vector genome levels in the liver, vector genome copies were quantitated both 3 and 43 days after vector administration. The data demonstrated that on both days there were approximately 2-fold more vector genomes in the animals treated by the PCL generated vector than that with the TXN material (FIG. 12C).

In summary, the oversized rAAV/mTTR-FVIII vector generated by the PCL method resulted in 2-fold higher FVIII activity and shorter clotting times than that of TXN method when tested in vivo in the hemophilia A KO disease model. These results correlated with the 2-fold higher levels of persistent vector genomes present in the liver of the treated animals. Hence, these results demonstrate that the differences observed in the quality of the packaged genomes between the two vector production methods for oversized rAAV vectors translate to a higher in vivo potency by the PCL generated vector and is based on the increased efficiency of generation of transcriptionally active vector genomes in the target organ.

Example 6: Generation of Producer Cell Lines with Oversized 5.1, 5.9, and 6.7 kb SEAP Vectors Methods:

Oversized AAV2-SEAP vector genomes were generated with stepwise increases in vector size (see FIG. 13A) ranging from 5.1 kb to 5.9 and 6.7 kb. AAT stuffer DNA fragments of three lengths (0.8, 1.6 and 2.4 kb) were amplified via PCR using as template the AAVsp70 plasmid and each stuffer fragment was cloned into the TriplePlay plasmids with AAV2 cap and rep genes and each of the SEAP vector genomes to generated series of pAF-SEAP plasmids.

For generation of cell lines for oversized SEAP vectors, the corresponding plasmids containing the vector genome and the AAV2 rep and cap genes were compared side-by-side for the ability to generate high producing cell lines in a 24-well high-throughput analytical transfection. Duplicate T75 flasks of HeLaS3 cells were transfected with each of the constructs per standard protocol. One day post-transfection, eight×24-well plates per transfection were seeded with 75,000 cells/well and drug selection initiated. The samples were cultured and assessed for colony size and confluence in preparation for the relative productivity screening.

Results:

The 5.1, 5.9 and 6.7 kb oversized vector plasmids (FIG. 13A) were first confirmed for packaging via transient transfection into HeLaS3 cells (+wtAd5). The result showed that each plasmid facilitated vector packaging (data not shown).

Approximately ~100-170 masterwells were screened for each construct in the relative production screen. The percent positive masterwells (those producing greater than $1\times10^7$ DRP/ml) in the relative production screen were high across the board (>80%) with only the 6.7 kb construct showing a reduced amount (65.7%). Furthermore, although only the 5.1 kb construct yielded masterwells producing in the high ($>1\times10^{10}$ DRP/ml) range (three total), masterwells producing in the medium-high range ($>1\times10^9$ DRP/ml) were identified in all cases. The percentage medium-high follows an expected pattern, with 5.1 kb at 20%, 5.9 kb at 15.4% and 6.7 kb at 10.7%.

All of the higher-producing masterwells were subsequently subjected to an analysis of specific productivity. The results of two specific productivity screens are shown in FIG. 13B (gray and white bars) and are compared to the relative productivity value (black bar) for each masterwell. The results showed that in many cases the vector yields remained stable in the specific productivity screens.

In summary, the data demonstrated that producer cell lines could be generated for vectors at least 6.7 kb in size.

SEQUENCES

All polypeptide sequences are presented N-terminal to C-terminal unless otherwise noted.

All nucleic sequences are presented 5' to 3' unless otherwise noted.

mTTR202-HI-hFVIIIco-spA (5097 bp)

(SEQ ID NO: 1)
GAGCTCTTGGCCACTCCCTCTCTGCGCGCTCGCTCGCTCACTGAGGCCGG
GCGACCAAAGGTCGCCCGACGCCCGGGCTTTGCCCGGGCGGCCTCAGTGA
GCGAGCGAGCGCGCAGAGAGGGAGTGGCCAACTCCATCACTAGGGGTTCC
TACGCGTGTCTGTCTGCACATTTCGTAGAGCGAGTGTTCCGATACTCTAA
TCTCCCTAGGCAAGGTTCATATTTGTGTAGGTTACTTATTCTCCTTTTGT
TGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGA
GAAGCCGTCACACAGATCCACAAGCTCCTGCTAGCAGGTAAGTGCCGTGT
GTGGTTCCCGCGGGCCTGGCCTCTTTACGGGTTATGGCCCTTGCGTGCCT
TGAATTACTGACACTGACATCCACTTTTTCTTTTTCTCCACAGGTATCGA
TTCTCTAGAGCCACCATGCAGATCGAGCTGTCTACCTGCTTCTTCCTGTG
CCTGCTGCGGTTCTGCTTCAGCGCCACCAGACGGTACTATCTGGGCGCCG
TGGAACTGAGCTGGGACTACATGCAGAGCGACCTGGGCGAGCTGCCCGTG
GATGCCAGATTCCCTCCAAGAGTGCCCAAGAGCTTCCCCTTCAACACCTC
CGTGGTGTACAAGAAAACCCTGTTCGTGGAATTCACCGACCACCTGTTCA
ATATCGCCAAGCCCAGACCCCCCTGGATGGGCCTGCTGGGACCTACAATT
CAGGCCGAGGTGTACGACACCGTCGTGATCACCCTGAAGAACATGGCCAG
CCACCCCGTGTCTCTGCATGCCGTGGGAGTGTCCTACTGGAAGGCCTCTG
AGGGCGCCGAGTACGACGATCAGACCAGCCAGCGCGAGAAAGAGGACGAC
AAGGTGTTCCCTGGCGGCAGCCACACCTACGTGTGGCAGGTGCTGAAAGA
AAACGGCCCCATGGCCTCCGACCCTCTGTGCCTGACATACAGCTACCTGA
GCCACGTGGACCTCGTGAAGGACCTGAACAGCGGCCTGATCGGAGCCCTG
CTCGTGTGTAGAGAGGGCAGCCTGGCCAAAGAGAAAACCCAGACCCTGCA
CAAGTTCATCCTGCTGTTCGCCGTGTTCGACGAGGGCAAGAGCTGGCACA
GCGAGACAAAGAACAGCCTGATGCAGGACCGGGACGCCGCCTCTGCTAGA
GCCTGGCCCAAAATGCACACCGTGAACGGCTACGTGAACAGAAGCCTGCC
CGGACTGATCGGCTGCCACCGGAAGTCTGTGTACTGGCACGTGATCGGCA
TGGGCACCACCCCTGAGGTGCACAGCATCTTTCTGGAAGGACACACCTTT
CTCGTGCGGAACCACCGGCAGGCCAGCCTGGAAATCAGCCCTATCACCTT
CCTGACCGCCCAGACACTGCTGATGGACCTGGGCCAGTTTCTGCTGTTCT
GCCACATCAGCTCCCACCAGCACGACGGCATGGAAGCCTACGTGAAGGTG
GACAGCTGCCCCGAGGAACCCCAGCTGCGGATGAAGAACAACGAGGAAGC
CGAGGACTACGACGACGACCTGACCGACAGCGAGATGGACGTGGTGCGCT
TCGACGACGATAACAGCCCCAGCTTCATCCAGATCAGAAGCGTGGCCAAG
AAGCACCCCAAGACCTGGGTGCACTATATCGCCGCCGAGGAAGAGGACTG
GGATTACGCCCCTCTGGTGCTGGCCCCCGACGACAGAAGCTACAAGAGCC
AGTACCTGAACAATGGCCCCCAGCGGATCGGCCGGAAGTATAAGAAAGTG
CGGTTCATGGCCTACACCGACGAGACATTCAAGACCAGAGAGGCCATCCA
GCACGAGAGCGGCATCCTGGGCCCTCTGCTGTATGGCGAAGTGGGCGACA
CCCTGCTGATCATCTTCAAGAACCAGGCCAGCAGACCCTACAACATCTAC
CCTCACGGCATCACCGACGTGCGGCCCCTGTACTCCAGAAGGCTGCCCAA
GGGCGTGAAACACCTGAAGGACTTCCCCATCCTGCCCGGCGAGATCTTCA
AGTACAAGTGGACCGTGACCGTGGAAGATGGCCCCACCAAGAGCGACCCC
AGATGCCTGACACGGTACTACAGCAGCTTCGTGAACATGGAACGGGACCT
GGCCTCCGGCCTGATTGGCCCACTGCTGATCTGCTACAAAGAAAGCGTGG
ACCAGCGGGGCAACCAGATCATGAGCGACAAGCGGAACGTGATCCTGTTT
AGCGTGTTCGATGAGAACCGGTCCTGGTATCTGACCGAGAATATCCAGCG
GTTCCTGCCCAACCCTGCCGGCGTGCAGCTGGAAGATCCTGAGTTCCAGG
CCTCCAACATCATGCACTCCATCAATGGCTATGTGTTCGACAGCCTGCAG
CTGAGCGTGTGCCTGCACGAGGTGGCCTACTGGTACATCCTGAGCATCGG
GGCCCAGACCGACTTCCTGTCCGTGTTCTTCTCCGGCTACACCTTCAAGC
ACAAGATGGTGTACGAGGATACCCTGACCCTGTTCCCCTTTAGCGGCGAA
ACCGTGTTCATGAGCATGGAAAACCCCGGCCTGTGGATCCTGGGCTGCCA
CAACAGCGACTTCCGGAACAGAGGCATGACCGCCCTGCTGAAGGTGTCCA
GCTGCGACAAGAACACCGGCGACTACTACGAGGACAGCTATGAGGACATC
AGCGCCTACCTGCTGAGCAAGAACAATGCCATCGAGCCCAGAAGCTTCAG
CCAGAACCCCCCCGTGCTGAAGCGGCACCAGAGAGAGATCACCCGGACCA
CCCTGCAGTCCGACCAGGAAGAGATCGATTACGACGACACCATCAGCGTG
GAAATGAAGAAAGAAGATTTCGACATCTACGACGAGGACGAGAACCAGAG
CCCCCGGTCCTTTCAGAAAAAGACCCGGCACTACTTCATTGCCGCTGTGG
AACGGCTGTGGGACTACGGCATGAGCAGCAGCCCTCACGTGCTGAGAAAC
AGGGCCCAGAGCGGCAGCGTGCCCCAGTTCAAGAAAGTGGTGTTCCAGGA
ATTCACAGACGGCAGCTTCACCCAGCCTCTGTACCGCGGCGAGCTGAATG
AGCACCTGGGACTGCTGGGCCCCTATATCAGAGCCGAAGTGGAAGATAAT
ATCATGGTCACCTTCCGGAATCAGGCCTCCCGGCCCTACAGCTTCTACAG
CTCCCTGATCAGCTACGAAGAGGACCAGAGACAGGGCGCTGAGCCCCGGA
AGAACTTCGTGAAGCCCAACGAGACTAAGACCTACTTTTGGAAGGTGCAG
CACCACATGGCCCCTACAAAGGACGAGTTCGACTGCAAGGCCTGGGCCTA
CTTCTCCGATGTGGACCTGGAAAAGGACGTGCACTCTGGGCTGATCGGCC
CCCTGCTCGTGTGCCACACCAACACCCTGAATCCCGCCCACGGCAGACAA
GTGACAGTGCAGGAATTCGCCCTGTTCTTCACCATCTTCGACGAAACAAA
GAGCTGGTACTTCACCGAAAACATGGAAAGAAACTGCCGGGCTCCCTGCA
ACATCCAGATGGAAGATCCCACCTTCAAAGAGAACTACCGGTTCCACGCC
ATCAACGGCTACATCATGGACACACTGCCCGGCCTCGTGATGGCTCAGGA
TCAGCGGATCCGGTGGTATCTGCTGTCCATGGGCTCCAACGAGAACATCC
ACAGCATCCACTTCAGCGGCCACGTGTTCACCGTGCGGAAAAAAGAAGAG

```
TACAAAATGGCCCTGTACAACCTGTACCCTGGGGTGTTCGAGACAGTGGA
AATGCTGCCCAGCAAGGCCGGCATCTGGCGGGTGGAATGTCTGATCGGCG
AGCATCTGCACGCTGGGATGAGCACACTGTTTCTGGTGTACAGCAACAAG
TGCCAGACACCTCTGGGCATGGCCTCTGGCCACATCCGGGACTTTCAGAT
CACAGCCAGCGGCCAGTATGGCCAGTGGGCCCCAAAACTGGCCAGACTGC
ACTACAGCGGCAGCATCAACGCCTGGTCCACCAAAGAGCCCTTCAGCTGG
ATCAAGGTGGACCTGCTGGCTCCCATGATCATCCACGGAATCAAGACCCA
GGGCGCCAGACAGAAGTTCAGCAGCCTGTACATCAGCCAGTTCATCATCA
TGTACAGCCTGGACGGCAAGAAGTGGCAGACCTACCGGGGCAATAGCACC
GGCACCCTGATGGTGTTCTTCGGCAACGTGGACTCCAGCGGCATTAAGCA
CAACATCTTCAACCCCCCCATCATTGCCCGGTACATCCGGCTGCACCCCA
CCCACTACAGCATCCGGTCCACCCTGAGAATGGAACTGATGGGCTGCGAC
CTGAACTCCTGCAGCATGCCCCTGGGGATGGAAAGCAAGGCCATCTCCGA
CGCCCAGATCACCGCCTCCAGCTACTTCACCAACATGTTCGCCACCTGGT
CCCCATCCAAGGCCCGGCTGCATCTGCAGGGCAGAAGCAATGCTTGGAGG
CCCCAAGTGAACAACCCCAAAGAATGGCTGCAGGTGGACTTCCAGAAAAC
CATGAAAGTGACCGGCGTGACCACCCAGGGCGTGAAGTCTCTGCTGACCT
CTATGTACGTGAAAGAGTTCCTGATCTCCAGCAGCCAGGACGGCCACCAG
TGGACCCTGTTTTTCCAGAACGGCAAAGTGAAAGTGTTTCAGGGGAACCA
GGACTCCTTCACCCCCGTCGTGAATAGCCTGGACCCTCCACTGCTGACCA
GATACCTGCGGATCCACCCTCAGAGTTGGGTGCACCAGATTGCTCTGCGG
ATGGAAGTGCTGGGATGCGAGGCCCAGGACCTGTACTGACACTAGTAATA
AAAGATCAGAGCTGTAGAGATCTGTGTGTTGGTTTTTTGTGTGCGGCCGG
TACCAGGAACCCCTAGTGATGGAGTTGGCCACTCCCTCTCTGCGCGCTCG
CTCGCTCACTGAGGCCGGGCGACCAAAGGTCGCCCGACGCCCGGGCTTTG
CCCGGGCGGCCTCAGTGAGCGAGCGAGCGCGCAGAGAGGGAGTGGCC
``` mTTR202opt (SEQ ID NO: 2)
```
TGTCTGTCTGCACATTTCGTAGAGCGAGTGTTCCGATACTCTAATCCCC
GGGGCAAAGGTCGTATTGACTTAGGTTACTTATTCTCCTTTTGTTGACTA
AGTCAATAATCAGAATCAGCAGGTTTGGAGTCAGCTTGGCAGGGATCAGC
AGCCTGGGTTGGAAGGAGGGGGTATAAAAGCCCCTTCACCAGGAGAAGC
GTCACACAGATCCACAAGCTCCTGCTAGC
``` mTTR482opt (SEQ ID NO: 3)
```
CTACCTGCTGATCGCCCGGCCCCTGTTCAAACATGTCCTAATACTCTGTC
GGGGCAAAGGTCGGCAGTAGTTTTCCATCTTACTCAACATCCTCCCAGTG
TACGTAGGATCCTGTCTGTCTGCACATTTCGTAGAGCGAGTGTTCCGATA
CTCTAATCTCCCGGGGCAAAGGTCGTATTGACTTAGGTTACTTATTCTCC
TTTTGTTGACTAAGTCAATAATCAGAATCAGCAGGTTTGGAGTCAGCTTG
GCAGGGATCAGCAGCCTGGGTTGGAAGGAGGGGGTATAAAAGCCCCTTCA
CCAGGAGAAGCCGTCACACAGATCCACAAGCTCCTGCTAGC
``` pTGENcaprh8R-ITRmTTRFVIII (TriplePlay plasmid with AAVrh8R capsid and 5.1 kb ITR-mTTR-hFVIIIco) 13524 bp (SEQ ID NO: 4)
```
GAATGCAATTGTTGTTGTTAACTTGTTTATTGCAGCTTATAATGGTTACA
AATAAAGCAATAGCATCACAAATTTCACAAATAAAGCATTTTTTTCACTG
CATTCTAGTTGTGGTTTGTCCAAACTCATCAATGTATCTTATCATGTCTG
GATCCGCTAGAACTAGGAATTCGCTAGCGGTACCGATATCCTAGTGGATC
CCCCGTACACAGGAAGTGACAATTTTCGCGCGGTTTTAGGCGGATGTTGT
AGTAAATTTGGGCGTAACCGAGTAAGATTTGGGTGGTCACGCTGGGTATT
TAAGCCCGAGTGAGCACGCAGGGTCTCCATTTTGAAGCGGGAGGTTTGAA
CGCGCAGCCGCCATGCCGGGGTTTTACGAGATTGTGATTAAGGTCCCCAG
CGACCTTGACGAGCATCTGCCCGGCATTTCTGACAGCTTTGTGAACTGGG
TGGCCGAGAAGGAATGGGAGTTGCCGCCAGATTCTGACATGGATCTGAAT
CTGATTGAGCAGGCACCCCTGACCGTGGCCGAGAAGCTGCAGCGCGACTT
TCTGACGGAATGGCGCCGTGTGAGTAAGGCCCCGGAGGCCCTTTTCTTTG
TGCAATTTGAGAAGGGAGAGCTACTTCCACATGCACGTGCTCGTGGAA
ACCACCGGGGTGAAATCCATGGTTTTGGGACGTTTCCTGAGTCAGATTCG
CGAAAAACTGATTCAGAGAATTTACCGCGGGATCGAGCCGACTTTGCCAA
ACTGGTTCGCGGTCACAAAGACCAGAAATGGCGCCGGAGGCGGGAACAAG
GTGGTGGATGAGTGCTACATCCCCAATTACTTGCTCCCCAAAACCCAGCC
TGAGCTCCAGTGGGCGTGGACTAATATATGGAACAGTATTTAAGCGCCTGTT
TGAATCTCACGGAGCGTAAACGGTTGGTGGCGCAGCATCTGACGCACGTG
TCGCAGACGCAGGAGCAGAACAAAGAGAATCAGAATCCCAATTCTGATGC
GCCGGTGATCAGATCAAAAACTTCAGCCAGGTACATGGAGCTGGTCGGGT
GGCTCGTGGACAAGGGGATTACCTCGGAGAAGCAGTGGATCCAGGAGGAC
CAGGCCTCATACATCTCCTTCAATGCGGCCTCCAACTCGCGGTCCCAAAT
CAAGGCTGCCTTGGACAATGCGGGAAAGATTATGAGCCTGACTAAAACCG
CCCCCGACTACCTGGTGGGCCAGCAGCCCGTGGAGGACATTTCCAGCAAT
CGGATTTATAAAATTTTGGAACTAAACGGGTACGATCCCCAATATGCGGC
TTCCGTCTTTCTGGGATGGGCCACGAAAAAGTTCGGCAAGAGGAACACCA
TCTGGCTGTTTGGGCCTGCAACTACCGGGAAGACCAACATCGCGGAGGCC
ATAGCCCACACTGTGCCCTTCTACGGGTGCGTAAACTGGACCAATGAGAA
CTTTCCCTTCAACGACTGTGTCGACAAGATGGTGATCTGGTGGGAGGAGG
GGAAGATGACCGCCAAGGTCGTGGAGTCGGCCAAAGCCATTCTCGGAGGA
AGCAAGGTGCGCGTGGACCAGAAATGCAAGTCCTCGGCCCAGATAGACCC
GACTCCCGTGATCGTCACCTCCAACACCAACATGTGCGCCGTGATTGACG
GGAACTCAACGACCTTCGAACACCAGCAGCCGTTGCAAGACCGGATGTTC
AAATTTGAACTCACCCGCCGTCTGGATCATGACTTTGGGAAGGTCACCAA
GCAGGAAGTCAAAGACTTTTTCCGGTGGGCAAAGGATCACGTGGTTGAGG
```

```
TGGAGCATGAATTCTACGTCAAAAAGGGTGGAGCCAAGAAAAGACCCGCC
CCCAGTGACGCAGATATAAGTGAGCCCAAACGGGTGCGCGAGTCAGTTGC
GCAGCCATCGACGTCAGACGCGGAAGCTTCGATCAACTACGCAGACAGGT
ACCAAAACAAATGTTCTCGTCACGTGGGCATGAATCTGATGCTGTTTCCC
TGCAGACAATGCGAGAGAATGAATCAGAATTCAAATATCTGCTTCACTCA
CGGACAGAAAGACTGTTTAGAGTGCTTTCCCGTGTCAGAATCTCAACCCG
TTTCTGTCGTCAAAAAGGCGTATCAGAAACTGTGCTACATTCATCATATC
ATGGGAAAGGTGCCAGACGCTTGCACTGCCTGCGATCTGGTCAATGTGGA
TTTGGATGACTGCATCTTTGAACAATAAATGATTTAAATCAGGTATGGCT
GCCGATGGTTATCTTCCAGATTGGCTCGAGGACAACCTCTCTGAGGGCAT
TCGCGAGTGGTGGGACCTGAAACCTGGAGCCCCGAAACCCAAAGCCAACC
AGCAAAAGCAGGACGACGGCCGGGGTCTGGTGCTTCCTGGCTACAAGTAC
CTCGGACCCTTCAACGGACTCGACAAGGGGGAGCCCGTCAACGCGGCGGA
CGCAGCGGCCCTCGAGCACGACAAGGCCTACGACCAGCAGCTCAAAGCGG
GTGACAATCCGTACCTGCGGTATAACCACGCCGACGCCGAGTTTCAGGAG
CGTCTGCAAGAAGATACGTCTTTTGGGGGCAACCTCGGGCGAGCAGTCTT
CCAGGCCAAGAAGCGGGTTCTCGAACCTCTCGGTCTGGTTGAGGAAGGCG
CTAAGACGGCTCCTGGAAAGAAGAGACCGGTAGAGCAGTCACCCCAAGAA
CCAGACTCATCCTCGGGCATCGGCAAATCAGGCCAGCAGCCCGCTAAAAA
GAGACTCAATTTTGGTCAGACTGGCGACTCAGAGTCAGTCCCCGACCCAC
AACCTCTCGGAGAACCTCCAGAAGCCCCCTCAGGTCTGGGACCTAATACA
ATGGCTTCAGGCGGTGGCGCTCCAATGGCAGACAATAACGAAGGCGCCGA
CGGAGTGGGTAATTCCTCGGGAAATTGGCATTGCGATTCCACATGGCTGG
GGGACAGAGTCATCACCACCAGCACCCGAACCTGGGCATTGCCCACCTAC
AACAACCACCTCTACAAGCAAATCTCCAATGGAACATCGGGAGGAAGCAC
CAACGACAACACCTACTTTGGCTACAGCACCCCCTGGGGGTATTTTGACT
TCAACAGATTCCACTGCCACTTCTCACCACGTGACTGGCAGCGACTCATC
AACAACAACTGGGGATTCCGGCCAAAGAGACTCAACTTCAAGCTGTTCAA
CATCCAGGTCAAGGAGGTTACGACGAACGAAGGCACCAAGACCATCGCCA
ATAACCTTACCAGCACCGTCCAGGTCTTTACGGACTCGGAGTACCAGCTA
CCGTACGTCCTAGGCTCTGCCCACCAAGGATGCCTGCCACCGTTTCCTGC
AGACGTCTTCATGGTTCCTCAGTACGGCTACCTGACGCTCAACAATGGAA
GTCAAGCGTTAGGACGTTCTTCTTTCTACTGTCTGGAATACTTCCCTTCT
CAGATGCTGAGAACCGGCAACAACTTTCAGTTCAGCTACACTTTCGAGGA
CGTGCCTTTCCACAGCAGCTACGCACACAGCCAGAGTCTAGATCGACTGA
TGAACCCCCTCATCGACCAGTACCTATACTACCTGGTCAGAACACAGACA
ACTGGAACTGGGGGAACTCAAACTTTGGCATTCAGCCAAGCAGGCCCTAG
CTCAATGGCCAATCAGGCTAGAAACTGGGTACCCGGGCCTTGCTACCGTC
AGCAGCGCGTCTCCACAACCACCAACCAAAATAACAACAGCAACTTTGCG
TGGACGGAGCTGCTAAATTCAAGCTGAACGGGAGAGACTCGCTAATGAA
TCCTGGCGTGGCTATGGCATCGCACAAAGACGACGAGGACCGCTTCTTTC
```

```
CATCAAGTGGCGTTCTCATATTTGGCAAGCAAGGAGCCGGGAACGATGGA
GTCGACTACAGCCAGGTGCTGATTACAGATGAGGAAGAAATTAAAGCCAC
CAACCCTGTAGCCACAGAGGAATACGGAGCAGTGGCCATCAACAACCAGG
CCGCTAACACGCAGGCGCAAACTGGACTTGTGCATAACCAGGGAGTTATT
CCTGGTATGGTCTGGCAGAACCGGGACGTGTACCTGCAGGGCCCTATTTG
GGCTAAAATACCTCACACAGATGGCAACTTTCACCCGTCTCCTCTGATGG
GTGGATTTGGACTGAAACACCCACCTCCACAGATTCTAATTAAAAATACA
CCAGTGCCGGCAGATCCTCCTCTTACCTTCAATCAAGCCAAGCTGAACTC
TTTCATCACGCAGTACAGCACGGGACAAGTCAGCGTGGAAATCGAGTGGG
AGCTGCAGAAAGAAACAGCAAGCGCTGGAATCCAGAGATCCAGTATACT
TCAAACTACTACAAATCTACAAATGTGGACTTTGCTGTCAATACCGAAGG
TGTTTACTCTGAGCCTCGCCCCATTGGTACTCGTTACCTCACCCGTAATT
TGTAATTGCCTGTTAATCAATAAACCGGTTAATTCGTTTCAGTTGAACTT
TGGTCTCTGCGGGCCGGCCTTAATTAACATGTGAGCAAAAGGCCAGCAAA
AGGCCAGGAACCGTAAAAAGGCCGCGTTGCTGGCGTTTTTCCATAGGCTC
CGCCCCCTGACGAGCATCACAAAAATCGACGCTCAAGTCAGAGGTGGCG
AAACCCGACAGGACTATAAAGATACCAGGCGTTTCCCCCTGGAAGCTCCC
TCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTA
TCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAG
TCCAACCCGGTAAGACACGACTTATCGCCACTGGCAGTAGCCACTGGTAA
CAGGATTAGCAGAGCGAGGTATGTAGGCGGTGCTACAGAGTTCTTGAAGT
GGTGGCCTAACTACGGCTACACTAGAAGAACAGTATTTGGTATCTGCGCT
CTGCTGAAGCCAGTTACCTTCGGAAAAAGAGTTGGTAGCTCTTGATCCGG
CAAACAAACCACCGCTGGTAGCGGTGGTTTTTTTGTTTGCAAGCAGCAGA
TTACGCGCAGAAAAAAAGGATCTCAAGAAGATCCTTTGATCTTTTCTACG
GGGTCTGACGCTCAGTGGAACGAAAACTCACGTTAAGGGATTTTGGTCAT
GAGATTATCAAAAAGGATCTTCACCTAGATCCTTTTCACGTAGAAAGCCA
GTCCGCAGAAACGGTGCTGACCCCGGATGAATGTCAGCTACTGGGCTATC
TGGACAAGGGAAAACGCAAGCGCAAAGAGAAAGCAGGTAGCTTGCAGTGG
GCTTACATGGCGATAGCTAGACTGGGCGGTTTTATGGACAGCAAGCGAAC
CGGAATTGCCAGCTGGGGCGCCCTCTGGTAAGGTTGGGAAGCCCTGCAAA
GTAAACTGGATGGCTTTCTTGCCGCCAAGGATCTGATGGCGCAGGGGATC
AAGATCCGATCAAGAGACAGGATGAGGATCGTTTCGCATGATTGAACAAG
ATGGATTGCACGCAGGTTCTCCGGCCGCTTGGGTGGAGAGGCTATTCGGC
TATGACTGGGCACAACAGACAATCGGCTGCTCTGATGCCGCCGTGTTCCG
GCTGTCAGCGCAGGGGCGCCCGGTTCTTTTTGTCAAGACCGACCTGTCCG
GTGCCCTGAATGAACTGCAAGACGAGGCAGCGCGGCTATCGTGGCTGGCC
ACGACGGGCGTTCCTTGCGCAGCTGTGCTCGACGTTGTCACTGAAGCGGG
```

-continued

AAGGGACTGGCTGCTATTGGGCGAAGTGCCGGGGCAGGATCTCCTGTCAT
CTCACCTTGCTCCTGCCGAGAAAGTATCCATCATGGCTGATGCAATGCGG
CGGCTGCATACGCTTGATCCGGCTACCTGCCCATTCGACCACCAAGCGAA
ACATCGCATCGAGCGAGCACGTACTCGGATGGAAGCCGGTCTTGTCGATC
AGGATGATCTGGACGAAGAGCATCAGGGGCTCGCGCCAGCCGAACTGTTC
GCCAGGCTCAAGGCGAGCATGCCCGACGGCGAGGATCTCGTCGTGACCCA
TGGCGATGCCTGCTTGCCGAATATCATGGTGGAAAATGGCCGCTTTTCTG
GATTCATCGACTGTGGCCGGCTGGGTGTGGCGGACCGCTATCAGGACATA
GCGTTGGCTACCCGTGATATTGCTGAAGAGCTTGGCGGCGAATGGGCTGA
CCGCTTCCTCGTGCTTTACGGTATCGCCGCTCCCGATTCGCAGCGCATCG
CCTTCTATCGCCTTCTTGACGAGTTCTTCTGAATTAATTAAGCGGCCGCT
CATGAGCGGATACATATTTGAATGTATTTAGAAAAATAAACAAATAGGGG
TTCCGCGCACATTTCCCCGAAAAGTGCCACCTGACGTCAGATCCGGTGCG
GGCCTCTTCGCTATTACGCCAGCTGGCGAAAGGGGGATGTGCTGCAAGGC
GATTAAGTTGGGTAACGCCAGGGTTTTCCCAGTCACGACGTTGTAAAACG
ACGGCCAGTGAATTCGCGAGCTCTTGGCCACTCCCTCTCTGCGCGCTCGC
TCGCTCACTGAGGCCGGGCGACCAAAGGTCGCCCGACGCCCGGGCTTTGC
CCGGGCGGCCTCAGTGAGCGAGCGAGCGCGCAGAGAGGGAGTGGCCAACT
CCATCACTAGGGGTTCCTACGCGTGTCTGTCTGCACATTTCGTAGAGCGA
GTGTTCCGATACTCTAATCTCCCTAGGCAAGGTTCATATTTGTGTAGGTT
ACTTATTCTCCTTTTGTTGACTAAGTCAATAATCAGAATCAGCAGGTTTG
GAGTCAGCTTGGCAGGGATCAGCAGCCTGGGTTGGAAGGAGGGGGTATAA
AAGCCCCTTCACCAGGAGAAGCCGTCACACAGATCCACAAGCTCCTGCTA
GCAGGTAAGTGCCGTGTGTGGTTCCCGCGGGCCTGGCCTCTTTACGGGTT
ATGGCCCTTGCGTGCCTTGAATTACTGACACTGACATCCACTTTTTCTTT
TTCTCCACAGGTATCGATTCTCTAGAGCCACCATGCAGATCGAGCTGTCT
ACCTGCTTCTTCCTGTGCCTGCTGCGGTTCTGCTTCAGCGCCACCAGACG
GTACTATCTGGGCGCCGTGGAACTGAGCTGGGACTACATGCAGAGCGACC
TGGGCGAGCTGCCCGTGGATGCCAGATTCCCTCCAAGAGTGCCCAAGAGC
TTCCCCTTCAACACCTCCGTGGTGTACAAGAAAACCCTGTTCGTGGAATT
CACCGACCACCTGTTCAATATCGCCAAGCCCAGACCCCCTGGATGGGCC
TGCTGGGACCTACAATTCAGGCCGAGGTGTACGACACCGTCGTGATCACC
CTGAAGAACATGGCCAGCCACCCCGTGTCTCTGCATGCCGTGGGAGTGTC
CTACTGGAAGGCCTCTGAGGGCGCCGAGTACGACGATCAGACCAGCCAGC
GCGAGAAAGAGGACGACAAGGTGTTCCCTGGCGGCAGCCACACCTACGTG
TGGCAGGTGCTGAAAGAAAACGGCCCCATGGCCTCCGACCCTCTGTGCCT
GACATACAGCTACCTGAGCCACGTGGACCTCGTGAAGGACCTGAACAGCG
GCCTGATCGGAGCCCTGCTCGTGTGTAGAGAGGGCAGCCTGGCCAAAGAG
AAAACCCAGACCCTGCACAAGTTCATCCTGCTGTTCGCCGTGTTCGACGA
GGGCAAGAGCTGGCACAGCGAGACAAAGAACAGCCTGATGCAGGACCGGG
ACGCCGCCTCTGCTAGAGCCTGGCCCAAAATGCACACCGTGAACGGCTAC

-continued

GTGAACAGAAGCCTGCCCGGACTGATCGGCTGCCACCGGAAGTCTGTGTA
CTGGCACGTGATCGGCATGGGCACCACCCCTGAGGTGCACAGCATCTTTC
TGGAAGGACACACCTTTCTCGTGCGGAACCACCGGCAGGCCAGCCTGGAA
ATCAGCCCTATCACCTTCCTGACCGCCCAGACACTGCTGATGGACCTGGG
CCAGTTTCTGCTGTTCTGCCACATCAGCTCCCACCAGCACGACGGCATGG
AAGCCTACGTGAAGGTGGACAGCTGCCCCGAGGAACCCCAGCTGCGGATG
AAGAACAACGAGGAAGCCGAGGACTACGACGACGACCTGACCGACAGCGA
GATGGACGTGGTGCGCTTCGACGACGATAACAGCCCCAGCTTCATCCAGA
TCAGAAGCGTGGCCAAGAAGCACCCCAAGACCTGGGTGCACTATATCGCC
GCCGAGGAAGAGGACTGGGATTACGCCCCTCTGGTGCTGGCCCCCGACGA
CAGAAGCTACAAGAGCCAGTACCTGAACAATGGCCCCCAGCGGATCGGCC
GGAAGTATAAGAAAGTGCGGTTCATGGCCTACACCGACGAGACATTCAAG
ACCAGAGAGGCCATCCAGCACGAGAGCGGCATCCTGGGCCCTCTGCTGTA
TGGCGAAGTGGGCGACACCCTGCTGATCATCTTCAAGAACCAGGCCAGCA
GACCCTACAACATCTACCCTCACGGCATCACCGACGTGCGGCCCCTGTAC
TCCAGAAGGCTGCCCAAGGGCGTGAAACACCTGAAGGACTTCCCCATCCT
GCCCGGCGAGATCTTCAAGTACAAGTGGACCGTGACCGTGGAAGATGGCC
CCACCAAGAGCGACCCCAGATGCCTGACACGGTACTACAGCAGCTTCGTG
AACATGGAACGGGACCTGGCCTCCGGCCTGATTGGCCCACTGCTGATCTG
CTACAAAGAAAGCGTGGACCAGCGGGGCAACCAGATCATGAGCGACAAGC
GGAACGTGATCCTGTTTAGCGTGTTCGATGAGAACCGGTCCTGGTATCTG
ACCGAGAATATCCAGCGGTTCCTGCCCAACCCTGCCGGCGTGCAGCTGGA
AGATCCTGAGTTCCAGGCCTCCAACATCATGCACTCCATCAATGGCTATG
TGTTCGACAGCCTGCAGCTGAGCGTGTGCCTGCACGAGGTGGCCTACTGG
TACATCCTGAGCATCGGGGCCCAGACCGACTTCCTGTCCGTGTTCTTCTC
CGGCTACACCTTCAAGCACAAGATGGTGTACGAGGATACCCTGACCCTGT
TCCCCTTTAGCGGCGAAACCGTGTTCATGAGCATGGAAAACCCCGGCCTG
TGGATCCTGGGCTGCCACAACAGCGACTTCCGGAACAGAGGCATGACCGC
CCTGCTGAAGGTGTCCAGCTGCGACAAGAACACCGGCGACTACTACGAGG
ACAGCTATGAGGACATCAGCGCCTACCTGCTGAGCAAGAACAATGCCATC
GAGCCCAGAAGCTTCAGCCAGAACCCCCCCGTGCTGAAGCGGCACCAGAG
AGAGATCACCCGGACCACCCTGCAGTCCGACCAGGAAGAGATCGATTACG
ACGACACCATCAGCGTGGAAATGAAGAAAGAAGATTTCGACATCTACGAC
GAGGACGAGAACCAGAGCCCCCGGTCCTTTCAGAAAAAGACCCGGCACTA
CTTCATTGCCGCTGTGGAACGGCTGTGGGACTACGGCATGAGCAGCAGCC
CTCACGTGCTGAGAAACAGGGCCCAGAGCGGCAGCGTGCCCCAGTTCAAG
AAAGTGGTGTTCCAGGAATTCACAGACGGCAGCTTCACCCAGCCTCTGTA
CCGCGGCGAGCTGAATGAGCACCTGGGACTGCTGGGCCCCTATATCAGAG
CCGAAGTGGAAGATAATATCATGGTCACCTTCCGGAATCAGGCCTCCCGG
CCCTACAGCTTCTACAGCTCCCTGATCAGCTACGAAGAGGACCAGAGACA

```
GGGCGCTGAGCCCCGGAAGAACTTCGTGAAGCCCAACGAGACTAAGACCT
ACTTTTGGAAGGTGCAGCACCACATGGCCCCTACAAAGGACGAGTTCGAC
TGCAAGGCCTGGGCCTACTTCTCCGATGTGGACCTGGAAAAGGACGTGCA
CTCTGGGCTGATCGGCCCCTGCTCGTGTGCCACACCAACACCCTGAATC
CCGCCCACGGCAGACAAGTGACAGTGCAGGAATTCGCCCTGTTCTTCACC
ATCTTCGACGAAACAAAGAGCTGGTACTTCACCGAAAACATGGAAAGAAA
CTGCCGGGCTCCCTGCAACATCCAGATGGAAGATCCCACCTTCAAAGAGA
ACTACCGGTTCCACGCCATCAACGGCTACATCATGGACACACTGCCCGGC
CTCGTGATGGCTCAGGATCAGCGGATCCGGTGGTATCTGCTGTCCATGGG
CTCCAACGAGAACATCCACAGCATCCACTTCAGCGGCCACGTGTTCACCG
TGCGGAAAAAAGAAGAGTACAAAATGGCCCTGTACAACCTGTACCCTGGG
GTGTTCGAGACAGTGGAAATGCTGCCCAGCAAGGCCGGCATCTGGCGGGT
GGAATGTCTGATCGGCGAGCATCTGCACGCTGGGATGAGCACACTGTTTC
TGGTGTACAGCAACAAGTGCCAGACACCTCTGGGCATGGCCTCTGGCCAC
ATCCGGGACTTTCAGATCACAGCCAGCGGCCAGTATGGCCAGTGGGCCCC
AAAACTGGCCAGACTGCACTACAGCGGCAGCATCAACGCCTGGTCCACCA
AGAGCCCTTCAGCTGGATCAAGGTGGACCTGCTGGCTCCCATGATCATC
CACGGAATCAAGACCCAGGGCGCCAGACAGAAGTTCAGCAGCCTGTACAT
CAGCCAGTTCATCATCATGTACAGCCTGGACGGCAAGAAGTGGCAGACCT
ACCGGGGCAATAGCACCGGCACCCTGATGGTGTTCTTCGGCAACGTGGAC
TCCAGCGGCATTAAGCACAACATCTTCAACCCCCCCATCATTGCCCGGTA
CATCCGGCTGCACCCCACCCACTACAGCATCCGGTCCACCCTGAGAATGG
AACTGATGGGCTGCGACCTGAACTCCTGCAGCATGCCCCTGGGGATGGAA
AGCAAGGCCATCTCCGACGCCCAGATCACCGCCTCCAGCTACTTCACCAA
CATGTTCGCCACCTGGTCCCCATCCAAGGCCCGGCTGCATCTGCAGGGCA
GAAGCAATGCTTGGAGGCCCCAAGTGAACAACCCCAAAGAATGGCTGCAG
GTGGACTTCCAGAAAACCATGAAAGTGACCGGCGTGACCACCCAGGGCGT
GAAGTCTCTGCTGACCTCTATGTACGTGAAAGAGTTCCTGATCTCCAGCA
GCCAGGACGGCCACCAGTGGACCCTGTTTTTCCAGAACGGCAAAGTGAAA
GTGTTTCAGGGGAACCAGGACTCCTTCACCCCCGTCGTGAATAGCCTGGA
CCCTCCACTGCTGACCAGATACCTGCGGATCCACCCTCAGAGTTGGGTGC
ACCAGATTGCTCTGCGGATGGAAGTGCTGGGATGCGAGGCCCAGGACCTG
TACTGACAACTAGTAATAAAAGATCAGAGCTGTAGAGATCTGTGTGTTGG
TTTTTTGTGTGCGGCCGGTACCCAGGAACCCCTAGTGATGGAGTTGGCCA
CTCCCTCTCTGCGCGCTCGCTCGCTCACTGAGGCCGGGCGACCAAAGGTC
GCCCGACGCCCGGGCTTTGGTCGGGCGGCCTCAGTGAGCGAGCGAGCGCG
CAGAGAGGGAGTGGCCGGAAGCTTGGCGTAATCATGGTCATAGCTGTTTC
CTGTGTGAAATTGTTATCCGCTCACAATTCCACACAACATACGAGCCGGA
AGCATAAAGTGTAAAGCCTGGGGTGCCTAATGAGTGAGCTAACTCACATT
AATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATT
```
```
GGGCGCTCTTCCGCTGATCTCATACTAGCGAACGCCAGCAAGACGTAGCC
CAGCGCGTCGGCCCCGAGATGCGCCGCGTGCGGCTGCTGGAGATGGCGGA
CGCGATGGATATGTTCTGCCAAGGGTTGGTTTGCGCATTCACAGTTCTCC
GCAAGAATTGATTGGCTCCAATTCTTGGAGTGGTGAATCCGTTAGCGAGG
TGCCGCCCTGCTTCATCCCCGTGGCCCGTTGCTCGCGTTTGCTGGCGGTG
TCCCCGGAAGAAATATATTTGCATGTCTTTAGTTCTATGATGACACAAAC
CCCGCCCAGCGTCTTGTCATTGGCGAATTCCGGCTGTGGAATGTGTGTCA
GTTAGGGTGTGGAAAGTCCCCAGGCTCCCCAGCAGGCAGAAGTATGCAAA
GCATGCATCTCAATTAGTCAGCAACCAGGTGTGGAAAGTCCCCAGGCTCC
CCAGCAGGCAGAAGTATGCAAAGCATGCATCTCAATTAGTCAGCAACCAT
AGTCCCGCCCCTAACTCCGCCCATCCCGCCCCTAACTCCGCCCAGTTCCG
CCCATTCTCCGCCCCATGGCTGACTAATTTTTTTTATTTATGCAGAGGCC
GAGGCCGCCTCGGCCTCTGAGCTATTCCAGAAGTAGTGAGGAGGCTTTTT
TGGAGGCCTAGGCTTTTGCAAAAAGCTTGCATGCCTGCAGGTCGGCCGCC
ACGACCGGTGCCGCCACCATCCCCTGACCCACGCCCCTGACCCCTCACAA
GGAGACGACCTTCCATGACCGAGTACAAGCCCACGGTGCGCCTCGCCACC
CGCGACGACGTCCCCGGGCCGTACGCACCCTCGCCGCCGCGTTCGCCGA
CTACCCCGCCACGCGCCACACCGTCGACCCGGACCGCCACATCGAGCGGG
TCACCGAGCTGCAAGAACTCTTCCTCACGCGCGTCGGGCTCGACATCGGC
AAGGTGTGGGTCGCGGACGACGGCGCCGCGGTGGCGGTCTGGACCACGCC
GGAGAGCGTCGAAGCGGGGCGGTGTTCGCCGAGATCGGCCCGCGCATGG
CCGAGTTGAGCGGTTCCCGGCTGGCCGCGCAGCAACAGATGGAAGGCCTC
CTGGCGCCGCACCGGCCCAAGGAGCCCGCGTGGTTCCTGGCCACCGTCGG
CGTCTCGCCCGACCACCAGGGCAAGGGTCTGGGCAGCGCCGTCGTGCTCC
CCGGAGTGGAGGCGGCCGAGCGCGCCGGGGTGCCCGCCTTCCTGGAGACC
TCCGCGCCCCGCAACCTCCCCTTCTACGAGCGGCTCGGCTTCACCGTCAC
CGCCGACGTCGAGGTGCCCGAAGGACCGCGCACCTGGTGCATGACCCGCA
AGCCCGGTGCCTGACGCCCGCCCCACGACCCGCAGCGCCCGACCGAAAGG
AGCGCACGACCCCATGGCTCCGACCGAAGCCACCCGGGGCGGCCCCGCCG
ACCCCGCACCCGCCCCCGAGGCCCACCGACTCTAGAGGATCATAATCAGC
CATACCACATTTGTAGAGGTTTTACTTGCTTTAAAAAACCTCCCACACCT
CCCCCTGAACCTGAAACATAAAAT
```

What is claimed is:

1. A method for producing an adeno-associated virus (AAV) particle comprising an oversized recombinant AAV genome, the method comprising
   a) culturing an AAV producer cell line under conditions to generate rAAV particles, wherein the AAV producer cell line comprises
      i) nucleic acid encoding AAV rep and cap genes, and
      ii) a rAAV genome, wherein the rAAV genome is 5.4 kb or greater;
   b) providing AAV helper functions; and
   c) collecting the rAAV particles comprising oversized rAAV genomes;
   wherein the nucleic acid encoding AAV rep and cap genes and/or the oversized rAAV genome are stably integrated into the genome of the producer cell line.

2. The method of claim 1, wherein the rAAV genome comprises one or more AAV inverted terminal repeats (ITRs) and a heterologous transgene.

3. The method of claim 1, wherein the rAAV genome is between 5.4 kb and 9.4 kb.

4. The method of claim 1, wherein the AAV particles collected in step c) comprise rAAV genomes between 5.4 kb and 9.4 kb.

5. The method of claim 2, wherein the heterologous transgene encodes Factor VIII, dystrophin, dysferlin or cystic fibrosis transmembrane conductance regulator (CFTR).

6. The method of claim 2, wherein the heterologous transgene is operably linked to a promoter.

7. The method of claim 6, wherein the promoter is the mouse transthyretin (mTTR) promoter.

8. The method of claim 1, wherein the rAAV genome comprises an intron.

9. The method of claim 1, wherein the rAAV genome comprises a polyadenylation signal.

10. The method of claim 1, wherein the rAAV particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid.

11. The method of claim 2, wherein the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs.

12. The method of claim 10, wherein the AAV particles comprise AAV2 ITRs and AAVrh8R or AAV8 capsid.

13. The method of claim 1, wherein the AAV helper functions are provided by adenovirus, HSV or baculovirus.

14. The method of claim 13, wherein the rAAV particles are collected from between about 48 hours and about 96 hours after the provision of helper functions.

15. The method of claim 1, further comprising purification of the rAAV particles.

16. A rAAV particle comprising an oversized rAAV genome produced by a method for producing the AAV particle comprising an oversized recombinant AAV genome, the method comprising
 a) culturing an AAV producer cell line under conditions to generate rAAV particles, wherein the AAV producer cell line comprises
  i) nucleic acid encoding AAV rep and cap genes, and
  ii) a rAAV genome, wherein the rAAV genome is 5.4 kb or greater;
 b) providing AAV helper functions; and
 c) collecting the rAAV particles comprising oversized rAAV genomes;
 wherein the nucleic acid encoding AAV rep and cap genes and/or the oversized rAAV genome are stably integrated into the genome of the producer cell line.

17. A composition comprising rAAV particles wherein at least about 45% of the rAAV particle encapsidate an rAAV genome 5.4 kb or greater
 wherein the AAV particles are produced by a method for producing the AAV particle comprising an oversized recombinant AAV genome, the method comprising
 a) culturing an AAV producer cell line under conditions to generate rAAV particles, wherein the AAV producer cell line comprises
  i) nucleic acid encoding AAV rep and cap genes, and
  ii) a rAAV genome, wherein the rAAV genome is 5.4 kb or greater;
 b) providing AAV helper functions; and
 c) collecting the rAAV particles comprising oversized rAAV genomes;
 wherein the nucleic acid encoding AAV rep and cap genes and/or the oversized rAAV genome are stably integrated into the genome of the producer cell line.

18. A cell line for producing an adeno-associated virus (AAV) particle comprising an oversized recombinant AAV genome, the cell line comprising
 a) nucleic acid encoding AAV rep and cap genes, and
 b) a rAAV genome, wherein the rAAV genome is 5.4 kb or greater;
 wherein the nucleic acid encoding AAV rep and cap genes and/or the oversized rAAV genome are stably integrated into the genome of the producer cell line.

19. An adeno-associated virus (AAV) particle comprising a rAAV genome encapsidated by an AAV capsid, wherein the rAAV genome is 6 kb or greater.

20. A rAAV vector comprising a rAAV genome, wherein the rAAV genome comprises 5' to 3' an AAV2 ITR, a mTTR promoter, a synthetic intron, a transgene encoding human FVIII, a synthetic polyadenylation sequence, and an AAV2 ITR, wherein the rAAV genome is 6 kb or greater.

21. The rAAV vector of claim 20, wherein the synthetic polyadenylation sequence is a bovine growth hormone synthetic polyadenylation sequence.

22. A method for treatment of a disease or disorder in an individual comprising administering an effective amount of an AAV particle comprising an oversized AAV genome, wherein the oversized AAV genome comprises a transgene suitable for treating the disease or disorder, and wherein the oversized AAV genome is 6 kb or greater, and wherein the method results in treatment of the disease or disorder in the individual.

* * * * *